United States Patent
Bates et al.

(10) Patent No.: US 10,980,810 B2
(45) Date of Patent: Apr. 20, 2021

(54) COMBINATION THERAPY COMPRISING AN ACC INHIBITOR

(71) Applicant: Gilead Sciences, Inc., Foster City, CA (US)

(72) Inventors: Jamie Geier Bates, Burlingame, CA (US); Adrian S. Ray, Burlingame, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/153,497

(22) Filed: Oct. 5, 2018

(65) Prior Publication Data

US 2019/0134041 A1 May 9, 2019

Related U.S. Application Data

(60) Provisional application No. 62/655,704, filed on Apr. 10, 2018, provisional application No. 62/593,806, filed on Dec. 1, 2017, provisional application No. 62/569,375, filed on Oct. 6, 2017.

(51) Int. Cl.
*A61K 31/519* (2006.01)
*A61K 31/216* (2006.01)
*A61P 1/16* (2006.01)

(52) U.S. Cl.
CPC .......... *A61K 31/519* (2013.01); *A61K 31/216* (2013.01); *A61P 1/16* (2018.01)

(58) Field of Classification Search
CPC .................................................. A61K 31/519
See application file for complete search history.

(56) References Cited

U.S. PATENT DOCUMENTS

| | | | |
|---|---|---|---|
| 8,969,557 B2 | 3/2015 | Harriman et al. | |
| 9,139,539 B2 | 9/2015 | Kinzel et al. | |
| 9,453,026 B2 | 9/2016 | Harriman et al. | |
| 9,944,655 B2 | 4/2018 | Harriman et al. | |
| 10,183,951 B2 | 1/2019 | Amedio, Jr. et al. | |
| 10,472,374 B2 | 11/2019 | Bhat et al. | |
| 10,487,090 B2 | 11/2019 | Calimsiz et al. | |
| 2016/0136138 A1* | 5/2016 | Shibata | A61P 43/00 514/375 |
| 2018/0021341 A1 | 1/2018 | Harriman et al. | |
| 2018/0280394 A1 | 10/2018 | Bates et al. | |
| 2018/0298025 A1 | 10/2018 | Geier et al. | |
| 2019/0247343 A1* | 8/2019 | Laruelle | A61K 9/0019 |
| 2019/0381045 A1 | 12/2019 | Harriman et al. | |
| 2020/0102323 A1 | 4/2020 | Bhat et al. | |
| 2020/0148699 A1 | 5/2020 | Alexander et al. | |

FOREIGN PATENT DOCUMENTS

| | | | |
|---|---|---|---|
| FR | 3050112 A1 * | 10/2017 | A61K 9/0007 |
| WO | WO-2014/174524 | 10/2014 | |
| WO | WO-2016/046311 | 3/2016 | |
| WO | WO-2016/112305 | 7/2016 | |
| WO | WO-2016112305 A1 * | 7/2016 | A61K 45/06 |

OTHER PUBLICATIONS

Eshraghian, Current and emerging pharmacological therapy for nonalcoholic fatty liver disease, World J Gastroenterol Nov. 14, 2017; 23(42): 7495-750.*
Alkhouri et al, Noninvasive Diagnosis of NASH and Liver Fibrosis Within the Spectrum of NAFLD, Gastroenterol Hepatol (N Y). Oct. 2012; 8(10): 661-668.*
Kostapanos et al., Current role of fenofibrate in the prevention and management of non-alcoholic fatty liver disease, World J Hepatol Sep. 27, 2013; 5(9): 470-478.*
Bates et al., "A liver-targeted acetyl CoA carboxylase inhibitor reduces hepatic steatosis and liver injury in a murine model of NASH", Journal of Hepatology, vol. 66, No. 1, Apr. 1, 2017, XP085012355.
Fenofibrate Prescribing Information. Shionogi Inc. Reference ID: 3245094. Revised Jan. 2013. 15 pages.
Gilead Press Release, "Gilead Announces Phase 2 Results for GS-0976 in Nonalcoholic Steatohepatitis (NASH)", Oct. 24, 2017, retrieved Nov. 6, 2019, 4 pages.
Goedeke et al., "Acetyl-CoA carboxylase inhibition reverses NAFLD and hepatic insulin resistance but promotes hyptertriglyceridemia in rodents", Hepatology, 2018, Hepatology, vol. 68, No. 6, pp. 2197-2211.
Goedeke et al., "Mechanism for hypertriglyceridemia and effect of fibrate coadministration during acetyl-CoA carboxylase inhibitor treatment", EASL The International Liver Congress, Apr. 11-15, 2018, Paris, Abstract, 1 page.
Goedeke et al., "Mechanism for hypertriglyceridemia and effect of fibrate coadministration during acetyl-CoA carboxylase inhibitor treatment", EASL The International Liver Congress, Apr. 11-15, 2018, Paris, Poster, 1 page.
International Search Report and Written Opinion for PCT/US2018/054738 dated Jan. 1, 2019, 17 pages.
Kim et al., "Acetyl CoA carboxylase inhibition reduces hepatic steatosis but elevates plasma triglycerides in mice and humans: A bedside to bench investigation", Cell Metabolism, 2017, vol. 26, pp. 394-406, doi: 10.1016/j.cmet.2017.07.009.
Lawitz et al., "Acetyl-CoA carboxylase (ACC) inhibitor GS-0976 leads to suppression of hepatic de novo lipogenesis and significant improvements in MRI-PDFF, MRE, and markers of fibrosis after 12 weeks of therapy in patients with NASH", Journal of Hepatology, 2017, vol. 66, Issue 1, Supplement, p. S34, doi: https://doi.org/10.1016/S0168-8278(17)30328-8.
Loomba et al., "GS-0976 reduces hepatic steatosis and fibrosis markers in patients with nonalcoholic fatty liver disease", Gastroenterology, Nov. 2018, vol. 155, No. 5, pp. 1463-1473, e6, doi: 10.1053/j.gastro.2018.07.027.
Stiede et al., "Acetyl-coenzyme A carboxylase inhibition reduces de novo lipogenesis in overweight male subjects: A randomized, double-blind, crossover study", Hepatology, 2017, vol. 66, No. 2, pp. 324-334.

(Continued)

*Primary Examiner* — Svetlana M Ivanova
(74) *Attorney, Agent, or Firm* — Sheppard Mullin Richter & Hampton LLP

(57) ABSTRACT

The present disclosure provides methods and compositions for treating, stabilizing or lessening the severity or progression of a non-alcoholic fatty liver disease.

20 Claims, 17 Drawing Sheets

(56) References Cited

OTHER PUBLICATIONS

Cheung et al., Combined ursodeoxycholic acid (UDCA) and fenofibrate in primary biliary cholangitis patients with incomplete UDCA response may improve outcomes, Alimentary Pharmacology and Therapeutics 2016; 43, pp. 283-293.

Hagström et al., Fibrosis stage but not NASH predicts mortality and time to development of severe liver disease in biopsy-proven NAFLD, Journal of Hepatology 2017, vol. 67, pp. 1265-1273.

International Preliminary Report on Patentability for International Application No. PCT/US2018/054738 dated Apr. 8, 2020. 9 pages.

Lawitz, et al. Fenofibrate Mitigates Increases in Serum Triglycerides Due to the ACC Inhibitor Firsocostat in Patients With Advanced Fibrosis Due to NASH. Presented at AASLD: The Liver Meeting® 2019, Nov. 8-12, 2019, Boston, MA.

Levy et al., Pilot study: fenofibrate for patients with primary biliary cirrhosis and an incomplete response to ursodeoxycholic acid, Alimentary Pharmacology and Therapeutics 2011; 33, pp. 235-242.

Gordon et al., Health Care Use and Costs Among Patients With Nonalcoholic Steatohepatitis With Advanced Fibrosis Using the Fibrosis-4 Score. Hepatology Communications, vol. 4, No. 7, 2020, pp. 998-1011.

Vilar-Gomez et al., Fibrosis Severity as a Determinant of Cause-Specific Mortality in Patients With Advanced Nonalcoholic Fatty Liver Disease: A Multi-National Cohort Study. Gastroenterology 2018;155:443-457.

\* cited by examiner

COMBINATION THERAPY COMPRISING AN ACC INHIBITOR

CROSS REFERENCE TO RELATED APPLICATIONS

This application claims the benefit under 35 U.S.C. § 119(e) to U.S. Provisional Application No. 62/569,375, filed on Oct. 6, 2017, U.S. Provisional Application No. 62/593,806, filed on Dec. 1, 2017, and U.S. Provisional Application No. 62/655,704, filed on Apr. 10, 2018, the entireties of which are incorporated herein by reference.

FIELD

Provided herein are drug combinations and methods of treating, stabilizing or lessening the severity or progression of a non-alcoholic fatty liver disease (NAFLD).

BACKGROUND

Non-alcoholic fatty liver disease (NAFLD) consists of a spectrum of conditions ranging from relatively benign steatosis to more severe non-alcoholic steatohepatitis (NASH), the latter of which can lead to fibrosis, cirrhosis, liver failure, or hepatocellular carcinoma if untreated. NAFLD is the most common cause of chronic liver disease in the United States, and is closely associated with obesity, type 2 diabetes, and metabolic syndrome.

SUMMARY

In some aspects, provided herein are methods of treating, stabilizing or lessening the severity or progression of a non-alcoholic fatty liver disease comprising administering to a patient in need thereof an Acetyl-CoA carboxylase (ACC) inhibitor in combination with a peroxisome proliferator-activated receptor alpha (PPARα) agonist or fish oil.

In some aspects, the ACC inhibitor is (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid having the formula:

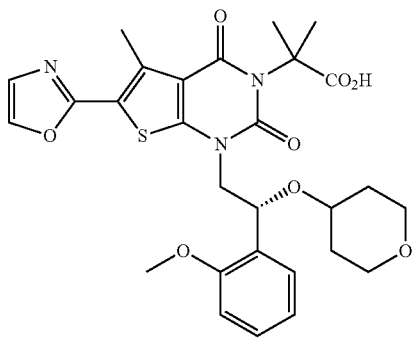 [SMILES: COc1ccccc1[C@H](Cn1c(=O)n(C(C)(C)C(=O)O)c(=O)c2c(C)c(-c3ncco3)sc21)OC1CCOCC1]

or a pharmaceutically acceptable salt, solvate or co-crystal thereof (collectively and individually referred to as "Compound 1").

In some aspects, the ACC inhibitor is 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid having the formula:

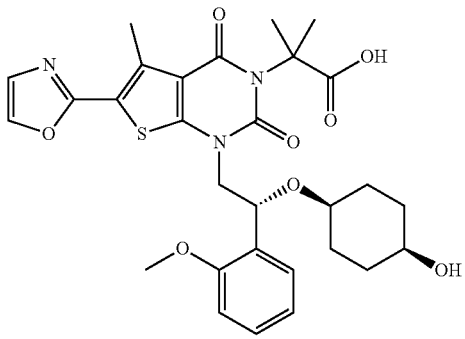 [SMILES: COc1ccccc1[C@H](Cn1c(=O)n(C(C)(C)C(=O)O)c(=O)c2c(C)c(-c3ncco3)sc21)O[C@H]1CC[C@@H](O)CC1]

or a pharmaceutically acceptable salt, solvate or co-crystal thereof (collectively and individually referred to as "Compound 2").

In some aspects, provided herein is a method of treating, stabilizing or lessening the severity or progression of a non-alcoholic fatty liver disease while reducing or eliminating the occurrence or lessening the severity of hypertriglyceridemia, wherein the method comprises administering to a patient in need thereof an ACC inhibitor in combination with a PPARα agonist or fish oil.

In some aspects, provided herein is a method of treating, stabilizing or lessening the severity or progression of a non-alcoholic steatohepatitis, wherein the method comprises administering to a patient in need thereof an ACC inhibitor in combination with a PPARα agonist or fish oil.

In some aspects, provided herein is a method of treating, stabilizing or lessening the severity or progression of a non-alcoholic steatohepatitis while reducing or eliminating the occurrence or lessening the severity of hypertriglyceridemia, wherein the method comprises administering to a patient in need thereof an ACC inhibitor in combination with a PPARα agonist or fish oil.

In some aspects, provided herein is a method of treating, stabilizing or lessening the severity or progression of a non-alcoholic fatty liver disease while reducing or eliminating the occurrence or lessening the severity of hypertriglyceridemia, wherein the method comprises administering to a patient in need thereof Compound 1 in combination with a PPARα agonist or fish oil.

In some aspects, provided herein is a method of treating, stabilizing or lessening the severity or progression of a non-alcoholic steatohepatitis, wherein the method comprises administering to a patient in need thereof Compound 1 in combination with a PPARα agonist or fish oil.

In some aspects, provided herein is a method of treating, stabilizing or lessening the severity or progression of a non-alcoholic steatohepatitis while reducing or eliminating the occurrence or lessening the severity of hypertriglyceridemia, wherein the method comprises administering to a patient in need thereof Compound 1 in combination with a PPARα agonist or fish oil.

In some aspects, provided herein is a method of treating, stabilizing or lessening the severity or progression of a non-alcoholic fatty liver disease while reducing or eliminating the occurrence or lessening the severity of hypertriglyceridemia, wherein the method comprises administering to a patient in need thereof Compound 2 in combination with a PPARα agonist or fish oil.

In some aspects, provided herein is a method of treating, stabilizing or lessening the severity or progression of a non-alcoholic steatohepatitis, wherein the method comprises administering to a patient in need thereof Compound 2 in combination with a PPARα agonist or fish oil.

In some aspects, provided herein is a method of treating, stabilizing or lessening the severity or progression of a non-alcoholic steatohepatitis while reducing or eliminating the occurrence or lessening the severity of hypertriglyceridemia, wherein the method comprises administering to a patient in need thereof Compound 2 in combination with a PPARα agonist or fish oil.

In some aspects, the present invention provides a pharmaceutical composition comprising Compound 1 or Compound 2 and a PPARα agonist, and a pharmaceutically acceptable carrier, adjuvant, or vehicle.

In some aspects, provided herein is a method of treating a non-alcoholic steatohepatitis in a non-cirrhotic patient with a non-alcoholic steatohepatitis, wherein the method comprises administering to the patient in need thereof about 20 mg of Compound 1 once daily.

In some aspects, provided herein is a method of treating non-alcoholic steatohepatitis (NASH) in a patient with compensated cirrhosis due to NASH, wherein the method comprises administering to the patient in need thereof about 20 mg of Compound 1 once daily.

Additional embodiments describing methods of utilizing a provided combination are described in detail herein, infra.

DETAILED DESCRIPTION

Figure 1:
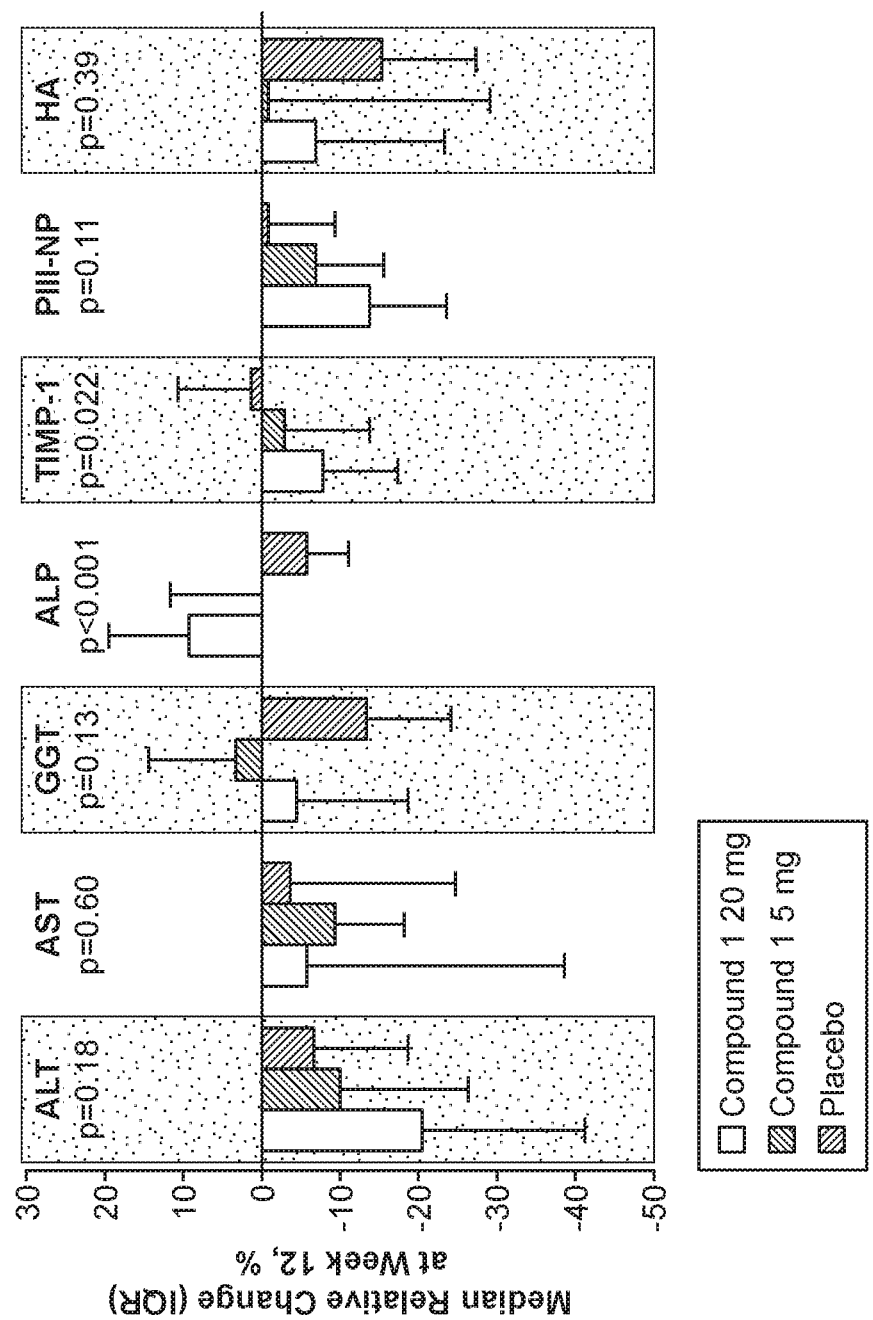
FIG. 1 illustrates the percentage of median relative change (IQR) at week 12 for markers of fibrosis (ALT, AST, GGT, ALP, TIMP-1, PII-NP, and HA). For each marker, 3 columns are shown, where the left column corresponds to Compound 1 20 mg, middle column corresponds to Compound 1 5 mg, and right column corresponds to placebo.

As described herein, in some embodiments, the present invention provides methods of treating, stabilizing or lessening the severity or progression of a non-alcoholic fatty liver disease (NAFLD) comprising administering to a patient in need thereof an ACC inhibitor in combination with PPARα agonist.

Definitions

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the agent" includes a plurality of such agents.

As used herein, the term "about" used in the context of quantitative measurements means the indicated amount ±10%, or ±5%, or ±1%. For example, "about 30%" would mean 33%–27%, or 31.5%–28.5%, or 30.3%–29.7%.

As used herein generally, "ACC inhibitor" means any therapeutic agent that reduces the activity of an acetyl CoA carboxylase enzyme.

As used herein, "non-alcoholic fatty liver disease" or "NAFLD" means any disease or other deleterious condition characterized by, and/or caused by, excess hepatic fat accumulation, including, but not limited to, steatosis, non-alcoholic steatohepatitis (NASH), liver fibrosis caused by NASH, liver cirrhosis caused by NASH, or hepatocellular carcinoma (HCC) caused by NASH.

As used herein, "hypertriglyceridemia" refers to a condition in which blood triglyceride levels are elevated to abnormal levels.

The term "subject" or "patient," as used herein, means a mammal and includes human and animal subjects, such as domestic animals (e.g., horses, dogs, cats, etc.).

As used herein, a "therapeutically effective amount" means an amount of a substance (e.g., a therapeutic agent, composition, and/or formulation), or a combination or two or more agents or compounds, or a sufficient amount of an individual agent or compound in a combination of two or more agents or compounds, that elicits a desired biological response. In some embodiments, a therapeutically effective amount of a substance is an amount that is sufficient, when administered as part of a dosing regimen to a subject suffering from or susceptible to a NAFLD, to treat, diagnose, prevent, and/or delay the onset of the NAFLD. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a NAFLD is the amount that alleviates, ameliorates, relieves, inhibits, prevents, delays onset of, reduces severity of and/or reduces incidence of one or more symptoms or features of the NAFLD. In some embodiments, a "therapeutically effective amount" is at least a minimal amount of a compound, or composition containing a compound, which is sufficient for treating one or more symptoms of a NASH.

The terms "treat" or "treating," as used herein, refers to partially or completely alleviating, inhibiting, delaying onset of, preventing, ameliorating and/or relieving a disease or disorder, or one or more symptoms of the disease or disorder. As used herein, the terms "treatment," "treat," and "treating" refer to partially or completely alleviating, inhibiting, delaying onset of, preventing, ameliorating and/or relieving a NAFLD, or one or more symptoms of the NAFLD. In some embodiments, treatment may be administered after one or more symptoms have developed. In some embodiments, the term "treating" includes preventing or halting the progression of a NAFLD. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a NAFLD.

The expression "unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

Methods of Treatment

In some aspects, provided is a method of treating, stabilizing or lessening the severity or progression of a non-alcoholic fatty liver disease (NAFLD), which method comprises administering to a patient in need thereof an ACC inhibitor in combination with a PPARα agonist. In some embodiments, provided is a method of treating, stabilizing, or lessening the severity or progression of a non-alcoholic fatty liver disease, wherein the method comprises administering to a patient in need thereof an ACC inhibitor in combination with a PPARα agonist, wherein the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar, and muraglitzar.

In some aspects, provided is a method of treating, stabilizing or lessening the severity or progression of a non-alcoholic fatty liver disease (NAFLD), which method comprises administering to a patient in need thereof an ACC inhibitor in combination with fish oil, e.g., icosapent ethyl (Vascepa®).

In some aspects, provided herein is a method of treating, stabilizing or lessening the severity or progression of a NAFLD while reducing or eliminating the occurrence or lessening the severity of hypertriglyceridemia, wherein the method comprises administering to a patient in need thereof an ACC inhibitor in combination with a PPARα agonist. In some aspects, provided herein is a method of treating, stabilizing or lessening the severity or progression of a NAFLD without substantially increasing the plasma triglyceride levels of the patient, wherein the method comprises administering to a patient in need thereof an ACC inhibitor in combination with a PPARα agonist. In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), docosahexaenoic acid, α-linolenic acid, hexadecatrienoic acid, stearidonic acid, eicosatrienoic acid, eicosatetraenoic acid, eicosapentaenoic acid, heneicosapenaenoic acid, docosapentaenoic acid, tetracosapentaenoic acid, tetracosahexaenoic acid, and the like), pirinixic acid, GW409544, AZ 242, LY518674, NS-220, AVE8134, BMS-711939, aleglitazar, muraglitzar and saroglitazar.

In some aspects, provided herein is a method of treating, stabilizing or lessening the severity or progression of a NAFLD while reducing or eliminating the occurrence or lessening the severity of hypertriglyceridemia, wherein the method comprises administering to a patient in need thereof an ACC inhibitor in combination with fish oil, e.g., icosapent ethyl (Vascepa®). In some aspects, provided herein is a method of treating, stabilizing or lessening the severity or progression of a NAFLD without substantially increasing the plasma triglyceride levels of the patient, wherein the method comprises administering to a patient in need thereof an ACC inhibitor in combination with fish oil, e.g., icosapent ethyl (Vascepa®).

In some aspects, provided is a method of treating, stabilizing or lessening the severity or progression of a non-alcoholic fatty liver disease (NAFLD), which method comprises administering to a patient in need thereof Compound 1 in combination with a PPARα agonist. In some embodiments, provided is a method of treating, stabilizing, or lessening the severity or progression of a non-alcoholic fatty liver disease, wherein the method comprises administering to a patient in need thereof Compound 1 in combination with a PPARα agonist, wherein the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar, and muraglitzar.

In some aspects, provided is a method of treating, stabilizing or lessening the severity or progression of a non-alcoholic fatty liver disease (NAFLD), which method comprises administering to a patient in need thereof Compound 1 in combination with fish oil.

In some aspects, provided herein is a method of treating, stabilizing or lessening the severity or progression of a NAFLD while reducing or eliminating the occurrence or lessening the severity of hypertriglyceridemia, wherein the method comprises administering to a patient in need thereof Compound 1 in combination with a PPARα agonist. In some aspects, provided herein is a method of treating, stabilizing or lessening the severity or progression of a NAFLD without substantially increasing the plasma triglyceride levels of the patient, wherein the method comprises administering to a patient in need thereof Compound 1 in combination with a PPARα agonist. In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar, muraglitzar and saroglitazar.

In some aspects, provided herein is a method of treating, stabilizing or lessening the severity or progression of a NAFLD while reducing or eliminating the occurrence or lessening the severity of hypertriglyceridemia, wherein the method comprises administering to a patient in need thereof Compound 1 in combination with fish oil, e.g., icosapent ethyl (Vascepa®). In some aspects, provided herein is a method of treating, stabilizing or lessening the severity or progression of a NAFLD without substantially increasing the plasma triglyceride levels of the patient, wherein the method comprises administering to a patient in need thereof Compound 1 in combination with fish oil, e.g., icosapent ethyl (Vascepa®).

In some aspects, provided is a method of treating, stabilizing or lessening the severity or progression of a non-alcoholic fatty liver disease (NAFLD), which method comprises administering to a patient in need thereof Compound 2 in combination with a PPARα agonist. In some embodiments, provided is a method of treating, stabilizing, or lessening the severity or progression of a non-alcoholic fatty liver disease, wherein the method comprises administering to a patient in need thereof Compound 2 in combination with a PPARα agonist, wherein the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar, and muraglitzar.

In some aspects, provided is a method of treating, stabilizing or lessening the severity or progression of a non-alcoholic fatty liver disease (NAFLD), which method comprises administering to a patient in need thereof Compound 2 in combination with fish oil.

In some aspects, provided herein is a method of treating, stabilizing or lessening the severity or progression of a NAFLD while reducing or eliminating the occurrence or lessening the severity of hypertriglyceridemia, wherein the method comprises administering to a patient in need thereof Compound 2 in combination with a PPARα agonist. In some aspects, provided herein is a method of treating, stabilizing or lessening the severity or progression of a NAFLD without substantially increasing the plasma triglyceride levels of the patient, wherein the method comprises administering to a patient in need thereof Compound 2 in combination with a PPARα agonist. In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar, muraglitzar and saroglitazar.

In some aspects, provided herein is a method of treating, stabilizing or lessening the severity or progression of a NAFLD while reducing or eliminating the occurrence or lessening the severity of hypertriglyceridemia, wherein the method comprises administering to a patient in need thereof Compound 2 in combination with fish oil, e.g., icosapent ethyl (Vascepa®). In some aspects, provided herein is a method of treating, stabilizing or lessening the severity or progression of a NAFLD without substantially increasing the plasma triglyceride levels of the patient, wherein the method comprises administering to a patient in need thereof Compound 2 in combination with fish oil, e.g., icosapent ethyl (Vascepa®).

In some embodiments, the NAFLD is steatosis. In some embodiments, the NAFLD is non-alcoholic steatohepatitis (NASH). In some embodiments, the NAFLD is liver fibrosis caused by NASH. In some embodiments, the NAFLD is liver cirrhosis caused by NASH. In some embodiments, the NAFLD is hepatocellular carcinoma (HCC) caused by NASH.

In some aspects, provided herein is a method of treating, stabilizing or lessening the severity or progression of liver fibrosis caused by NASH, wherein the method comprises administering to a patient in need thereof an ACC inhibitor in combination with a PPARα agonist. In some embodiments, the ACC inhibitor is Compound 1 or Compound 2. In some embodiments, the PPARα agonist is selected from the group consisting of fish oil, aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar and muraglitzar.

In some aspects, provided herein is a method of treating, stabilizing or lessening the severity or progression of a non-alcoholic steatohepatitis (NASH), wherein the method comprises administering to a patient in need thereof an ACC inhibitor in combination with a PPARα agonist. In some aspects, provided herein is a method of treating, stabilizing or lessening the severity or progression of a non-alcoholic steatohepatitis (NASH), wherein the method comprises administering to a patient in need thereof an ACC inhibitor in combination with a PPARα agonist, wherein the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar and muraglitzar.

In some aspects, provided herein is a method of treating, stabilizing or lessening the severity or progression of a non-alcoholic steatohepatitis (NASH), wherein the method comprises administering to a patient in need thereof an ACC inhibitor in combination with fish oil, e.g., icosapent ethyl (Vascepa®).

In some aspects, provided herein is a method of treating, stabilizing or lessening the severity or progression of a non-alcoholic steatohepatitis (NASH), wherein the method comprises administering to a patient in need thereof Compound 1 in combination with a PPARα agonist. In some aspects, provided herein is a method of treating, stabilizing or lessening the severity or progression of a non-alcoholic steatohepatitis (NASH), wherein the method comprises administering to a patient in need thereof Compound 1 in combination with a PPARα agonist, wherein the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar and muraglitzar.

In some aspects, provided herein is a method of treating, stabilizing or lessening the severity or progression of a non-alcoholic steatohepatitis (NASH), wherein the method comprises administering to a patient in need thereof Compound 1 in combination with fish oil, e.g., icosapent ethyl (Vascepa®).

In some aspects, provided herein is a method of treating, stabilizing or lessening the severity or progression of a non-alcoholic steatohepatitis (NASH), wherein the method comprises administering to a patient in need thereof Compound 2 in combination with a PPARα agonist. In some aspects, provided herein is a method of treating, stabilizing or lessening the severity or progression of a non-alcoholic steatohepatitis (NASH), wherein the method comprises administering to a patient in need thereof Compound 2 in combination with a PPARα agonist, wherein the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar and muraglitzar.

In some aspects, provided herein is a method of treating, stabilizing or lessening the severity or progression of a non-alcoholic steatohepatitis (NASH), wherein the method comprises administering to a patient in need thereof Compound 2 in combination with fish oil, e.g., icosapent ethyl (Vascepa®).

In some embodiments, the patient is non-cirrhotic.

In some embodiments, the patient has stage 1 to 4 fibrosis by historical liver biopsy.
    stage 1: enlargement of the portal areas by fibrosis;
    stage 2: fibrosis extending out from the portal areas with rare bridges between portal areas;
    stage 3: many bridges of fibrosis that link up portal and central areas of the liver
    stage 4: definite cirrhosis with <50% of biopsy fibrosis.

In some embodiments, the patient has a magnetic resonance imaging proton density fat fraction (MRI-PDFF) of at least about 8% at baseline (prior to treatment with an ACC inhibitor). In some embodiments, the patient has a MRI-PDFF of at least about 11% at baseline.

In some embodiments, the patient has a magnetic resonance imaging proton density fat fraction (MRI-PDFF) of at least about 8% at baseline (prior to treatment with Compound 1). In some embodiments, the patient has a MRI-PDFF of at least about 11% at baseline.

In some embodiments, the patient has a magnetic resonance imaging proton density fat fraction (MRI-PDFF) of at least about 8% at baseline (prior to treatment with Compound 2). In some embodiments, the patient has a MRI-PDFF of at least about 11% at baseline.

In some embodiments, the patient has a liver stiffness of at least about 2.5 kPa at baseline (prior to treatment with an ACC inhibitor). In some embodiments, the patient has a liver stiffness of at least about 2.9 kPa at baseline.

In some embodiments, the patient has a liver stiffness of at least about 2.5 kPa at baseline (prior to treatment with Compound 1). In some embodiments, the patient has a liver stiffness of at least about 2.9 kPa at baseline.

In some embodiments, the patient has a liver stiffness of at least about 2.5 kPa at baseline (prior to treatment with Compound 2). In some embodiments, the patient has a liver stiffness of at least about 2.9 kPa at baseline.

In some embodiments, the patient has elevated serum levels of ALT, TIMP-1 and/or PIII-NP at baseline as compared to normal.

In some embodiments, the treatment reduces the MRI-PDFF of the patient by at least about 20% as compared to baseline. In some embodiments, the treatment reduces the MRI-PDFF of the patient by at least about 25% as compared to baseline. In some embodiments, the treatment reduces the MRI-PDFF of the patient by at least about 30% as compared to baseline.

In some embodiments, at least about 1 in 3 of the treated patients achieve an about 30% of reduction of MRI-PDFF as compared to baseline. In some embodiments, about 1 in 2 of the treated patients achieve an about 30% of reduction of MRI-PDFF as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment with an ACC inhibitor). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment with Compound 1). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment with Compound 2). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of N-terminal procollagen III-peptide (PIII-NP) of the patient by at least about 9% as compared to baseline (the serum levels of PIII-NP prior to treatment with an ACC inhibitor). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some embodiments, the treatment reduces the serum levels of N-terminal procollagen III-peptide (PIII-NP) of the patient by at least about 9% as compared to baseline (the serum levels of PIII-NP prior to treatment with Compound 1). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some embodiments, the treatment reduces the serum levels of N-terminal procollagen III-peptide (PIII-NP) of the patient by at least about 9% as compared to baseline (the serum levels of PIII-NP prior to treatment with Compound 2). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some aspects, provided herein is a method of treating, stabilizing or lessening the severity or progression of a NASH while reducing or eliminating the occurrence or lessening the severity of hypertriglyceridemia, wherein the method comprises administering to a patient in need thereof an ACC inhibitor in combination with a PPARα agonist. In some aspects, provided herein is a method of treating, stabilizing or lessening the severity or progression of a NASH without substantially increasing the plasma triglyceride levels of the patient, wherein the method comprises administering to a patient in need thereof an ACC inhibitor in combination with a PPARα agonist. In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), GW409544, AZ 242, LY518674, NS-220, AVE8134, BMS-711939, aleglitazar, muraglitzar and saroglitazar.

In some aspects, provided herein is a method of treating, stabilizing or lessening the severity or progression of a NASH while reducing or eliminating the occurrence or lessening the severity of hypertriglyceridemia, wherein the method comprises administering to a patient in need thereof an ACC inhibitor in combination with fish oil, e.g., icosapent ethyl (Vascepa®). In some aspects, provided herein is a method of treating, stabilizing or lessening the severity or progression of a NASH without substantially increasing the plasma triglyceride levels of the patient, wherein the method comprises administering to a patient in need thereof an ACC inhibitor in combination with fish oil, e.g., icosapent ethyl (Vascepa®).

In some aspects, provided herein is a method of treating, stabilizing or lessening the severity or progression of a NASH while reducing or eliminating the occurrence or lessening the severity of hypertriglyceridemia, wherein the method comprises administering to a patient in need thereof Compound 1 in combination with a PPARα agonist. In some aspects, provided herein is a method of treating, stabilizing or lessening the severity or progression of a NASH without substantially increasing the plasma triglyceride levels of the patient, wherein the method comprises administering to a patient in need thereof Compound 1 in combination with a PPARα agonist. In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), GW409544, AZ 242, LY518674, NS-220, AVE8134, BMS-711939, aleglitazar, muraglitzar and saroglitazar.

In some aspects, provided herein is a method of treating, stabilizing or lessening the severity or progression of a NASH while reducing or eliminating the occurrence or lessening the severity of hypertriglyceridemia, wherein the method comprises administering to a patient in need thereof Compound 1 in combination with fish oil, e.g., icosapent ethyl (Vascepa®). In some aspects, provided herein is a method of treating, stabilizing or lessening the severity or progression of a NASH without substantially increasing the plasma triglyceride levels of the patient, wherein the method comprises administering to a patient in need thereof Compound 1 in combination with fish oil, e.g., icosapent ethyl (Vascepa®).

In some aspects, provided herein is a method of treating, stabilizing or lessening the severity or progression of a NASH while reducing or eliminating the occurrence or lessening the severity of hypertriglyceridemia, wherein the method comprises administering to a patient in need thereof Compound 2 in combination with a PPARα agonist. In some aspects, provided herein is a method of treating, stabilizing or lessening the severity or progression of a NASH without substantially increasing the plasma triglyceride levels of the patient, wherein the method comprises administering to a patient in need thereof Compound 2 in combination with a PPARα agonist. In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), GW409544, AZ 242, LY518674, NS-220, AVE8134, BMS-711939, aleglitazar, muraglitzar and saroglitazar.

In some aspects, provided herein is a method of treating, stabilizing or lessening the severity or progression of a NASH while reducing or eliminating the occurrence or lessening the severity of hypertriglyceridemia, wherein the method comprises administering to a patient in need thereof Compound 2 in combination with fish oil, e.g., icosapent ethyl (Vascepa®). In some aspects, provided herein is a method of treating, stabilizing or lessening the severity or progression of a NASH without substantially increasing the plasma triglyceride levels of the patient, wherein the method comprises administering to a patient in need thereof Compound 2 in combination with fish oil, e.g., icosapent ethyl (Vascepa®).

In some embodiments, the patient is non-cirrhotic. In some embodiments, the patient has a magnetic resonance imaging proton density fat fraction (MRI-PDFF) of at least about 8% at baseline (prior to treatment with an ACC inhibitor). In some embodiments, the patient has a MRI-PDFF of at least about 11% at baseline.

In some embodiments, the patient is non-cirrhotic. In some embodiments, the patient has a magnetic resonance imaging proton density fat fraction (MRI-PDFF) of at least about 8% at baseline (prior to treatment with Compound 1). In some embodiments, the patient has a MRI-PDFF of at least about 11% at baseline.

In some embodiments, the patient is non-cirrhotic. In some embodiments, the patient has a magnetic resonance imaging proton density fat fraction (MRI-PDFF) of at least about 8% at baseline (prior to treatment with Compound 2). In some embodiments, the patient has a MRI-PDFF of at least about 11% at baseline.

In some embodiments, the patient has a liver stiffness of at least about 2.5 kPa at baseline (prior to treatment with an ACC inhibitor). In some embodiments, the patient has a liver stiffness of at least about 2.9 kPa at baseline.

In some embodiments, the patient has a liver stiffness of at least about 2.5 kPa at baseline (prior to treatment with Compound 1). In some embodiments, the patient has a liver stiffness of at least about 2.9 kPa at baseline.

In some embodiments, the patient has a liver stiffness of at least about 2.5 kPa at baseline (prior to treatment with Compound 2). In some embodiments, the patient has a liver stiffness of at least about 2.9 kPa at baseline.

In some embodiments, the patient has a normal plasma triglyceride level of below about 150 milligrams per deciliter (mg/dL) at baseline (prior to treatment with an ACC inhibitor). In some embodiments, the patient has at least a borderline high plasma triglyceride level (about 150 mg/dL or more) at baseline. In some embodiments, the patient has at least a high plasma triglyceride level of about 500 mg/dL or more at baseline. In some embodiments, the patient has a borderline high plasma triglyceride level of from 150 mg/dL to 199 mg/dL. In some embodiments, the patient has a high plasma triglyceride level of from 200 mg/dL to 499 mg/dL. In some embodiments, the patient has a very high plasma triglyceride level of above 500 mg/dL. In some embodiments, the patient has a plasma triglyceride level of about 250 mg/dL at baseline.

In some embodiments, the patient has a plasma triglyceride level of below about 150 mg/dL at baseline (prior to treatment with Compound 1). In some embodiments, the patient has a plasma triglyceride level of at least about 150 mg/dL at baseline. In some embodiments, the patient has a plasma triglyceride level of at least about 200 mg/dL at baseline. In some embodiments, the patient has a plasma triglyceride level of at least about 250 mg/dL at baseline.

In some embodiments, the patient has a plasma triglyceride level of below about 100 mg/dL at baseline (prior to treatment with Compound 2). In some embodiments, the patient has a plasma triglyceride level of at least about 150 mg/dL at baseline. In some embodiments, the patient has a plasma triglyceride level of at least about 200 mg/dL at baseline. In some embodiments, the patient has a plasma triglyceride level of at least about 250 mg/dL at baseline.

In some embodiments, provided herein is a method of treating, stabilizing or lessening the severity or progression of a NASH in a patient having NASH and a plasma triglyceride level of below about 150 mg/dL without substantially increasing the triglyceride level of the patient, wherein the method comprises administering to a patient in need thereof an ACC inhibitor in combination with a PPARα agonist. In some embodiments, provided herein is a method of treating, stabilizing or lessening the severity or progression of a NASH in a patient having NASH and a plasma triglyceride level of below about 150 mg/dL without substantially increasing the triglyceride level of the patient, wherein the method comprises administering to a patient in need thereof an ACC inhibitor in combination with fish oil, e.g., icosapent ethyl (Vascepa®). In some embodiments, the patient has a plasma triglyceride level of at least about 150 mg/dL at baseline. In some embodiments, the patient has a plasma triglyceride level of at least about 200 mg/dL at baseline. In some embodiments, the patient has a plasma triglyceride level of at least about 250 mg/dL at baseline.

In some embodiments, provided herein is a method of treating, stabilizing or lessening the severity or progression of a NASH in a patient having NASH and a plasma triglyceride level of at least about 150 mg/dL without substantially increasing the triglyceride level of the patient, wherein the method comprises administering to a patient in need thereof Compound 1 in combination with a PPARα agonist. In some embodiments, provided herein is a method of treating, stabilizing or lessening the severity or progression of a NASH in a patient having NASH and a plasma triglyceride level of at least about 150 mg/dL without substantially increasing the triglyceride level of the patient, wherein the method comprises administering to a patient in need thereof Compound 1 in combination with fish oil, e.g., icosapent ethyl (Vascepa®). In some embodiments, the patient has a plasma triglyceride level of at least about 200 mg/dL at baseline. In some embodiments, the patient has a plasma triglyceride level of at least about 250 mg/dL at baseline.

In some embodiments, provided herein is a method of treating, stabilizing or lessening the severity or progression of a NASH in a patient having NASH and a plasma triglyceride level of at least about 150 mg/dL without substantially increasing the triglyceride level of the patient, wherein the method comprises administering to a patient in need thereof Compound 2 in combination with a PPARα agonist. In some embodiments, provided herein is a method of treating, stabilizing or lessening the severity or progression of a NASH in a patient having NASH and a plasma triglyceride level of at least about 150 mg/dL without substantially increasing the triglyceride level of the patient, wherein the method comprises administering to a patient in need thereof Compound 2 in combination with fish oil, e.g., icosapent ethyl (Vascepa®). In some embodiments, the patient has a plasma triglyceride level of at least about 200 mg/dL at baseline. In some embodiments, the patient has a plasma triglyceride level of at least about 250 mg/dL at baseline.

In some embodiments, the patient has elevated serum levels of ALT, TIMP-1 and/or PIII-NP at baseline as compared to normal.

In some embodiments, the treatment reduces the MRI-PDFF of the patient by at least about 20% as compared to baseline. In some embodiments, the treatment reduces the MRI-PDFF of the patient by at least about 25% as compared to baseline. In some embodiments, the treatment reduces the MRI-PDFF of the patient by at least about 30% as compared to baseline.

In some embodiments, at least about 1 in 3 of the treated patients achieve an about 30% of reduction of MRI-PDFF as compared to baseline. In some embodiments, about 1 in 2 of the treated patients achieve an about 30% of reduction of MRI-PDFF as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment with an ACC inhibitor). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment with Compound 1). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment with Compound 2). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of N-terminal procollagen III-peptide (PIII-NP) of the patient by at least about 9% as compared to baseline (the serum levels of PIII-NP prior to treatment with an ACC inhibitor). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some embodiments, the treatment reduces the serum levels of N-terminal procollagen III-peptide (PIII-NP) of the patient by at least about 9% as compared to baseline (the serum levels of PIII-NP prior to treatment with Compound 1). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some embodiments, the treatment reduces the serum levels of N-terminal procollagen III-peptide (PIII-NP) of the patient by at least about 9% as compared to baseline (the serum levels of PIII-NP prior to treatment with Compound 2). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some embodiments, the triglyceride level of the treated patient is not significantly increased during the treatment. In some embodiments, the triglyceride level of the treated patient is not increased more than about 10% from the baseline during treatment. In some embodiments, the triglyceride level of the treated patient is not increased more than about 5% from the baseline during treatment. In some embodiments, the triglyceride level of the treated patient is not increased more than about 1% from the baseline during treatment. In some embodiments, the triglyceride level of the treated patient remains substantially the same upon treatment, e.g., remains at about ±10% of baseline or about ±5% of baseline.

In some embodiments, the treated patient does not experience a Grade 3 or 4 triglyceride elevation.

In some embodiments, the PPARα agonist is selected from the group consisting of aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (e.g., icosapent ethyl (Vascepa®), or docosahexaenoic acid), pirinixic acid, GW409544, AZ 242, LY518674, NS-220, AVE8134, BMS-711939, aleglitazar, muraglitzar and saroglitazar. In some embodiments, the PPARα agonist is fenofibrate.

In some embodiments, the ACC inhibitor (e.g., Compound 1 or Compound 2) is administered in a therapeutically effective amount. In some embodiments, the PPARα agonist or fish oil is administered in a therapeutically effective amount. In some embodiments, the ACC inhibitor (e.g., Compound 1 or Compound 2) and the PPARα agonist or fish oil are administered in a therapeutically effective amount.

It is contemplated that the combination of an ACC inhibitor, such as Compound 1 or Compound 2, and the PPARα agonist (such as fish oil) improve markers of NASH, including but not limited to (e.g., ALT, AST, GGT, ELF, hyaluronic acid, TIMP1, PIIINP, TG, MRI-PDFF, MRE, and Fibroscan). It is further contemplated that patients on a PPARα agonist (such as fish oil) at baseline exhibit an improvement in metabolic parameters (such as decreases in triglycerides) when an ACC inhibitor is administered.

In some aspects, provided herein is a method of treating a non-alcoholic steatohepatitis in a non-cirrhotic patient with a non-alcoholic steatohepatitis, wherein the method comprises administering to the patient in need thereof about 20 mg of an ACC inhibitor once daily.

In some aspects, provided herein is a method of treating a non-alcoholic steatohepatitis in a non-cirrhotic patient with a non-alcoholic steatohepatitis, wherein the method comprises administering to the patient in need thereof about 20 mg of Compound 1 once daily.

In some aspects, provided herein is a method of treating a non-alcoholic steatohepatitis in a non-cirrhotic patient with a non-alcoholic steatohepatitis, wherein the method comprises administering to the patient in need thereof about 20 mg of Compound 2 once daily.

In some aspects, provided herein are methods of treating non-alcoholic steatohepatitis (NASH) in a patient with compensated cirrhosis due to NASH. In some aspects, such methods comprise administration of an ACC inhibitor including, without limitation, Compound 1 and Compound 2. The administration can be once daily, and the daily dose, without limitation, may be 20 mg.

In some aspects, provided herein is a method of treating non-alcoholic steatohepatitis (NASH) in a patient with compensated cirrhosis due to NASH, wherein the method comprises administering to the patient in need thereof about 20 mg of an ACC inhibitor once daily.

In some aspects, provided herein is a method of treating non-alcoholic steatohepatitis (NASH) in a patient with compensated cirrhosis due to NASH, wherein the method comprises administering to the patient in need thereof about 20 mg of Compound 1 once daily.

In some aspects, provided herein is a method of treating non-alcoholic steatohepatitis (NASH) in a patient with compensated cirrhosis due to NASH, wherein the method comprises administering to the patient in need thereof about 20 mg of Compound 2 once daily.

In some aspects, provided herein are methods of improving hepatic steatosis in a patient with compensated cirhosis due to NASH. In some aspects, provided herein are methods of improving hepatic steatosis in a non-cirrhotic patient with NASH.

In some embodiments, the patient has a magnetic resonance imaging proton density fat fraction (MRI-PDFF) of at least about 8% at baseline (prior to treatment with Compound an ACC inhibitor). In some embodiments, the patient has a MRI-PDFF of at least about 11% at baseline.

In some embodiments, the patient has a magnetic resonance imaging proton density fat fraction (MRI-PDFF) of at least about 8% at baseline (prior to treatment with Compound 1). In some embodiments, the patient has a MRI-PDFF of at least about 11% at baseline.

In some embodiments, the patient has a magnetic resonance imaging proton density fat fraction (MRI-PDFF) of at least about 8% at baseline (prior to treatment with Compound 2). In some embodiments, the patient has a MRI-PDFF of at least about 11% at baseline.

In some embodiments, the patient has a liver stiffness of at least about 2.5 kPa at baseline (prior to treatment with an ACC inhibitor). In some embodiments, the patient has a liver stiffness of at least about 2.9 kPa at baseline.

In some embodiments, the patient has a liver stiffness of at least about 2.5 kPa at baseline (prior to treatment with Compound 1). In some embodiments, the patient has a liver stiffness of at least about 2.9 kPa at baseline.

In some embodiments, the patient has a liver stiffness of at least about 2.5 kPa at baseline (prior to treatment with Compound 2). In some embodiments, the patient has a liver stiffness of at least about 2.9 kPa at baseline.

In some embodiments, the patient has a baseline plasma triglyceride level of below about 250 mg/dL. In some embodiments, the patient has a baseline plasma triglyceride level of below about 200 mg/dL. In some embodiments, the patient has a baseline plasma triglyceride level of below about 150 mg/dL.

In some embodiments, the treatment reduces the magnetic resonance imaging proton density fat fraction (MRI-PDFF) of the patient by at least about 20% as compared to baseline. In some embodiments, the treatment reduces the MRI-PDFF of the patient by at least about 25% as compared to baseline. In some embodiments, the treatment reduces the MRI-PDFF of the patient by at least about 30% as compared to baseline.

In some embodiments, at least about 1 in 3 of the patients treated with an ACC inhibitor achieve an about 30% of reduction of MRI-PDFF as compared to baseline. In some embodiments, about 1 in 2 of the patients treated with an ACC inhibitor achieve an about 30% of reduction of MRI-PDFF as compared to baseline.

In some embodiments, at least about 1 in 3 of the patients treated with Compound 1 achieve an about 30% of reduction of MRI-PDFF as compared to baseline. In some embodiments, about 1 in 2 of the patients treated with Compound 1 achieve an about 30% of reduction of MRI-PDFF as compared to baseline.

In some embodiments, at least about 1 in 3 of the patients treated with Compound 2 achieve an about 30% of reduction of MRI-PDFF as compared to baseline. In some embodiments, about 1 in 2 of the patients treated with Compound 2 achieve an about 30% of reduction of MRI-PDFF as compared to baseline.

In some embodiments, the treatment reduces the serum levels of tissue inhibitor of metalloproteinases-1 (TIMP-1) of the patient by at least about 5% as compared to baseline (the serum levels of TIMP-1 prior to treatment). In some embodiments, the treatment reduces the serum levels of TIMP-1 of the patient by at least about 6% as compared to baseline. In some embodiments, the treatment reduces the serum levels of TIMP-1 of the patient by at least about 7% as compared to baseline.

In some embodiments, the treatment reduces the serum levels of N-terminal procollagen III-peptide (PIII-NP) of the patient by at least about 9% as compared to baseline (the serum levels of PIII-NP prior to treatment). In some embodiments, the treatment reduces the serum levels of PIII-NP of the patient by at least about 10% as compared to baseline. In some embodiments, the treatment reduces the serum levels of PIII-NP of the patient by at least about 13% as compared to baseline.

In some embodiments, the method further comprises administering to the patient a PPARα agonist or fish oil.

In some embodiments, provided is a method of reducing hepatic diacylglyceride levels in a patient in need thereof having elevated hepatic diacylglyceride levels, wherein the method comprises administering an therapeutically effective amount of an ACC inhibitor to the patient.

In some embodiments, provided is method of restoring hepatic membrane lipids in a patient in need thereof, wherein the method comprises administering an therapeutically effective amount of an ACC inhibitor to the patient.

In some embodiments, provided is a method of increasing hepatic phosphatidylethanolamine in a patient in need thereof having reduced hepatic phosphatidylethanolamine levels, wherein the method comprises administering an therapeutically effective amount of an ACC inhibitor to the patient.

In some embodiments, provided is a method of increasing hepatic phosphatidylcoline in a patient in need thereof having reduced hepatic phosphatidylcoline levels, wherein the method comprises administering an therapeutically effective amount of an ACC inhibitor to the patient.

In some embodiments, provided is a method of reducing a substrate of bile acid synthesis in a patient in need thereof, wherein the method comprises administering an therapeutically effective amount of an ACC inhibitor to the patient.

In some embodiments, provided is a method of treating NASH in a patient having an elevated level of one or more of Col1a1, palmitoleate, isobutyrylcarnitine, 3-hydroxybutyrate, or 3-hydroxybutyrylcarnitine, wherein the method comprises administering an therapeutically effective amount of an ACC inhibitor to the patient.

In some embodiments, an ACC inhibitor is administered in an amount of about 10 mg, about 15 mg, about 20 mg, about 25 mg, about 30 mg, or about 35 mg daily. In some embodiments, an ACC inhibitor is administered once, twice or three times a day. In some embodiments, an ACC inhibitor is administered in an amount of about 10 mg, about 15 mg, about 20 mg, about 25 mg, about 30 mg, or about 35 mg once daily.

In some embodiments, Compound 1 is administered in an amount of about 10 mg, about 15 mg, about 20 mg, about 25 mg, about 30 mg, or about 35 mg daily. In some embodiments, Compound 1 is administered once, twice or three times a day. In some embodiments, Compound 1 is administered in an amount of about 10 mg, about 15 mg, about 20 mg, about 25 mg, about 30 mg, or about 35 mg once daily. In some embodiments, Compound 1 is administered in an amount of about 20 mg once daily. In some embodiments, Compound 1 is administered as the free acid (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid in an amount of about 20 mg once daily. In some embodiments, Compound 1 is administered as a pharmaceutically acceptable salt, solvate, hydrate or co-crystal of (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid once daily in an amount that is equivalent to about 20 mg of (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid free acid.

In some embodiments, Compound 2 is administered in an amount of about 10 mg, about 15 mg, about 20 mg, about 25 mg, about 30 mg, or about 35 mg daily. In some embodiments, Compound 2 is administered once, twice or three times a day. In some embodiments, Compound 2 is administered in an amount of about 10 mg, about 15 mg, about 20 mg, about 25 mg, about 30 mg, or about 35 mg once daily. In some embodiments, Compound 2 is administered in an amount of about 20 mg once daily. In some embodiments, Compound 2 is administered as the free acid 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid in an amount of about 20 mg once daily. In some embodiments, Compound 2 is administered as a pharmaceutically acceptable salt, solvate, hydrate or co-crystal of 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid once daily in an amount that is equivalent to about 20 mg of 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid free acid.

In some embodiments, an ACC inhibitor is administered in a unit dosage formulation that comprises the ACC inhibitor in an amount equivalent to about 10 mg, 20 mg, or 30 mg of the free acid of the ACC inhibitor. In certain embodiments, a capsule formulation provides an ACC inhibitor in an amount equivalent to about 10 mg, about 15 mg, about 20 mg, about 25 mg, about 30 mg, or about 35 mg of the free acid of the ACC inhibitor.

In some embodiments, Compound 1 is administered in a unit dosage formulation that comprises Compound 1 in an amount equivalent to about 10 mg, 20 mg, or 30 mg of Compound 1 free acid. In certain embodiments, a capsule formulation provides Compound 1 in an amount equivalent to about 10 mg, about 15 mg, about 20 mg, about 25 mg, about 30 mg, or about 35 mg of Compound 1 free acid.

In some embodiments, Compound 2 is administered in a unit dosage formulation that comprises Compound 2 in an amount equivalent to about 10 mg, 20 mg, or 30 mg of Compound 2 free acid. In certain embodiments, a capsule formulation provides Compound 2 in an amount equivalent to about 10 mg, about 15 mg, about 20 mg, about 25 mg, about 30 mg, or about 35 mg of Compound 2 free acid.

In some embodiments, the once daily ACC inhibitor is administered in the evening, such as at or after about 6 p.m., about 7 p.m., about 8 p.m. or about 9 p.m. local time.

In some embodiments, the once daily Compound 1 is administered in the evening, such as at or after about 6 p.m., about 7 p.m., about 8 p.m. or about 9 p.m. local time.

In some embodiments, the once daily Compound 2 is administered in the evening, such as at or after about 6 p.m., about 7 p.m., about 8 p.m. or about 9 p.m. local time.

In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

Compound 1

Compound 1 is an ACC inhibitor having the chemical name (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid and the structure:

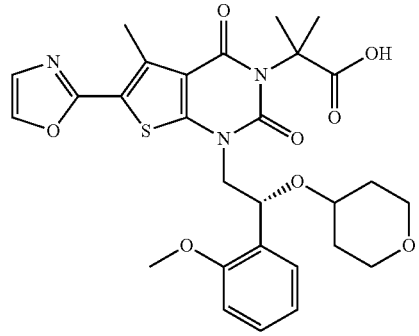 [SMILES: COc1ccccc1[C@H](Cn1c(=O)n(C(C)(C)C(=O)O)c(=O)c2c(C)c(-c3ncco3)sc21)OC1CCOCC1]

or a pharmaceutically acceptable salt, a co-crystal, a solvate, or a hydrate thereof. In some embodiments, Compound 1 is (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid, which is also referred to as Compound 1 free acid. In some embodiments, Compound 1 is a pharmaceutically acceptable salt of (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid. In some embodiments, a deuterated analog of Compound 1 may be used in the methods described herein.

Examples of pharmaceutically acceptable salts include salts derived from appropriate bases include metal ions (e.g., aluminum, zinc, alkali metals, alkaline earth metals), ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, those derived from nontoxic ammonium, quaternary ammonium, and primary, secondary or tertiary amine cations, including but not limited to those derived from natural or non-naturally-occurring amino acids. Representative amine or ammonium-based salts include but are not limited to those derived from arginine, betaine, hydrabamine, choline, diethylamine, lysine, benzathine, 2-(diethylamino)-ethanol, ethanolamine, 1-(2-hydroxyethyl)-pyrrolidine, diethanolamine, ammonia, deanol, N-methyl-glucamine, tromethamine, triethanolamine, 4-(2-hydroxyethyl)-morpholine, 1H-imidazole, ethylenediamine, piperazine, procaine, and benethamine.

In some embodiments, Compound 1 is in a crystalline form. Certain crystalline forms of Compound 1 are described in U.S. Patent Application Publication US 2017/0267690 A1, which is hereby incorporated by reference in its entirety. In some embodiments, the crystalline form of Compound 1 is "Compound 1 Form I," "Compound 1 Form II," "Compound 1 Form III," "Compound 1 Form IV," "Compound 1 Form V," "Compound 1 Form VI," "Compound 1 Form VII," "Compound 1 Form VIII" as described in US 2017/0267690 A1.

In some embodiments, Compound 1 is "Compound 1 Sodium Form I," "Compound 1 Sodium Form II," "Compound 1 Calcium Form I," "Compound 1 Magnesium Form I," "Compound 1 Diethanolamine Form I," or "Compound 1 Piperazine Form I," as described in US 2017/0267690 A1.

In some embodiments, the crystalline form of Compound 1 is Compound 1 Form I characterized by an X-ray powder diffractogram comprising the following peaks: 9.3, 15.0, and 19.8 °2θ±0.2 °2θ, as determined on a diffractometer using Cu-Kα radiation at a wavelength of 1.54 Å.

In some embodiments, Compound 1 Form I is characterized by a diffractogram comprising one or more additional peaks at 16.0, 24.0, 25.8, and 27.3 °2θ±0.2 °2θ.

In some embodiments, the crystalline form of Compound 1 is characterized in that it has one or more peaks in its powder X-ray diffraction pattern selected from those at about 9.2, about 15.8, about 19.6, about 24.0, about 25.6, about 28.6, and about 8.7 degrees 2θ.

In some embodiments, Compound 1 Form 1 is characterized by a differential scanning calorimetry (DSC) curve that comprises an endotherm between about 189° C. to about 193° C.

In some embodiments, the crystalline form of Compound 1 is at least about 85% of Form I.

In some embodiments, the crystalline form of Compound 1 or a pharmaceutically acceptable salt or co-crystal thereof, is selected from Compound 1 Form II, Compound 1 Form III, Compound 1 Form IV, Compound 1 Form V, Compound 1 Form VI, Compound 1 Form VII, Compound 1 Form VIII, Compound 1 Sodium Form I, Compound 1 Sodium Form II, Compound 1 Calcium Form I, Compound 1 Magnesium Form, I Compound 1 Diethanolamine Form I, and Compound 1 Piperazine Form I.

In some embodiments, Compound 1 is in an amorphous form. In some embodiments, Compound 1 is substantially free of crystalline Compound 1.

Compound 2

Compound 2 is an ACC inhibitor having the chemical name 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid and the structure:

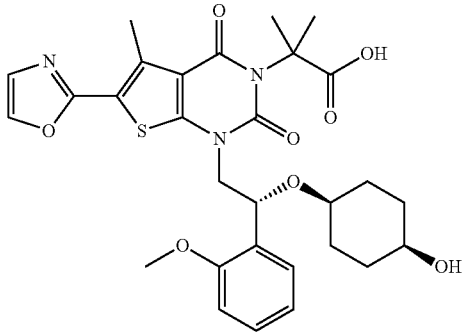 [SMILES: COc1ccccc1[C@H](Cn1c(=O)n(C(C)(C)C(=O)O)c(=O)c2c(C)c(-c3ncco3)sc21)O[C@H]1CC[C@@H](O)CC1]

or a pharmaceutically acceptable salt, a co-crystal, a solvate, or a hydrate thereof. In some embodiments, Compound 2 is 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid, which is also referred to as Compound 2 free acid. In some embodiments, Compound 2 is a pharmaceutically acceptable salt of 2-[1-[(2R)-2-[(4-hydroxycyclohexyl)oxy]-2-(2-methoxyphenyl)ethyl]-5-methyl-6-(1,3-oxazol-2-yl)-2,4-dioxo-1H,2H,3H,4H-thieno[2,3-d]pyrimidin-3-yl]-2-methylpropanoic acid. In some embodiments, a deuterated analog of Compound 2 may be used in the methods described herein.

PPARα Agonists

As described generally above, provided methods comprise combinations comprising an ACC inhibitor, e.g., Compound 1 or Compound 2, and a peroxisome proliferator-activated receptor alpha (PPARα) agonist.

Peroxisome proliferator-activated receptors (PPARs) are members of the nuclear receptor superfamily of ligand-activated transcription factors including three subtypes cloned from the mouse and human: PPARα, PPARγ, and PPARδ. PPARα, PPARγ, and PPARδ sequences are publicly available, for example from GenBank® sequence database. PPARα is also known as NR1C1 (nuclear receptor subfamily 1, group C, member 1). PPARα agonists activate PPARα.

In some embodiments, the PPARα agonist is not a mixed PPARα/δ agonist, such as GFT505. In some embodiments, the PPARα agonist is not a PPARα/γ dual agonist, such as saroglitazar. In some embodiments, the PPARα agonist is a selective PPARα agonist, such as a PPARα agonist having at least about 10 fold, about 20 fold, about 50 fold, or about 100 fold selectivity for PPARα against PPARγ and PPARδ. In some embodiments, the PPARα agonist is a selective PPARα agonist having an activity in activating human PPARα that is at least about 10 times, about 20 times, about 50 times, or about 100 times higher as compared to its activity in activating human PPARγ and PPARδ.

In some embodiments, the PPARα agonist is selected from:

| Name (alternative names or brand names) | Structure |
|---|---|
| Aluminum clofibrate (alfibrate) | 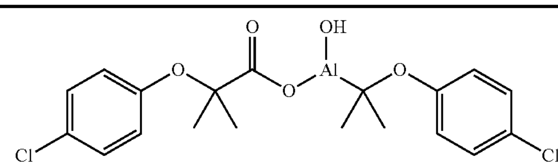 |

-continued

| Name (alternative names or brand names) | Structure |
|---|---|
| Bezafibrate (Bezalip) | 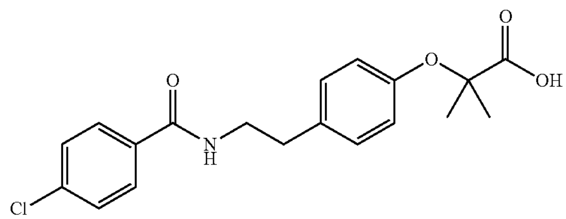 [SMILES: CC(C)(Oc1ccc(CCNC(=O)c2ccc(Cl)cc2)cc1)C(=O)O] |
| Ciprofibrate | 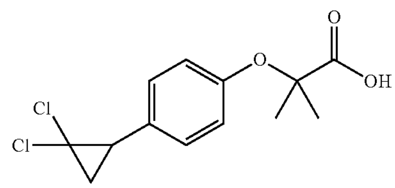 [SMILES: CC(C)(Oc1ccc(C2CC2(Cl)Cl)cc1)C(=O)O] |
| Choline fenofibrate | 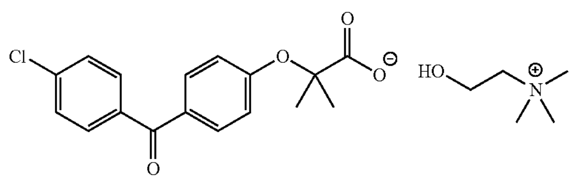 |
| Clinofibrate (Lipoclin ®) | 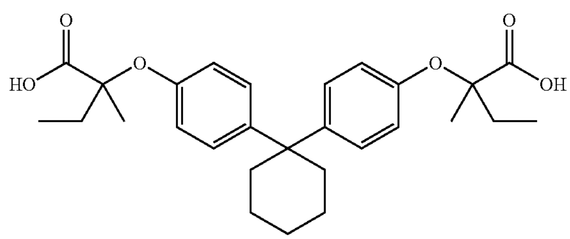 [SMILES: CCC(C)(Oc1ccc(C2(c3ccc(OC(C)(CC)C(=O)O)cc3)CCCCC2)cc1)C(=O)O] |
| Clofibrate (Atromid-S) | 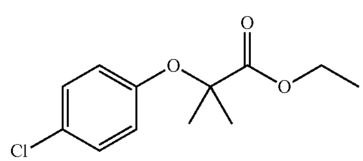 [SMILES: CCOC(=O)C(C)(C)Oc1ccc(Cl)cc1] |
| Clofibride (Lipenan ®) | 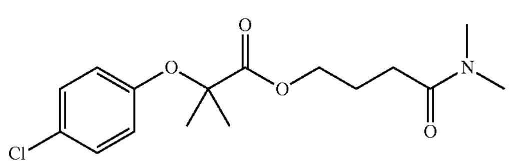 [SMILES: CN(C)C(=O)CCCOC(=O)C(C)(C)Oc1ccc(Cl)cc1] |
| Fenofibrate or a salt thereof (Antara ®, Fenoglide ®, Fibricor ®, Lipofen ®, Lofibra ®, Tricor ®, Triglide ®, Trilipix ®) | 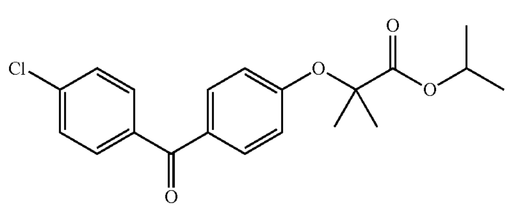 [SMILES: CC(C)OC(=O)C(C)(C)Oc1ccc(C(=O)c2ccc(Cl)cc2)cc1] |
| Gemfibrozil (Lopid ®) | 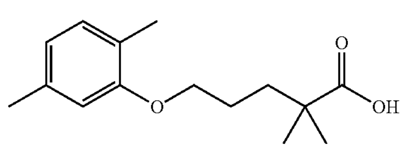 [SMILES: Cc1ccc(C)c(OCCCC(C)(C)C(=O)O)c1] |

-continued

| Name (alternative names or brand names) | Structure |
|---|---|
| Pemafibrate (K-877, K-13675, Parmodia ®) | 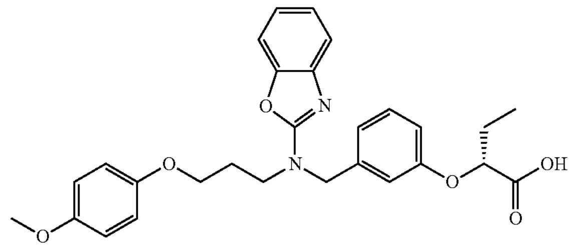 [SMILES: CC[C@@H](Oc1cccc(CN(CCCOc2ccc(OC)cc2)c2nc3ccccc3o2)c1)C(=O)O] |
| Ronifibrate | 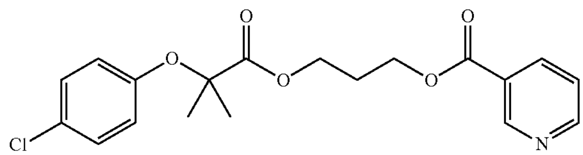 [SMILES: CC(C)(Oc1ccc(Cl)cc1)C(=O)OCCCOC(=O)c1cccnc1] |
| Simfibrate | 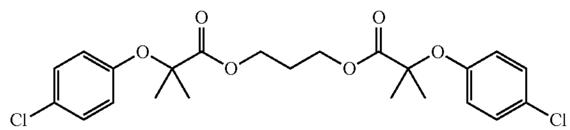 [SMILES: CC(C)(Oc1ccc(Cl)cc1)C(=O)OCCCOC(=O)C(C)(C)Oc1ccc(Cl)cc1] |
| AVE8134 | 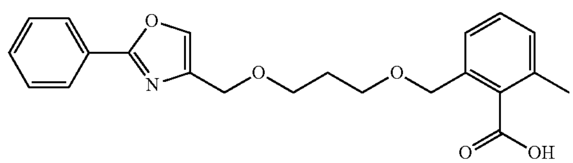 [SMILES: Cc1cccc(COCCCOCc2coc(-c3ccccc3)n2)c1C(=O)O] |
| pirinixic acid (WY-14,643) | 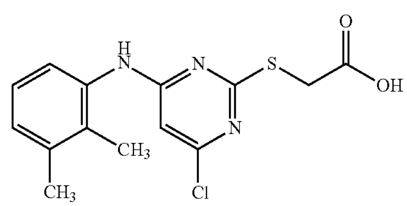 [SMILES: Cc1cccc(Nc2cc(Cl)nc(SCC(=O)O)n2)c1C] |
| BMS-711939 | 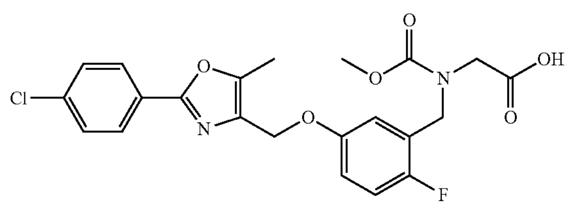 [SMILES: COC(=O)N(CC(=O)O)Cc1cc(OCc2nc(-c3ccc(Cl)cc3)oc2C)ccc1F] |
| 2-Methyl-c-5-[4-[5-methyl-2-(4-methylphenyl)-4-oxazolyl]butyl]-1,3-dioxane-r-2-carboxylic acid (NS-220) | 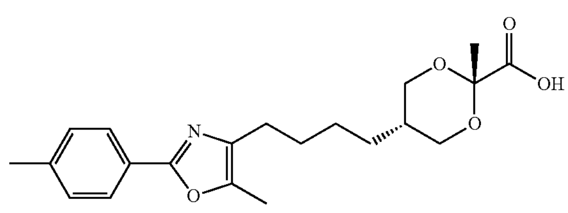 [SMILES: Cc1ccc(-c2nc(CCCC[C@H]3CO[C@@](C)(C(=O)O)OC3)c(C)o2)cc1] |
| aleglitazar | 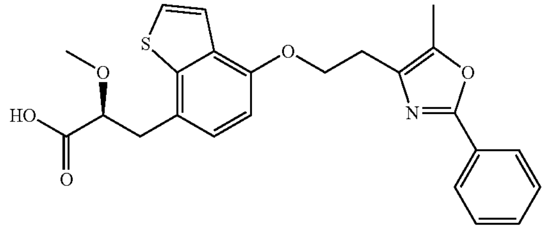 [SMILES: CO[C@@H](Cc1ccc(OCCc2nc(-c3ccccc3)oc2C)c2ccsc12)C(=O)O] |

| Name (alternative names or brand names) | Structure |
|---|---|
| muraglitazar | 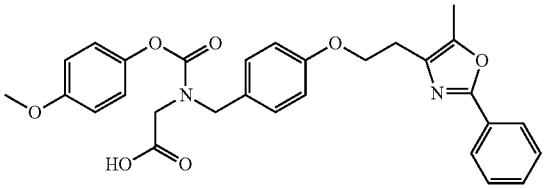 [SMILES: COc1ccc(OC(=O)N(CC(=O)O)Cc2ccc(OCCc3nc(-c4ccccc4)oc3C)cc2)cc1] |
| Saroglitazar (Lipaglyn ™) | 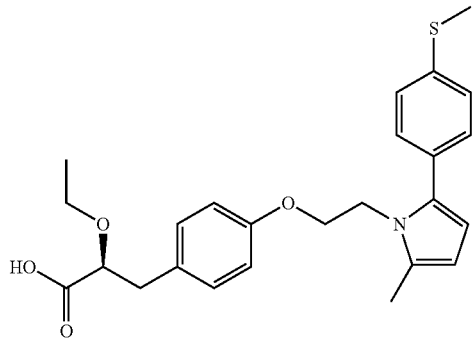 [SMILES: CCO[C@@H](Cc1ccc(OCCn2c(C)ccc2-c2ccc(SC)cc2)cc1)C(=O)O] |
| GW409544 | 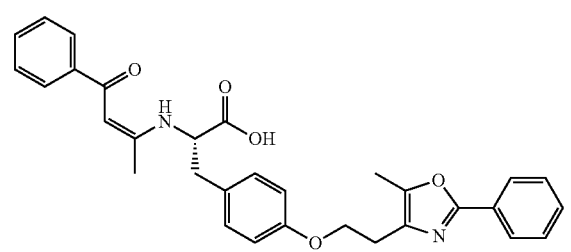 [SMILES: C/C(=C/C(=O)c1ccccc1)N[C@@H](Cc1ccc(OCCc2nc(-c3ccccc3)oc2C)cc1)C(=O)O] |
| AZ 242 | 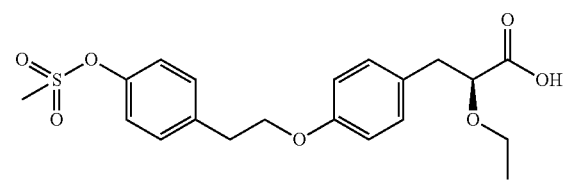 [SMILES: CCO[C@@H](Cc1ccc(OCCc2ccc(OS(C)(=O)=O)cc2)cc1)C(=O)O] |
| LY518674 | 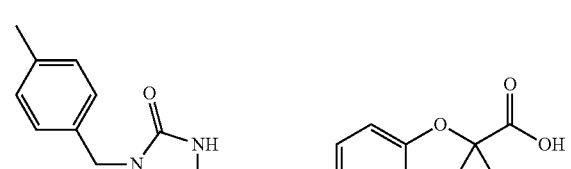 |

In some embodiments, the PPARα agonist is a fibrate, a carbozole based compound, or a piperidine based compound.

Fibrates are a class of compounds that are amphipathic carboxylic acids, including, e.g., aluminum clofibrate, bezafibrate, ciprofibrate, choline fenofibrate, clinofibrate, clofibrate, clofibride, fenofibrate, gemfibrozil, pemafibrate, ronifibrate, and simfibrate. Carbozole based PPARα agonists include, e.g., compounds described in U.S. Patent Application Publication No. 2010/0286210, such as:

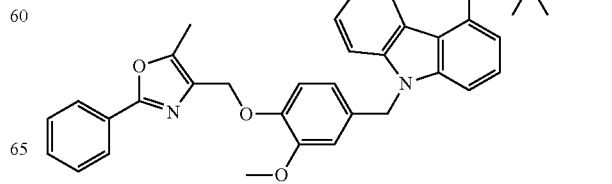

U.S. Patent Application Publication No. 2010/0286210 is hereby incorporated by reference in its entirety.

Piperidine based compounds include those described in Christopher D. Kane et al., *Molecular Pharmacology*, 2009, 75(2):296-306 (hereby incorporated by reference in its entirety), such as

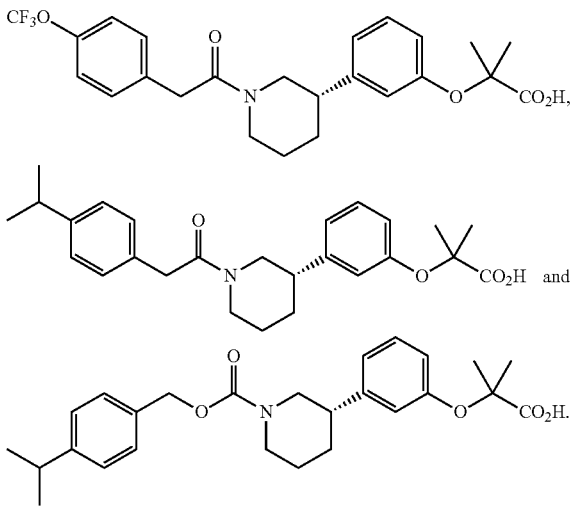

In some embodiments, the PPARα agonist is a compound described in International Patent application WO2017044551 (which is hereby incorporated by reference in its entirety), such as

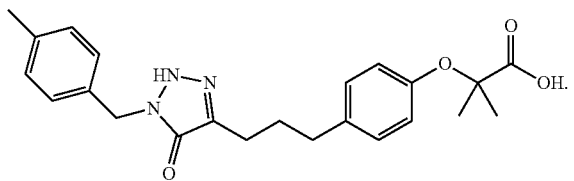 [SMILES: Cc1ccc(Cn2[nH]nc(CCCc3ccc(OC(C)(C)C(=O)O)cc3)c2=O)cc1]

In some embodiments, the PPARα agonist is an omega-3 fatty acid (e.g., icosapent ethyl (Vascepa®), docosahexaenoic acid). In some embodiments, the PPARα agonist is docosahexaenoic acid (DHA). In some embodiments, the PPARα agonist is icosapent ethyl. In some embodiments, the omega-3 fatty acid is administered in a composition comprising omega-3 fatty acid, such as fish oil. In some embodiments, the PPARα agonist is icosapent ethyl. In some embodiments, docosahexaenoic acid is administered in a composition comprising docosahexaenoic acid, such as fish oil. In some embodiments, the method described herein comprises administering an ACC inhibitor, e.g., Compound 1 or Compound 2, in combination with fish oil to a patient in need thereof.

In some embodiments, the PPARα agonist is a compound described in U.S. Patent application publication US20070197615 (which is hereby incorporated by reference in its entirety), such as NS-220.

In some embodiments, the PPARα agonist is fenofibrate. In some embodiments, fenofibrate is administered at a dosage of about 30 mg to about 200 mg per day. In some embodiments, fenofibrate is administered at a dosage of about 30 mg to about 200 mg once daily. In some embodiments, fenofibrate is administered at a dosage of about 30 to about 67 mg, about 40 to about 54 mg, about 40 mg to about 200 mg, about 50 to about 150 mg, about 90 to about 200 mg, about 120 to about 160 mg, about 50 mg, or about 150 mg once daily. In some embodiments, fenofibrate is administered orally. In some embodiments, the daily dosage of fenofibrate is administered as one or more tablets or capsules each containing about 30 mg, about 40 mg, about 43 mg, about 48 mg, about 50 mg, about 54 mg, about 67 mg, about 90 mg, about 120 mg, about 130 mg, about 134 mg, about 145 mg, about 150 mg, about 160 mg, or about 200 mg of fenofibrate.

In some embodiments, the PPARα agonist is bezafibrate. In some embodiments, bezafibrate is administered at a dosage of about 600 mg per day. In some embodiments, bezafibrate is administered in one tablet comprising 200 mg bezafibrate three times per day.

In some embodiments, the PPARα agonist is ciprofibrate. In some embodiments, ciprofibrate is administered at a dosage of about 100 mg per day. In some embodiments, ciprofibrate is administered in one tablet comprising 100 mg ciprofibrate per day.

In some embodiments, the PPARα agonist is clofibrate. In some embodiments, clofibrate is administered at a dosage of about 500 mg orally 4 times a day.

In some embodiments, the PPARα agonist is gemfibrozil. In some embodiments, gemfibrozil is administered at a dosage of about 600 mg orally twice a day. In some embodiments, gemfibrozil is administered 30 minutes before the morning and evening meal.

In some embodiments, the PPARα agonist is pemafibrate. In some embodiments, pemafibrate is administered at a dosage of about 0.1 mg to about 0.2 mg twice a day.

In some embodiments, the PPARα agonist is a PPARα/γ dual agonist including GW409544, AZ 242, LY518674 and a glitazar, such as aleglitazar, muraglitzar and saroglitazar. In some embodiments, the PPARα agonist is saroglitazar. In some embodiments, saroglitazar is administered orally in an amount of about 4 mg once a day.

Additional Therapeutic Agents

In some embodiments, the methods of treatment provided herein further comprise administering to the patient one or more additional therapeutic agents. In certain embodiments, the one or more additional therapeutic agents are independently selected from the group consisting of angiotensin II receptor antagonists, angiotensin converting enzyme (ACE) inhibitors, autotaxin inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGAT1) inhibitors, diacylglycerol O-acyltransferase 2 (DGAT2) inhibitors dipeptidyl peptidase IV (DPPIV) inhibitors, farnesoid X receptor (FXR) agonists, FXR/TGR5 dual agonists, galectin-3 inhibitors, glucagon-like peptide 1 (GLP1) agonists, glutathione precursors, hepatitis C virus NS3 protease inhibitors, HMG CoA reductase inhibitors, 11β-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, lysophosphatidic acid receptor antagonist, PDE3 inhibitors, PDE4 inhibitors, phospholipase C (PLC) inhibitors, Rho associated protein kinase 2 (ROCK2) inhibitors, sodium glucose transporter-2 (SGLT2) inhibitors, stearoyl CoA desaturase-1 inhibitors, thyroid hormone receptor β agonists, tumor necrosis factor α (TNFα) ligand inhibitors, ketohexokinase inhibitors, transglutaminase inhibitors, transglutaminase inhibitor precursors, vascular adhesion protein (VAP-1), platelet derived growth factor antagonist, cynnective tissue growth factor antagonist, PTP1b inhibitors, and ASK1 inhibitors.

In some embodiments, the additional therapeutic agent is an angiotensin II receptor antagonist.

In some embodiments, the additional therapeutic agent is an angiotensin converting enzyme (ACE) inhibitor. In some embodiments, the ACE inhibitor is enalapril.

In some embodiments, the additional therapeutic agent is a caspase inhibitor. In some embodiments the caspase inhibitor is emricasan.

In some embodiments, the additional therapeutic agent is a cathepsin B inhibitor. In some embodiments the cathepsin B inhibitor is a mixed cathepsin B/hepatitis C virus NS3 protease inhibitor. In some embodiments, the mixed cathepsin B/hepatitis C virus NS3 protease inhibitor is VBY-376.

In some embodiments, the additional therapeutic agent is a CCR2 chemokine antagonist. In some embodiments, the additional therapeutic agent is a mixed CCR2/CCR5 chemokine antagonist. In some embodiments, the mixed CCR2/CCR5 chemokine antagonist is cenicriviroc.

In some embodiments, the additional therapeutic agent is a CCR5 chemokine antagonist.

In some embodiments, the additional therapeutic agent is a chloride channel stimulator. In some embodiments, the chloride channel stimulator is cobiprostone.

In some embodiments, the additional therapeutic agent is a cholesterol solubilizer.

In some embodiments, the additional therapeutic agent is a diacylglycerol O-acyltransferase 1 (DGAT1) inhibitor. In some embodiments, the DGAT1 inhibitor is LCQ908.

In some embodiments, the additional therapeutic agent is a dipeptidyl peptidase IV (DPPIV) inhibitor. In some embodiments, the DPPIV inhibitor is linagliptin.

In some embodiments, the additional therapeutic agent is a farnesoid X receptor (FXR) agonist. In some embodiments, the FXR agonist is INT-747 (obeticholic acid). In some embodiments, the FXR agonist is PX-102.

In some embodiments, the additional therapeutic agent is an FXR/TGR5 dual agonist. In some embodiments, the FXR/TGR5 dual agonist is INT-767.

In some embodiments, the additional therapeutic agent is a galectin-3 inhibitor. In some embodiments, the galectin-3 inhibitor is GR-MD-02.

In some embodiments, the additional therapeutic agent is a glucagon-like peptide 1 (GLP1) agonist. In some embodiments, the GLP1 agonist is liraglutide. In some embodiments, the GLP1 agonist is exenatide.

In some embodiments, the additional therapeutic agent is a glutathione precursor.

In some embodiments, the additional therapeutic agent is a hepatitis C virus NS3 protease inhibitor. In some embodiments the heptatitis C virus NS3 protease inhibitor is a mixed cathepsin B/hepatitis C virus NS3 protease inhibitor. In some embodiments, the mixed cathepsin B/hepatitis C virus NS3 protease inhibitor is VBY-376.

In some embodiments, the additional therapeutic agent is an HMG CoA reductase inhibitor. In some embodiments, the HMG-CoA reductase inhibitor is a statin. In some embodiments, the HMG-CoA reductase inhibitor is atorvastatin.

In some embodiments, the additional therapeutic agent is an 11β-hydroxysteroid dehydrogenase (11(3-HSD1) inhibitor. In some embodiments, the 11β-HSD1 inhibitor is RO5093151.

In some embodiments, the additional therapeutic agent is an IL-1β antagonist.

In some embodiments, the additional therapeutic agent is an IL-6 antagonist. In some embodiments, the IL-6 antagonist is a mixed IL-6/IL-1β/TNFα ligand inhibitor. In some embodiments, the mixed IL-6/IL-1β/TNFα ligand inhibitor is BLX-1002.

In some embodiments, the additional therapeutic agent is an IL-10 agonist. In some embodiments, the IL-10 agonist is peg-ilodecakin.

In some embodiments, the additional therapeutic agent is an IL-17 antagonist. In some embodiments, the IL-17 antagonist is KD-025.

In some embodiments, the additional therapeutic agent is an ileal sodium bile acid cotransporter inhibitor. In some embodiments, the ileal sodium bile acid cotransporter inhibitor is SHP-626.

In some embodiments, the additional therapeutic agent is a leptin analog. In some embodiments the leptin analog is metreleptin.

In some embodiments, the additional therapeutic agent is a 5-lipoxygenase inhibitor. In some embodiments, the 5-lipoxygenase inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, the additional therapeutic agent is a LPL gene stimulator. In some embodiments the LPL gene stimulator is alipogene tiparvovec.

In some embodiments, the additional therapeutic agent is a lysyl oxidase homolog 2 (LOXL2) inhibitor. In some embodiments, the LOXL2 inhibitor is an anti-LOXL2 antibody. In some embodiments, the anti-LOXL2 antibody is GS-6624 (simtuzumab).

In some embodiments, the additional therapeutic agent is a PDE3 inhibitor. In some embodiments, the PDE3 inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, the additional therapeutic agent is a PDE4 inhibitor. In some embodiments, the PDE4 inhibitor is ASP-9831. In some embodiments, the PDE4 inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, the additional therapeutic agent is a phospholipase C (PLC) inhibitor. In some embodiments, the PLC inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, the additional therapeutic agent is a Rho associated protein kinase 2 (ROCK2) inhibitor. In some embodiments the ROCK2 inhibitor is KD-025.

In some embodiments, the additional therapeutic agent is a sodium glucose transporter-2 (SGLT2) inhibitor. In some embodiments, the SGLT2 inhibitor is remogliflozin etabonate.

In some embodiments, the additional therapeutic agent is a stearoyl CoA desaturase-1 inhibitor. In some embodiments, the stearoyl CoA desaturase-1 inhibitor is aramchol. In some embodiments, the stearoyl CoA desaturase-1 inhibitor is CVT-12805.

In some embodiments, the additional therapeutic agent is a thyroid hormone receptor agonist. In some embodiments the thyroid hormone receptor β agonist is MGL-3196.

In some embodiments, the additional therapeutic agent is a tumor necrosis factor α (TNFα) ligand inhibitor.

In some embodiments, the additional therapeutic agent is a transglutaminase inhibitor. In some embodiments, the transglutaminase inhibitor precursor is mercaptamine.

In some embodiments, the additional therapeutic agent is a transglutaminase inhibitor precursor.

In some embodiments, the additional therapeutic agent is a PTP1b inhibitor. In some embodiments, the PTP1b inhibitor is A119505, A220435, A321842, CPT633, ISIS-404173, JTT-551, MX-7014, MX-7091, MX-7102, NNC-521246, OTX-001, OTX-002, or TTP814.

In some embodiments, the additional therapeutic agent is an ASK1 inhibitor. In some embodiments, the ASK1 inhibitor is GS4977. In some embodiments, the ASK1 inhibitor is selonsertib (GS-4997).

In some embodiments, the one or more additional therapeutic agents are independently selected from acetylsalicylic acid, alipogene tiparvovec, aramchol, atorvastatin, BLX-1002, cenicriviroc, cobiprostone, colesevelam, emricasan, enalapril, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, and VBY-376.

In some embodiments, one of the one or more additional therapeutic agents is acetylsalicylic acid. In some embodiments, one of the one or more additional therapeutic agents is alipogene tiparvovec. In some embodiments, one of the one or more additional therapeutic agents is aramchol. In some embodiments, one of the one or more additional therapeutic agents is atorvastatin. In some embodiments, one of the one or more additional therapeutic agents is BLX-1002. In some embodiments, one of the one or more additional therapeutic agents is cenicriviroc. In some embodiments, one of the one or more additional therapeutic agents is cobiprostone. In some embodiments, one of the one or more additional therapeutic agents is colesevelam. In some embodiments, one of the one or more additional therapeutic agents is emricasan. In some embodiments, one of the one or more additional therapeutic agents is enalapril. In some embodiments, one of the one or more additional therapeutic agents is GR-MD-02. In some embodiments, one of the one or more additional therapeutic agents is hydrochlorothiazide. In some embodiments, one of the one or more additional therapeutic agents is icosapent ethyl ester (ethyl eicosapentaenoic acid). In some embodiments, one of the one or more additional therapeutic agents is IMM-124E. In some embodiments, one of the one or more additional therapeutic agents is KD-025. In some embodiments, one of the one or more additional therapeutic agents is linagliptin. In some embodiments, one of the one or more additional therapeutic agents is liraglutide. In some embodiments, one of the one or more additional therapeutic agents is mercaptamine. In some embodiments, one of the one or more additional therapeutic agents is MGL-3196. In some embodiments, one of the one or more additional therapeutic agents is obeticholic acid. In some embodiments, one of the one or more additional therapeutic agents is olesoxime. In some embodiments, one of the one or more additional therapeutic agents is peg-ilodecakin. In some embodiments, one of the one or more additional therapeutic agents is pioglitazone. In some embodiments, one of the one or more additional therapeutic agents is PX-102. In some embodiments, one of the one or more additional therapeutic agents is. In some embodiments, one of the one or more additional therapeutic agents is remogliflozin etabonate. In some embodiments, one of the one or more additional therapeutic agents is SHP-626. In some embodiments, one of the one or more additional therapeutic agents is solithromycin. In some embodiments, one of the one or more additional therapeutic agents is tipelukast. In some embodiments, one of the one or more additional therapeutic agents is TRX-318. In some embodiments, one of the one or more additional therapeutic agents is ursodeoxycholic acid. In some embodiments, one of the one or more additional therapeutic agents is and VBY-376.

In some embodiments, at least one of the one or more additional therapeutic agents is an anti-diabetic agent. In some embodiments, the anti-diabetic agent is an adenosine $A_1$ receptor agonist (e.g. adenosine, CCPA, CVT-3619, GR-190718), an adenosine A2 receptor antagonist (istradefylline, SCH-58261), an aldose reductase inhibitor, an α-amylase inhibitor (e.g. tendamistat, treastatin, AL-3688), an α-glucosidase inhibitor (e.g. acarbose, camiglibose, diposine, emiglitate, miglitol, pradimicin-Q, sarbostatin, voglibose), an amylin analog (e.g. AC164209 and pramlintide), an AMPK activator, a β-adrenergic agonist (e.g. amibegron, AZ-40140, CL-316,243, KRP-204, L-742,791, L-796,568, LY-368,842, LY-377,604, mirabegron, Ro 40-2148, solabegron, SWR-0342SA), a β-ketoacyl-acyl carrier protein synthase inhibitor, a biguanide (e.g. metformin, buformin, phenformin), a carnitine palmitoyl transferase inhibitor, a DGAT-2 inhibitor, a DPP-4 inhibitor (e.g. alogliptin, anagliptin, dutogliptin, gemigliptin, linagliptin, omarigliptin, saxagliptin, sitagliptin, teneligliptin, trelagliptin, and vildagliptin), an ERN1 inhibitor, a fatty acid oxidation inhibitor, a fatty acid synthase (FAS) inhibitor, an FGF21 derivative, a fructose 1,6-diphosphatase inhibitor, a GLP1 agonist (e.g. albiglutide, dulaglutide, exenatide, liraglutide, lixisenatide, taspoglutide), a glucagon receptor modulator, a mixed glucagon receptor/GLP-1 agonist (e.g. MAR-701, ZP2929), a glucokinase inhibitor (e.g. TTP-399, TTP-355, TTP-547, AZD1656, ARRY403, MK-0599, TAK-329, AZD5658, and GKM-001), a glycogen phosphorylase inhibitor (e.g. GSK1362885), a GSK-3 inhibitor, a GPR119 agonist (e.g. MBX-2982, GSK1292263, APD597, PSN821), a GPBAR1 (TGR5) agonist (e.g. INT-777, XL-475), a GPR39 modulator, a GPR40 agonist (e.g. TAK-875), a GPR41 modulator, a GPR43 modulator, a GPR81 modulator, a GPR120 agonist, an HSL inhibitor, an IκB inhibitor, an ILI-beta modulator, insulin or an insulin analog (including, but not limited to, oral, inhaled or injectable formulations thereof), insulin-like growth factor (IGF-1) or an analog thereof, an insulin secretagogue, a JNK inhibitor (e.g. CC-359), a kappa opioid receptor modulator, LY3084077, a Kv1.3 inhibitor (e.g. ChTX, clofazmine, WIN-173173), a MAP4K4 inhibitor, an $MC_1$ or $MC_4$ agonist (e.g. afamelanotide, BMS-470539, bremelanotide, Melanotan II, PF-00446687, PL-6983, setmelanotide, and THIQ), a meglitinide (e.g. repaglinide, nateglinide, mitiglinide), a mineralocorticoid receptor inhibitor, a monoacylglycerol O-acyltransferase inhibitor, an NF-κB inhibitor, a nicotinic acid receptor (HM74A) activator, a PDE-10 inhibitor, a PDHK2 inhibitor, a PDHK4 inhibitor, a PKC (including PKC-alpha, PKC-beta, and PKC-gamma) inhibitor, a PTP1b inhibitor (e.g. trodusquemine), a retinol binding protein 4 inhibitor, a serine palmitoyl transferase inhibitor, an SGLT1 inhibitor (e.g. GSK1614235), a SIRT-1 inhibitor (e.g. resveratrol, GSK2245840, GSK184072), a somatostatin receptor inhibitor, a sulfonylurea (e.g. acetohexamide, chlorpropamide, diabinese, glibenclamide, glipizide, glyburide, blimipiride, gliclazide, glipentide, gliquidone, glisolamide, tolazamide, tolbutamide), a thiazolidinedione (e.g. ciglitazone, darglitazone, englitazone, lobeglitazone, MSDC-0602, netoglitazone, pioglitazone, rivoglitazone, rosiglitazone, and troglitazone), a TORC2 inhibitor, a urotensin II receptor agonist, a vasopressin agonist (e.g. DDAVP, WAY-141608), a VPAC2 receptor agonist, or ketohexokinase inhibitor (e.g. PF-06835919).

In some embodiments, at least one of the one or more additional therapeutic agents is an anti-antiobesity agent. In some embodiments, the anti-obesity agent is an apoB-MTP inhibitor (e.g. dirlotapide, JTT130, SLX4090, usistapide), a β3-adrenergic agonist (e.g. amibegron, AZ-40140, CL-316, 243, KRP-204, L-742,791, L-796,568, LY-368,842, LY-377, 604, mirabegron, Ro 40-2148, solabegron, SWR-0342SA), a bombesin receptor agonist, a BRS3 modulator, a CB1 receptor antagonist or inverse agonist, a $CCK_A$ agonist, ciliary neurotrophic factor (CNTF) or analog thereof (e.g. axokine, NT-501), Contrave™ (buproprion/naltrexone), a dopamine receptor agonist (e.g. bromocriptine), an 11β-hydroxysteroid dehydrogenase (11β-HSD1) inhibitor, Empatic™ (pramlintide/metreleptin), a 5-HT2c agonist (e.g. lorcaserin), a galanin antagonist, a ghrelin agonist or antagonist, a GLP1 agonist (e.g. albiglutide, dulaglutide, exenatide, liraglutide, lixisenatide, taspoglutide), a mixed glucagon receptor/GLP-1 agonist (e.g. MAR-701, ZP2929), an H3 antagonist or inverse agonist, a human agouti-related protein (AGRP) inhibitor, leptin or an analog thereof (e.g. metreleptin), a lipase inhibitor (e.g. tetrahydrolipstatin), an $MC_1$ or $MC_4$ agonist (e.g. afamelanotide, BMS-470539, bremelanotide, Melanotan II, PF-00446687, PL-6983, setmelanotide, and THIQ), a melanocyte-stimulating hormone or analog thereof, a MetAp2 inhibitor (e.g. ZGN-433), a monoamine reuptake inhibitor (e.g. buproprion, sibutramine, phentermine, tesofensine), a neuromedin U receptor agonist, an NPY antagonist (e.g. velneperit), an opioid receptor antagonist (e.g. naltrexone), an orexin receptor antagonist (e.g. almorexant, lemborexant, SB-334,867, SB-408,124, SB-649,868, suvorexant), oxyntomodulin or an analog thereof, PYY or an analog thereof (e.g. $PYY_{1-36}$, $PYY_{3-36}$), Qsymia™ (phentermine/topiramate), an RXR-alpha modulator, a stearoyl-CoA desaturase (SCD-1) inhibitor, or a sympathomimetic agent.

In some embodiments, at least one of the one or more additional therapeutic agents is a lipid lowering agent. In some embodiments, the lipid lowering agent is an acyl coenzyme A cholesterol acyl transferase (ACAT) inhibitor, a bile acid reabsorption inhibitor, a cholesterol ester transfer protein (CETP) inhibitor, a 5-LOX inhibitor (e.g. BAY X 1005), a FLAP inhibitor (e.g. AM-679), an HMG CoA synthase inhibitor, a lipoprotein synthesis inhibitor, a low-density lipoprotein receptor inducer, an LXR receptor modulator, a microsomal triglyceride transport inhibitor, niacin, a platelet aggregation inhibitor, a renin-angiotensin system inhibitor, a squalene epoxidase inhibitor, a squalene synthetase inhibitor, or a triglyceride synthesis inhibitor.

In some embodiments, at least one of the one or more additional therapeutic agents is an agent for treating a metabolic disorder. In some embodiments, the agent for treating a metabolic disorder is an ABC transporter activator, ACT-434964 (Actelion), an ANG-5 inhibitor, an angiotensin II antagonist (e.g. MC4262), CCX-872, DUR-928 (Durect), ESP41091, F-652 (Generon), an FGF21 agonist (e.g. BMS-986036), fomepizole (Raptor), an FXR agonist, FXR/TGR5 dual agonist (e.g. INT-767), a ghrelin antagonist (e.g. TZP-301), a glucosylceramide synthase inhibitor, a GPR17 modulator, a GPR119 agonist, IG-MD-014 (Indigene), IMM-124E (Immuron), a lysosome pathway modulator (e.g. CAT5000), a melanin-concentrating hormone receptor 1 antagonist (e.g. KI-1361-17), an MCL1 inhibitor (e.g. CMPX-1023), an mTORC1 inhibitor, an NaCT (e.g. SLC13A5) inhibitor, a NHE3 inhibitor (e.g. RDX-011, tenapanor), NP003 (Neuraltus), PBI-4050 (ProMetic), a proteostasis regulator (e.g. PTI-130, PTI-428, PTI-C1811), PS248288 (Pharmacopeia/Merck), PX-102 (Phenex), RG7410. RG7652, a ROCK inhibitor, SBC-104 (Synageva BioPharma), SPX-100 (Spherix), a stearoyl CoA desaturase inhibitor (e.g. CVT-12805), TRC150094 (Torrent), or ZYH7 (Zydus Cadila).

In some embodiments, at least one of the one or more additional therapeutic agents is an agent for treating steatosis. In some embodiments, the agent for treating steatosis is an adiponectin analog (e.g. PX 811013), aramchol (Galmed), an ASK1 inhibitor (e.g. GS4977, GS4997 (also known as selonsertib)), AZD4076 (AstraZeneca), a bile acid sequestrant (e.g. obeticholic acid), BL-1060 (Galmed), BMS986171 (Bristol-Myers Squibb), a CCR5/CCR2 antagonist (e.g. cenicriviroc), cannabidiol, CER-209 (Cerenis), a cysteamine analog (e.g. RP-103, RP-104), DS102 (DS Biopharma), EGS21 (Enzo), elafibranor (Genfit), emricasan (Idun), ethyl eicosapentaenoic acid (Mochida), an FXR agonist, a GPBAR1 agonist (e.g. RDX009), GR-MD-02 (Galectin Therapeutics), leucine/sildenafil/metformin (NuSirt), LCQ908 (Novartis), LJN452 (Novartis), a LOXL2 inhibitor (e.g. simtuzumab), MAT-8800 (Matinas), MB-10866 (Metabasis), an miR-103/107 inhibitor (e.g. RG-125), MK-4074 (Merck & Co.), nalmefene (TaiwanJ), nivocasan (Gilead), NGM-282 (NGM Biopharmaceuticals), an omega-3 carboxylic acid or mixture of the same (e.g. Epanova™), PX-102 (Phenex), PX-104 (Phenex), remogliflozin etabonate (Kissei), saroglitazar (Zydus-Cadila), SAR-548304 (sanofi-aventis), tipelukast (Kyorin), ursodeoxycholic acid, VK2809 (Viking), or XL335 (Exelixis). In some embodiments, the additional therapeutic agent is selonsertib, san FXR agonist, or a combination thereof.

In some embodiments, at least one of the one or more additional therapeutic agents is an agent for treating inflammation. In some embodiments, the agent for treating inflammation reduces the differentiation or activation of $T_h17$ cells. In some embodiments, the agent for treating inflammation is a caspase inhibitor (e.g. emricasan), a TGF-β inhibitor, an IL-1β inhibitor, an IL-6 inhibitor, an IL-17 inhibitor, an IL-17a inhibitor, an IL-17F inhibitor, an IL-21 inhibitor, an IL-23 inhibitor (e.g. guselkumab), IMM-124E, a RORγt inhibitor (e.g. JTE-151) a RORα inhibitor, solithromycin (Cempra), or a vascular adhesion protein-1 inhibitor (e.g. PXS-4728A).

In some embodiments, at least one of the one or more additional therapeutic agents is an agent for treating fibrosis. In some embodiments, the agent for treating fibrosis is cenicriviroc (Tobira/Takeda), CNX-014/023/024/025 (Connexios), an endothelin antagonist (e.g. A192621, ambrisentan, atracentan, bosentan, BQ-123, BQ-788, macitentan, sitaxentan, tezosentan, zibotentan), etanercept, evitar (AdeTherapeutics), a fibroblast growth factor inhibitor, a galectin-3 inhibitor, imatinib, IVA337 (Inventiva), N-acetylcysteine, nintedanib, pirfenidone, RG6069 (Roche), SP20102 (Sarfez), tipelukast (Kyorin), or XOMA 089 (Xoma).

In some embodiments, the methods of treatment provided herein further comprise administering to the patient an ACC inhibitor, e.g., Compound 1 or Compound 2, in combination with PPARα agonist or fish oil, and optionally an additional therapeutic agent selected from selonsertib, an FXR agonist, or a combination thereof.

In some aspects, provided herein is a method of treating, stabilizing or lessening the severity or progression of a non-alcoholic steatohepatitis (NASH), wherein the method comprises administering to a patient in need thereof Compound 1 in combination with a PPARα agonist or fish oil, and optionally an additional therapeutic agent selected from selonsertib, an FXR agonist, or a combination thereof.

In some aspects, provided herein is a method of treating, stabilizing or lessening the severity or progression of a non-alcoholic steatohepatitis (NASH), wherein the method comprises administering to a patient in need thereof Compound 2 in combination with a PPARα agonist or fish oil, and optionally an additional therapeutic agent selected from selonsertib, an FXR agonist, or a combination thereof.

In some aspects, provided herein is a method of treating, stabilizing or lessening the severity or progression of a non-alcoholic steatohepatitis (NASH), wherein the method comprises administering to a patient in need thereof 20 mg of Compound 1 in combination with a PPARα agonist or fish oil, and optionally an additional therapeutic agent selected from selonsertib, an FXR agonist, or a combination thereof.

In some aspects, provided herein is a method of treating, stabilizing or lessening the severity or progression of a non-alcoholic steatohepatitis (NASH), wherein the method comprises administering to a patient in need thereof 20 mg of Compound 2 in combination with a PPARα agonist or fish oil, and optionally an additional therapeutic agent selected from selonsertib, an FXR agonist, or a combination thereof.

In some aspects, provided herein is a method of treating, stabilizing or lessening the severity or progression of a non-alcoholic steatohepatitis (NASH), wherein:
the method comprises administering to a patient in need thereof about 20 mg of Compound 1 in combination with a PPARα agonist or fish oil, and optionally an additional therapeutic agent selected from selonsertib, an FXR agonist, or a combination thereof, and
the patient has a serum triglyceride level of <250 mg/dL prior to administration.

In some aspects, provided herein is a method of treating, stabilizing or lessening the severity or progression of a non-alcoholic steatohepatitis (NASH), wherein:
the method comprises administering to a patient in need thereof about 20 mg of Compound 2 in combination with a PPARα agonist or fish oil, and optionally an additional therapeutic agent selected from selonsertib, an FXR agonist, or a combination thereof, and
the patient has a serum triglyceride level of <250 mg/dL prior to administration.

In some aspects, provided herein is a method of treating, stabilizing or lessening the severity or progression of a non-alcoholic steatohepatitis (NASH), wherein:
the method comprises administering to a patient in need thereof about 20 mg of Compound 1 in combination with a PPARα agonist or fish oil, and optionally an additional therapeutic agent selected from selonsertib, an FXR agonist, or a combination thereof, the PPARα agonist is fenofibrate, bezafibrate, elafinbranor, or saroglitazar, and the patient has a serum triglyceride level of <250 mg/dL prior to administration of Compound 1 in combination with a PPARα agonist or fish oil.

In some aspects, provided herein is a method of treating, stabilizing or lessening the severity or progression of a non-alcoholic steatohepatitis (NASH), wherein:
the method comprises administering to a patient in need thereof about 20 mg of Compound 2 in combination with a PPARα agonist or fish oil, and optionally an additional therapeutic agent selected from selonsertib, an FXR agonist, or a combination thereof, the PPARα agonist is fenofibrate, bezafibrate, elafinbranor, or saroglitazar, and the patient has a serum triglyceride level of <250 mg/dL prior to administration Compound 2 in combination with a PPARα agonist or fish oil.

In some aspects, provided herein is a method of treating, stabilizing or lessening the severity or progression of a non-alcoholic steatohepatitis (NASH), wherein:
the method comprises administering to a patient in need thereof about 20 mg of Compound 1 in combination with a PPARα agonist or fish oil, and optionally an additional therapeutic agent selected from selonsertib, an FXR agonist, or a combination thereof, the PPARα agonist is fenofibrate, bezafibrate, elafinbranor, or saroglitazar, and the patient is administered the PPARα agonist or fish oil prior to administration of Compound 1 (optionally in combination with a PPARα agonist or fish oil).

In some aspects, provided herein is a method of treating, stabilizing or lessening the severity or progression of a non-alcoholic steatohepatitis (NASH), wherein:
the method comprises administering to a patient in need thereof about 20 mg of Compound 2 in combination with a PPARα agonist or fish oil, and optionally an additional therapeutic agent selected from selonsertib, an FXR agonist, or a combination thereof, the PPARα agonist is fenofibrate, bezafibrate, elafinbranor, or saroglitazar, and the patient is administered the PPARα agonist or fish oil prior to administration of Compound 2 (optionally in combination with a PPARα agonist or fish oil).

Combination Dosing

As described herein, provided methods comprise administration to a patient in need thereof, an ACC inhibitor, e.g., Compound 1 or Compound 2, in combination with PPARα agonist or fish oil, and optionally one or more additional therapeutic agents. As used herein, the term "in combination" with regard to administration of an ACC inhibitor, e.g., Compound 1 or Compound 2, the PPARα agonist or fish oil, and the optional one or more therapeutic agents means that each of an ACC inhibitor, e.g., Compound 1 or Compound 2, the PPARα agonist or fish oil, and the optional one or more therapeutic agents can be administered to the patient in any order (i.e., simultaneously or sequentially) or together in a single composition, formulation, or unit dosage form.

It will be appreciated that an ACC inhibitor, e.g., Compound 1 or Compound 2, the PPARα agonist or fish oil, and the optional one or more additional therapeutic agents can be administered on the same day or on different days and in any order as according to an appropriate dosing protocol.

In some embodiments, administration of a PPARα agonist or fish oil starts a period of time (as such at least one day, three days, one week, two weeks, or a month) before administration of an ACC inhibitor, e.g., Compound 1 or Compound 2, starts, and optionally continues during at least part of the administration period of the ACC inhibitor, e.g., Compound 1 or Compound 2. In some embodiments, administration of a PPARα agonist or fish oil starts on the same day administration of an ACC inhibitor, e.g., Compound 1 or Compound 2, starts. In some embodiments, an ACC inhibitor, e.g., Compound 1 or Compound 2, is administered with a PPARα agonist or fish oil for at least a period of time (as such at least one day, three days, one week, two weeks, or a month) after administration of the ACC inhibitor, e.g., Compound 1 or Compound 2, starts. In some embodiments, administration of a PPARα agonist or fish oil starts when the patient exhibits elevated triglyceride levels, such as at least borderline high triglyceride levels. In some embodiments, administration of a PPARα agonist or fish oil continues until the patient exhibits normal triglyceride levels. In some embodiments, administration of a PPARα agonist or fish oil continues during the entire treatment course of the ACC inhibitor, e.g., Compound 1 or Compound 2. In some embodiments, administration of the ACC inhibitor, e.g., Compound 1 or Compound 2, stops or is at a reduced dosage while the patient is being administered a PPARα agonist or fish oil when the patient exhibits elevated triglyceride levels, such as at least borderline high triglyceride levels, and resumes after the patient exhibits normal triglyceride levels, optionally with continued administration of the PPARα agonist or fish oil. In some embodiments, the same PPARα agonist or fish oil is administered during a treatment course of the ACC inhibitor, e.g., Compound 1 or Compound 2. In some embodiments, different PPARα agonists or fish oil are administered during a treatment course of the ACC inhibitor, e.g., Compound 1 or Compound 2.

Dosing of a PPARα Agonist or the Additional Therapeutic Agents

In some embodiments, a PPARα agonist or an optional additional therapeutic agent is administered in an amount of about 0.1 mg/day to about 1200 mg/day. In some embodiments, a PPARα agonist or each of the one or more optional additional agent is administered in an amount of 1 mg/day to about 100 mg/day, about 10 mg/day to about 1200 mg/day, about 10 mg/day to about 100 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day. In some embodiments, methods disclosed herein comprise the administration of 0.1 mg/day, 0.5 mg/day, 1 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day or 800 mg/day of a PPARα agonist and optionally a therapeutic agent to a patient in need thereof.

In some embodiments, the total daily dose of a PPARα agonist or each of the one or more additional therapeutic agents is selected from about 5 mg, about 10 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments, the total daily dose of a PPARα agonist or each of the one or more additional therapeutic agents is independently between about 5 mg to about 3000 mg, between about 5 mg to about 1000 mg, between about 5 mg to about 500 mg, between about 5 mg to about 100 mg, between about 10 mg to about 3000 mg, between about 10 mg to about 2000 mg, between about 10 mg to about 1000 mg, between about 20 mg to about 1000 mg, between about 30 mg to about 1000 mg, between about 30 mg to about 750 mg, between about 30 mg to about 500 mg, between about 30 mg to about 250 mg, between about 30 mg to about 100 mg, between about 50 mg to about 500 mg, or between about 50 mg to about 100 mg.

Unit Dosage Forms of Additional Therapeutic Agents

In some embodiment, a PPARα agonist and each of the one or more optional additional therapeutic agents is administered in unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of the PPARα agonist or the therapeutic agent.

In some embodiments, provided herein are unit dosage formulations comprising about 0.1 mg, 0.25 mg, 0.5 mg, 1 mg, 5 mg, 10 mg, 15 mg, 20 mg, 30 mg, 45 mg, 50 mg, 60 mg, 75 mg, 100 mg, 125 mg, 150 mg, 200 mg, 250 mg, 300 mg, 400 mg, 600 mg or 800 mg of a PPARα agonist or an additional therapeutic agent.

In some embodiments, provided herein are unit dosage formulations that comprise 0.1 mg, 0.25 mg, 0.5 mg, 1 mg, 2.5 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a PPARα agonist or an additional therapeutic agent. In a particular embodiment, provided herein are unit dosage formulations that comprise about 5 mg, about 15 mg, about 20 mg, about 30 mg, about 45 mg, and about 50 mg of a PPARα agonist or an additional therapeutic agent.

Administration of a PPARα Agonist or Fish Oil or Additional Therapeutic Agents

In some embodiments, provided methods comprise administering a pharmaceutically acceptable composition comprising a PPARα agonist or fish oil or one or more additional therapeutic agents one, two, three, or four times a day.

In some embodiments, a pharmaceutically acceptable composition comprising a PPARα agonist or fish oil or one or more additional therapeutic agents is administered once daily ("QD").

In some embodiments, a pharmaceutically acceptable composition comprising a PPARα agonist or fish oil or one or more additional therapeutic agents is administered twice daily. In some embodiments, twice daily administration refers to a compound or composition that is administered "BID", or two equivalent doses administered at two different times in one day.

In some embodiments, a pharmaceutically acceptable composition comprising a PPARα agonist or fish oil or one or more additional therapeutic agents is administered three times a day. In some embodiments, a pharmaceutically acceptable composition comprising a PPARα agonist or fish oil or one or more additional therapeutic agents is administered "TID", or three equivalent doses administered at three different times in one day.

In some embodiments, a pharmaceutically acceptable composition comprising a PPARα agonist or fish oil or one or more additional therapeutic agents is administered four times a day. In some embodiments, a pharmaceutically acceptable composition comprising a PPARα agonist or fish oil or one or more additional therapeutic agents is administered "QID", or four equivalent doses administered at four different times in one day. In some embodiments, a pharmaceutically acceptable composition comprising a PPARα agonist or fish oil or one or more additional therapeutic agents is administered for a various number of days (for example 14, 21, 28) with a various number of days between treatment (0, 14, 21, 28).

In some embodiments, a PPARα agonist or fish oil or an additional therapeutic agent are administered to a patient under fasted conditions and the total daily dose is any of those contemplated above and herein.

In some embodiments, a PPARα agonist or fish oil or an additional therapeutic agent is administered to a patient under fed conditions and the total daily dose is any of those contemplated above and herein.

In some embodiments, a PPARα agonist or fish oil or an additional therapeutic agent is administered orally. In some embodiments, when administered orally, a PPARα agonist or fish oil or an additional therapeutic agent is administered with a meal and water. In another embodiment, a PPARα agonist or fish oil or an additional therapeutic agent is dispersed in water or juice (e.g., apple juice or orange juice) and administered orally as a suspension. In some embodiments, when administered orally, a PPARα agonist or fish oil or an additional therapeutic agent is administered in a fasted state.

A PPARα agonist or a therapeutic agent can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition. Pharmaceutically Acceptable Compositions of Either of Compound 1 or Compound 2, and a PPARα Agonist In some embodiments, the present invention provides a pharmaceutically acceptable composition comprising either of Compound 1 or Compound 2, or a pharmaceutically acceptable composition of a PPARα agonist for use in the methods described herein. In some embodiments, a composition comprising Compound 1 or Compound 2, is separate from a composition comprising a PPARα agonist. In some embodiments, Compound 1 or Compound 2, and a PPARα agonist are present in the same composition.

Exemplary such pharmaceutically acceptable compositions are described further below and herein.

Liquid dosage forms for oral administration include, but are not limited to, pharmaceutically acceptable emulsions, microemulsions, solutions, suspensions, syrups and elixirs. In addition to an ACC inhibitor and/or one or more additional therapeutic agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound 1 or Compound 2, and/or a PPARα agonist, it is often desirable to slow absorption from subcutaneous or intramuscular injection. This may be accomplished by the use of a liquid suspension of crystalline or amorphous material with poor water solubility. The rate of absorption then depends upon its rate of dissolution that, in turn, may depend upon crystal size and crystalline form. Alternatively, delayed absorption of parenterally administered Compound 1 or Compound 2, and/or a PPARα agonist, is accomplished by dissolving or suspending the compound in an oil vehicle. Injectable depot forms are made by forming microencapsule matrices of Compound 1 or Compound 2, and/or a PPARα agonist, in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly (anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compound 1 or Compound 2, and/or a PPARα agonist can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms Compound 1 or Compound 2, and/or a PPARα agonist may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of Compound 1 or Compound 2, and/or a PPARα agonist include ointments, pastes, creams, lotions, gels, powders, solutions, sprays, inhalants or patches. The active components are admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the disclosure relates to a method of inhibiting de novo fatty acid synthesis in a biological sample comprising the step of contacting said biological sample with Compound 1 or Compound 2, and/or a PPARα agonist.

According to one embodiment, the disclosure relates to a method of increasing fatty acid oxidation in a biological sample comprising the step of contacting said biological sample with Compound 1 or Compound 2, and/or a PPARα agonist.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Example 1

Compound 1 in a Phase 2, Randomized, Placebo-Controlled Trial of Patients with NASH Methods:

In this double-blind, placebo-controlled trial, 126 non-cirrhotic subjects with NASH diagnosed noninvasively by MRI proton density fat fraction (PDFF) ≥8% and liver stiffness ≥2.5 kPa by MR elastography (MRE), or historical liver biopsy consistent with NASH and stage 1 to 3 fibrosis, were randomized 2:2:1 to receive Compound 1 20 mg, Compound 1 5 mg, or placebo orally QD for 12 weeks (W12). Centrally-read MRI-PDFF and MRE, and FibroScan and serum markers of fibrosis were measured at baseline and W12. In some subjects, liver stiffness and hepatic fat content by Controlled Attenuation Parameter (CAP) were assessed using transient elastography (FibroScan®; Echosens, Paris, France) at baseline (i.e. week 0) and week 12.

In addition to standard lipid tests (serum triglycerides ("TG"), total cholesterol ("TC"), low density lipoprotein cholesterol ("LDL-C"), and high density lipoprotein cholesterol ("HDL-C"), lipoproteins also were measured by nuclear magnetic resonance spectroscopy (NMR LipoProfile®, LabCorp) in fasting serum samples at baseline ("BL"), week 1 (W1), week 4 (W4), and W12. Changes from BL in Compound 1-treated subjects were evaluated using Wilcoxon sign-rank tests and comparisons vs placebo using Wilcoxon rank-sum tests (all with Bonferroni adjustment).

Acylcarnitine species measurements were performed with Ultrahigh Performance Liquid Chromatography-Tandem Mass Spectroscopy (UHPLC-MS; Waters Acquity UHPLC, Waters Corporation, Milford, Mass. USA) and Hybrid Quadrupole-Orbitrap mass spectometer (Q-Exactive Thermo Fischer Scientific, Waltham, Mass., USA) platforms in electrospray ionisation-positive and -negative modes as known.

Results (MRI-PDFF and MRE): The majority of the subjects were female (65%) and diabetic (60%); median MRI-PDFF and MRE-stiffness at baseline were 14.4% (IQR 11.1-19.0) and 3.43 kPa (2.96-4.20), respectively; 40% of subjects had MRE >3.64 kPa, consistent with advanced (≥F3) fibrosis. At W12, Compound 1 20 mg resulted in a statistically and clinically significant decrease in MRI-PDFF compared with placebo; differences between Compound 1 5 mg and placebo were not statistically significant (Table 1). At W12, a ≥30% decline in MRI-PDFF was observed in 48% of subjects treated with Compound 1 20 mg (p=0.004 vs. placebo), 23% treated with Compound 1 5 mg (p=0.433 vs. placebo), and 15% with placebo.

In some subjects, hepatic steatosis was measured by CAP. Dose-dependent reductions in CAP were observed in Compound 1-treated patients that paralleled changes in MRI-PDFF, but differences in CAP were not statistically significant (data not shown). Differences in changes in CAP between Compound 1-treated patients and those on placebo were most evident when measured using the XL probe versus the M probe.

Changes in liver stiffness by MRE did not differ between groups. However, subjects treated with Compound 1 20 mg had significant reductions in serum levels of TIMP-1 (Table 1); changes in TIMP-1 correlated with changes in PIII-NP (r=0.47; p=0.001) and hyaluronic acid (r=0.62; p<0.001). Dose-dependent, but not statistically significant reductions in serum ALT, liver stiffness by FibroScan, and PIII-NP were also observed. Compound 1 was generally well-tolerated. Changes in liver stiffness by FibroScan appeared to be dependent upon the type of probe used, as well as consistent use of the same type of probe over time. Using the M probe, no differences in change of liver stiffness from baseline to week 12 were observed between treatment groups. In patients measured with the XL probe, a statistically significant decrease in liver stiffness was observed in Compound 1-treated patients compared with placebo. Specifically, median (IQR) relative changes from baseline to week 12 were −7.2% (−32.6, 7.8) in patients treated with Compound 1 20 mg (p=0.04 vs placebo), −3.6% (−23.8, 8.2) in patients treated with Compound 1 5 mg (p=0.02 vs placebo), and +30.6% (4.5, 63.8) in those treated with placebo/Consistent use of the same probe between measurements was also associated with significant declines in liver stiffness in the Compound 1-treated groups compared with placebo.

Figure 3:
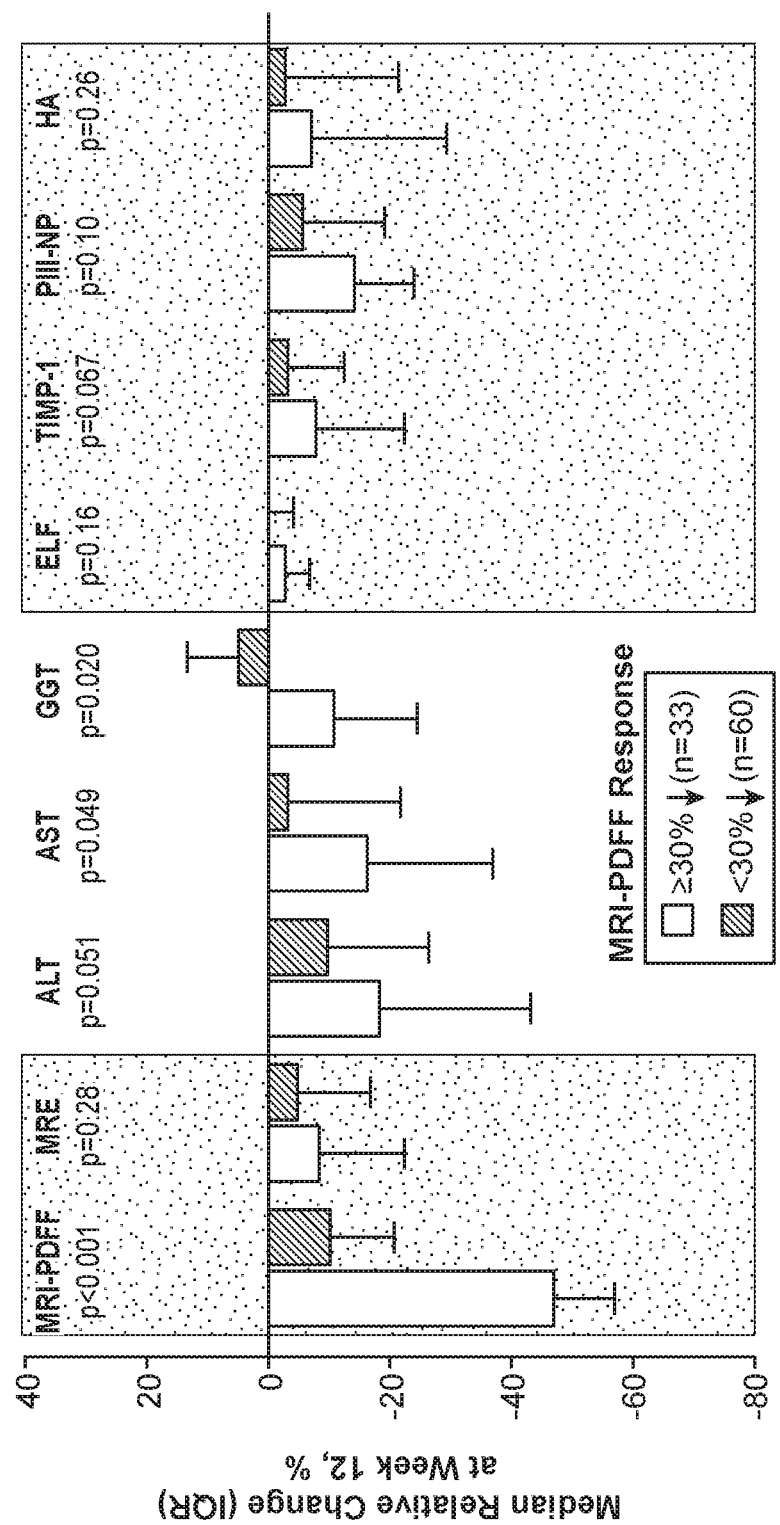
FIG. 3 illustrates changes in liver biochemistry and serum markers of fibrosis between baseline and week 12 according to MRI-PDFF response as described in Example 1. Data are median (IQR). For each marker, 2 columns are shown, where the left column corresponds to ≥30% decrease (n=33) and the right column corresponds to <30% decrease (n=60).

Results of medium relative change (IQR) at W12 of ALT, AST, GGT, ALP, TIMP-1, PIII-NP, and HA are also summarized in FIG. 1. The p-values reported in FIG. 1 are for comparison of Compound 1 versus placebo by Wilcoxon rank-sum test. Patients receiving Compound 1 at either doses had greater median relative reductions in ALT, TIMP-1, and PIII-NP than patients receiving placebo TIMP-1 was statistically significant between patients receiving Compound 1 20 mg versus placebo (p=0.022) (FIG. 1). Median alkaline phosphatase increased by 9% in patients receiving Compound 1 20 mg (p<0.001 vs placebo), but was unchanged or decreased in patients receiving Compound 1 5 mg and placebo, respectively. Changes in other liver biochemistry tests and the composite ELF score were not significantly different among the treatment groups. Compared to PDFF-nonresponders (n=60), the 33 patients who exhibited at least a 30% relative reduction from baseline in MRI-PDFF also showed decreases in liver biochemistry (ALT, AST, GGT) and the ELF score and its components (FIG. 3).

Multiple long and medium-chain acylcarnitine species, a surrogate marker of increased beta oxidation of fatty acids, were significantly reduced before administration of the next daily dose (~24 hours) in the Compound 1 20 mg treated group who exhibited a PDFF response versus those without a PDFF response (Table 3). On the contrary, patients in the Compound 1 5 mg or placebo groups showed minimal changes in acylcarnitine species when compared according to PDFF response. These data suggest that the measurement of plasma acylcarnitines may be used as a potential peripheral marker of enhanced mitochondrial β-oxidation during Compound 1 treatment (improved fatty acid catabolism with ACC inhibition by Compound 1).

Results (Lipid Parameters):

The median age was 56 years, 67% were female, 60% had diabetes, and 45% were on lipid lowering therapy at BL (39% statins, 4.8% fibrates, 17% other). At W12, a median relative change in triglycerides (TG) of +11%, +13%, and −4% was observed among subjects treated with Compound 1 20 mg, Compound 1 5 mg, and placebo. Asymptomatic, Grade 3 or 4 TG elevations (>500 mg/dL) were observed in 16 subjects on Compound 1 20 mg (n=7) or 5 mg (n=9). Of these 16 subjects, 4 responded to fibrate or fish oil therapy, and 7 of the remaining 12 subjects resolved without treatment or cessation of Compound 1. The primary factor associated with Grade 3 or 4 TG elevation was a baseline TG level >250 mg/dL (p<0.001).

TG elevations in subjects on Compound 1 peaked at W1 and declined thereafter (Table 2). At W12, a median (IQR) TG increase of 14 mg/dL (−6, 72) was observed among Compound 1-treated subjects compared with a reduction of 5.5 mg/dL (−24, 26) in those on placebo (p=0.14). Statistically significant increases in very low density lipoprotein (VLDL) particles and VLDL-TG at W1 were no longer significant at W12. Changes from baseline at W12 in HDL-C, TC, and LDL-C were not significant in Compound 1-treated subjects, but TC and LDL-C declined in those on placebo. No significant changes in total HDL or total LDL particles were observed in subjects on Compound 1. There were also no significant changes in glucose, insulin, or HbA1c with Compound 1 20 mg or Compound 1 5 mg compared to placebo.

Conclusions:

In this randomized, placebo-controlled study, 12-week therapy with the liver-targeted, oral ACC inhibitor Compound 1 20 mg QD, was safe and led to significant improvements in hepatic steatosis and selected fibrosis markers in patients with NASH. Additionally, it is contemplated that TG elevations in NASH patients treated with Compound 1 20 mg daily may relate to a transient increase in hepatic release of VLDL particles. Despite the increase in serum TG concentration, HDL and LDL particles did not change significantly.

TABLE 1

Relative (%) Changes in Imaging, ALT, and Serum Fibrosis Markers at W12 *

|  | Compound 1 20 mg (n = 49) | Compound 1 5 mg (n = 51) | Placebo (n = 26) | P-values 20 mg vs. Placebo | P-values 5 mg vs. Placebo |
|---|---|---|---|---|---|
| MRI-PDFF | −28.9 (n = 46) | −13.0 (n = 47) | −8.4 (n = 26) | 0.002 | 0.142 |
| ≥30% reduction in MRI-PDFF, % (n/N) | 48% (22/46) | 23% (11/47) | 15% (4/26) | 0.004 | 0.433 |
| MRE-stiffness | −5.5 (n = 46) | −9.6 (n = 47) | −12.5 (n = 26) | 0.100 | 0.743 |
| ≥15% reduction in MRE-stiffness, % (n/N) | 33% (15/46) | 40% (19/47) | 35% (9/26) | 0.92 | 0.62 |
| Liver stiffness by FibroScan | −11.1 (n = 40) | −8.4 (n = 40) | −3.1 (n = 24) | 0.212 | 0.364 |
| ALT | −20.5 | −9.8 | −6.7 | 0.176 | 0.765 |
| TIMP-1 | −7.9 | −2.9 | −1.5 | 0.022 | 0.301 |

TABLE 1-continued

Relative (%) Changes in Imaging, ALT, and Serum Fibrosis Markers at W12 *

| | Compound 1 20 mg (n = 49) | Compound 1 5 mg (n = 51) | Placebo (n = 26) | P-values 20 mg vs. Placebo | P-values 5 mg vs. Placebo |
|---|---|---|---|---|---|
| PIII-NP | −13.9 | −7.0 | −0.5 | 0.107 | 0.605 |
| Hyaluronic acid | −6.9 | −0.7 | −15.3 | 0.386 | 0.576 |

* Unless indicated, all data are median relative (%) changes from baseline.

The n values in each header refer to total number of subjects for each treatment arm; n values shown within cells depict number of subjects for data shown.

TABLE 2

Lipid Parameters in Subjects Treated with Compound 1 20 mg Daily for 12 Weeks

| Lipid Parameter | BL | W1 | W4 | W12 |
|---|---|---|---|---|
| TG (mg/dL) | 160 (125, 201) | 191 (136, 290)*† | 188 (142, 270)* | 177 (116, 277)* |
| VLDL-TG (nmol/L) | 93 (66, 133) | 120 (73, 236)*† | 97 (69, 200)* | 96 (68, 175) |
| VLDL-P (nmol/L) | 53 (36, 73) | 72 (39, 121)* | 52 (43, 90) | 52 (31, 93) |
| TC (mg/dL) | 179 (152, 203) | 192 (162, 215)† | 184 (159, 215)† | 182 (158, 220)† |
| LDL-C (mg/dL) | 99 (82, 125) | 102 (72, 134) | 96 (72, 124) | 99 (71, 139)† |
| LDL-P (umol/L) | 1397 (1074, 1664) | 1256 (990, 1558) | 1365 (995, 1688) | 1230 (1013, 1592) |
| HDL-C (mg/dL) | 42 (35, 53) | 39 (33, 52)* | 39 (33, 47)* | 42 (33, 50) |
| HDL-P (umol/L) | 30 (25, 37) | 30 (26, 36)† | 30 (25, 36) | 30 (25, 34) |

Data are median (IQR).

HDL-P, total HDL particles; LDL-P, total LDL particles; VLDL-P, total VLDL particles; VLDL-TG, VLDL triglyceride.

*p < 0.05 for comparison with BL.

†p < 0.05 for comparison of change from BL vs. placebo.

TABLE 3

Acylcarnitine species in Patients treated with Compound 1 20 mg

| Acylcarnitine species | Treatment Group | PDFF Responders Median % Change from Baseline (IQR) | PDFF Nonresponders Median % Change from Baseline (IQR) | p-value Responders vs Nonresponders |
|---|---|---|---|---|
| palmitoleoylcarnitine (C16:1) | Compound 1 20 mg | −9.82 (−35.37, 14.13) | 31.63 (4.83, 71.13) | 0.0008 |
| | Compound 1 5 mg | −0.06 (−13.25, 21.94) | 18.13 (−13.98, 56.85) | 0.3685 |
| | Placebo | 109.44 (42.59, 687.74) | 3.017 (−24.16, 16.55) | 0.2676 |
| 5-dodecenoylcarnitine (C12:1) | Compound 1 20 mg | −12.39 (−39.16, 27.65) | 58.85 (20.88, 147.84) | 0.0009 |
| | Compound 1 5 mg | 2.08 (−10.45, 40.25) | 15.43 (−22.67, 70.49) | 0.6097 |
| | Placebo | 229.79 (133.19, 321.32) | 2.75 (−22.95, 38.29) | 0.0463 |
| laurylcarnitine (C12) | Compound 1 20 mg | −3.23 (−33.82, 24.31) | 36.72 (5.78, 65.13) | 0.0038 |
| | Compound 1 5 mg | 1.99 (−28.12, 18.13) | 15.23 (−16.4, 55.23) | 0.2987 |
| | Placebo | 206.76 (86.16, 293.08) | 8.92 (−17.35, 31.47) | 0.3094 |
| linolenoylcarnitine (C18:3) | Compound 1 20 mg | −17.84 (−39.68, 4.05) | 20.43 (−12.69, 47.07) | 0.0038 |
| | Compound 1 5 mg | 6.49 (−15.09, 45.56) | −23.55 (−43.47, 59.91) | 0.2734 |
| | Placebo | 0.19 (−17.04, 304.39) | −10.22 (−26.54, 28.95) | 0.6979 |
| myristoylcarnitine (C14) | Compound 1 20 mg | −19.99 (−32.83, 19.79) | 23.92 (1.48, 53.4) | 0.0038 |
| | Compound 1 5 mg | −7.50 (−27.16, 12.84) | 12.05 (−16.58, 33.41) | 0.2495 |
| | Placebo | 119.60 (43.761, 241.24) | −1.32 (−28.47, 25.05) | 0.1965 |
| myristoleoylcarnitine (C14:1) | Compound 1 20 mg | −7.22 (−40.18, 20.16) | 22.42 (14.66, 91.01) | 0.0049 |
| | Compound 1 5 mg | −4.71 (−29.19, 27.35) | 25.74 (−22.57, 53.45) | 0.3119 |
| | Placebo | 259.55 (106.34, 330.66) | −0.36 (−23.79, 27.74) | 0.3094 |
| octadecenedioylcarnitine (C18:1-DC) | Compound 1 20 mg | −11.01 (−63.06, 6.71) | 36.38 (−1.98, 217.21) | 0.0060 |
| | Compound 1 5 mg | 33.24 (13.71, 109.29) | 0 (−43.72, 33.93) | 0.0113 |
| | Placebo | 0 (0, 232.71) | 0 (−63.76, 93.64) | 0.4355 |

TABLE 3-continued

Acylcarnitine species in Patients treated with Compound 1 20 mg

| Acylcarnitine species | Treatment Group | PDFF Responders Median % Change from Baseline (IQR) | PDFF Nonresponders Median % Change from Baseline (IQR) | p-value Responders vs Nonresponders |
|---|---|---|---|---|
| 3-hydroxybutyrylcarnitine (1) | Compound 1 20 mg | −13.99 (−45.89, 22.16) | 34.27 (−8.85, 65.9) | 0.0085 |
| | Compound 1 5 mg | −18.06 (−40.74, −9.99) | −4.08 (−40.12, 61.86) | 0.2061 |
| | Placebo | 75.50 (6.23, 117.81) | −2.34 (−19.11, 31.51) | 0.573 |

Example 2a

Compound 2 and Fenofibrate: 14-Day Oral and Feed Pharmacology Study Using the Fast Food Diet Model of Fatty Liver in the Male C57B1/6 Mouse Purpose:

The purpose of this study is to assess the effect of Compound 2 on deuterium incorporation into plasma and liver TG and molecular biology of liver after 10 to 14 days of Compound 2 administration in a fast food diet-induced model on non-alcoholic steatosis in mice. Mice enrolled in this study were fed a fast food diet for approximately 9 months prior to study start. Primary endpoints will be deuterium incorporation into plasma TG, total plasma TG, and chromatin immunoprecipitation (IP) of PPARα, liver X receptor (LXR), and retinoic X receptor alpha (RXRα) from liver.

Animal Care and Use Statement:

All procedures in this Protocol are in compliance with the Animal Welfare Act, the Guide for the Care and Use of Laboratory Animals, and the Office of Laboratory Animal Welfare. In the opinion of the Sponsor and study director, the study does not unnecessarily duplicate any previous work, and no other model can fulfill the study requirements.

Test Details:

| Treatment Group | Number of Animals per Group | Number of Animals per Timepoint | Number of Dosing Days | Necropsy Time | Test Article | Dose (mg/kg) | Dose Volume (mL/kg) | Dosing Frequency (x/day) | Route |
|---|---|---|---|---|---|---|---|---|---|
| 1 | 30 | 10 | 10 | 24 hours postdose | Vehicle | 0 | 5 | QD | PO |
| | | 10 | 11 | 24 hours postdose | | | | | |
| | | 10 | 14 | 2 hours postdose | | | | | |
| 2 | 30 | 10 | 10 | 24 hours postdose | Cmpd 2 | 10 | 5 | QD | PO |
| | | 10 | 11 | 24 hours postdose | | | | | |
| | | 10 | 14 | 2 hours postdose | | | | | |
| 3 | 20 | 10 | 11 | 24 hours postdose | Cmpd 2 + Fenofibrate | 10 0.1% in diet | 5 NA | QD Ad libitum | PO In Diet |
| | | 10 | 14 | 2 hours postdose | | | | | |
| 4 | 17 | 8 | 10 | 24 hours postdose | Cmpd 2 | 10 | 5 | QD | PO |
| | | 9 | 10 | Day 16 | | | | | |
| 5 | 10 | 10 | NA | Day 11 | NA | NA | NA | NA | NA |

NA = Not Applicable

Vehicle: 0.5% sodium carboxymethylcellulose (medium viscosity), 1% ethanol, 98.5% 50 mM tris buffer, pH 8 ± 0.5 in reverse osmosis water (or equivalent)

Compound 2 (Cmpd 2): in vehicle solution (pH: between 7.5 and 8.5).

Fenofibrate: 0.1% milled in diet.

Fast food and standard diet mice will be randomized to treatment groups based on body weights collected on Day 1.

Fructose/glucose water

Predose Phase

Animals 1 through 98: Fructose/glucose water

Animals 99 through 108: city water ad libitum

Dosing phase

Groups: 1 through 4: Fructose/glucose water

Group 5: city water ad libitum $^2H_2O$ (Deuterium Oxide-Heavy Water):

$^2H_2O$ bolus injection: dose each animal in Groups 1 through 3 $^2H_2O$ on Day 10 at 25 mL/kg intra-peritoneal (IP) injection. $^2H_2O$ dose will follow Compound 2, if applicable.

$^2H_2O$ in the drinking water: dose each animal in Groups 1 through 3 $^2H_2O$ Day 10 through study direction immediately following IP injection.

Whole blood sample are collected during experiments. Livers will be observed and tissue samples will be collected. Animals will be fasted approximately 4 to 6 hours prior to each respective blood draw and scheduled sacrifice.

Example 2b

Once daily Compound 2 and Fenofibrate administered in chow: 14-day Pharmacology Study Using the Fast Food Diet Model of Fatty Liver in the Male C57B1/6 Mouse Purpose:

The purpose of this study was to assess the effect of Compound 2 on plasma and liver TG and molecular biology of liver after 10 to 14 days of Compound 2 administered orally (10 mg/kg QD), or fenofibrate (0.1% administration in chow), or the combination in a mice fed a diet high in fat, cholesterol, and fructose (the fast-food diet, FFD). Mice enrolled in this study were fed a fast food diet for approximately 9 months prior to study start. Primary endpoints were plasma triglycerides, liver triglycerides, liver cholesterol, and hepatic gene expression of liver X receptorα (LXRα), and sterol response element binding protein-1c (SREBP1c) target genes by qPCR.

Animal Care and Use Statement:

All procedures in this Protocol are in compliance with the Animal Welfare Act, the Guide for the Care and Use of Laboratory Animals, and the Office of Laboratory Animal Welfare. In the opinion of the Sponsor and study director, the study does not unnecessarily duplicate any previous work, and no other model can fulfill the study requirements.

Table 4: Test Details

| Treatment Group | Number of Animals per Group | Number of Animals per Timepoint | Number of Dosing Days | Necropsy Time | Test Article | Dose (mg/kg) | Dose Volume (mL/kg) | Dosing Frequency (x/day) | Route |
|---|---|---|---|---|---|---|---|---|---|
| 1 | 30 | 10 | 10 | 24 hours postdose | Vehicle | 0 | 5 | QD | PO |
|   |    | 10 | 11 | 24 hours postdose |         |   |   |    |    |
|   |    | 10 | 14 | 2 hours postdose  |         |   |   |    |    |
| 2 | 30 | 10 | 10 | 24 hours postdose | Cmpd 2  | 10 | 5 | QD | PO |
|   |    | 10 | 11 | 24 hours postdose |         |    |   |    |    |
|   |    | 10 | 14 | 2 hours postdose  |         |    |   |    |    |
| 3 | 20 | 10 | 11 | 24 hours postdose | Cmpd 2 + Fenofibrate | 10 0.1% in diet | 5 NA | QD Ad libitum | PO In Diet |
|   |    | 10 | 14 | 2 hours postdose  |         |    |    |    |    |

NA = Not Applicable
Vehicle: 0.5% sodium carboxymethylcellulose (medium viscosity), 1% ethanol, 98.5% 50 mM tris buffer, pH 8 ± 0.5 in reverse osmosis water (or equivalent)
Compound 2 (Cmpd 2): in vehicle solution (pH: between 7.5 and 8.5).
Fenofibrate: 0.1% milled in diet.
Fast food and standard diet mice will be randomized to treatment groups based on body weights collected on Day 1.
Fructose/glucose water
Predose Phase
Animals 1 through 80: Fructose/glucose water
Dosing phase
All Groups: Fructose/glucose water
Whole blood sample were collected during the in-life phase of the study and livers were collected at termination. Animals were fasted approximately 4 to 6 hours prior to each respective blood draw and scheduled sacrifice.

Figure 4:
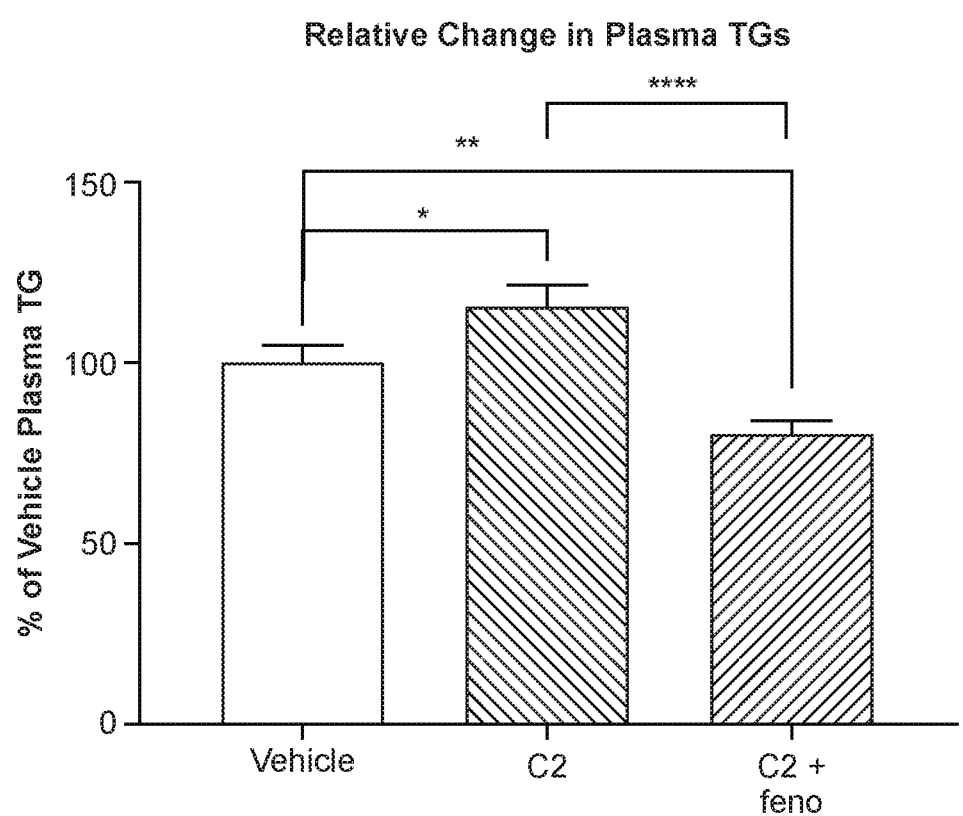
FIG. 4 shows the relative change in plasma triglycerides in the studied animals. Values are expressed as percent of vehicle-treated animals collected at the same time of day after treatment with vehicle, Compound 2 ("C2"), and Compound 2 in combination with fenofibrate ("C2+feno"). $*p \leq 0.05, p \leq 0.01, **p \leq 0.0001$ and n=27-38 sampled from 8-13 animals per treatment group. Data presented as mean±SEM.
Figure 5A:
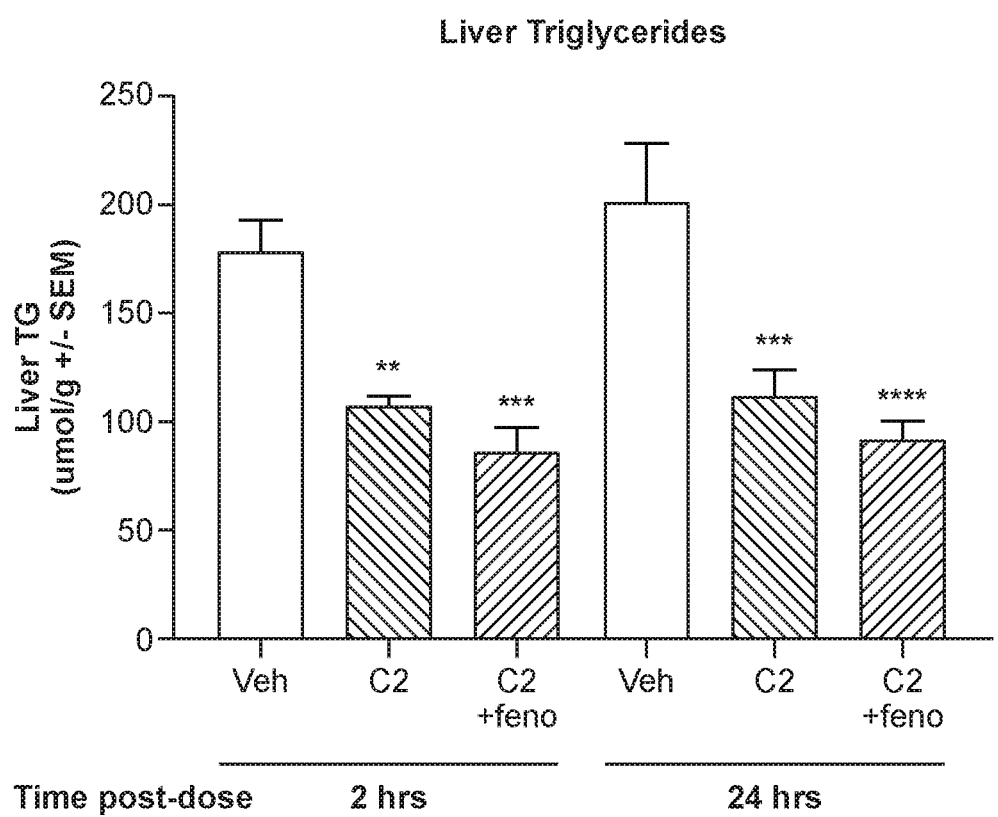
FIG. 5A, FIG. 5B, and FIG. 5C show levels of liver triglyceride, liver cholesterol, and plasma ketone bodies, respectively, at 2 hours or 24 hours post-dose in animals treated with vehicle ("Veh"), Compound 2 ("C2"), and Compound 2 in combination with fenofibrate ("C2+feno"). ns=not significant. $p \leq 0.01, *p \leq 0.001, ****p \leq 0.0001$ compared to vehicle-treated mice, and $\#p \leq 0.05, \#\#\#p \leq 0.001, \#\#\#p \leq 0.0001$ compared to Compound 2-treated mice by unpaired student's t-test; n=7-20 sampled from 7-10 animals per treatment group. Data presented as mean±SEM.
Figure 5B:
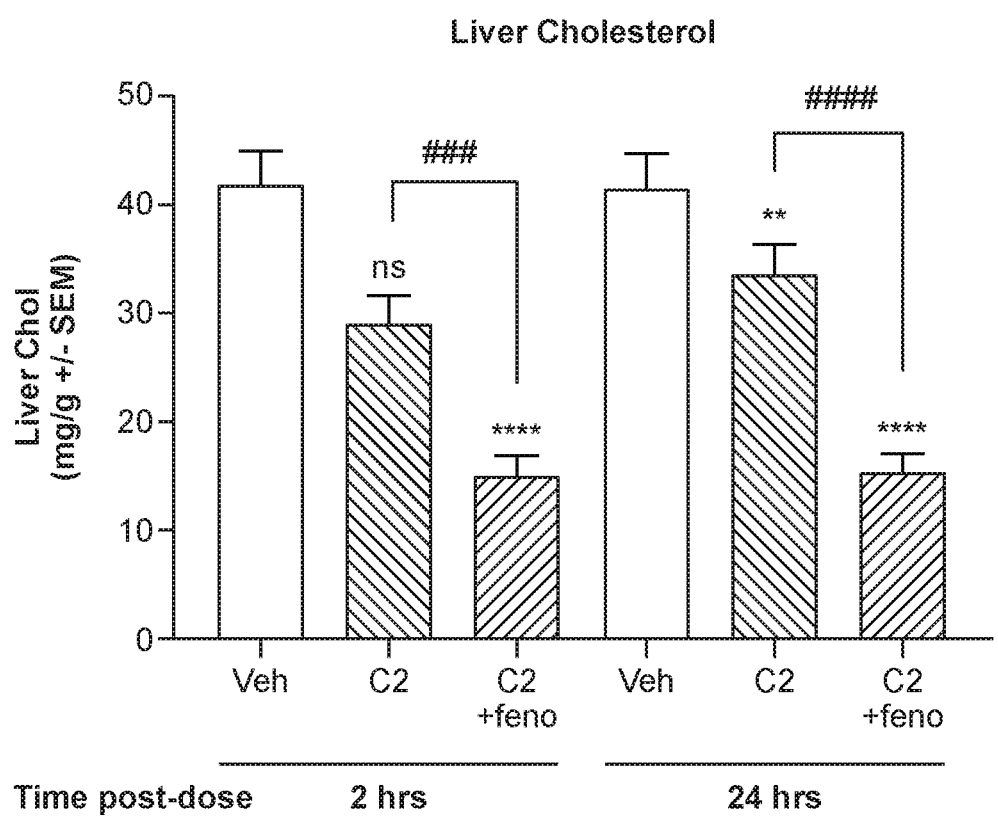
Figure 5C:
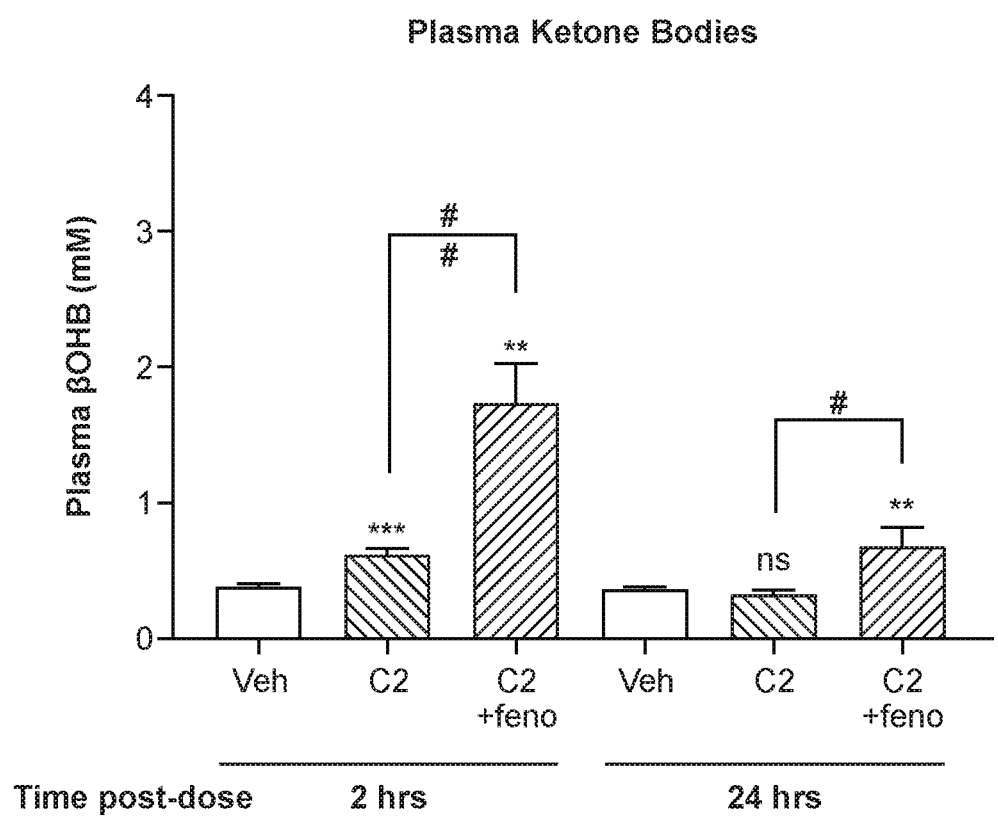
Figure 6A:
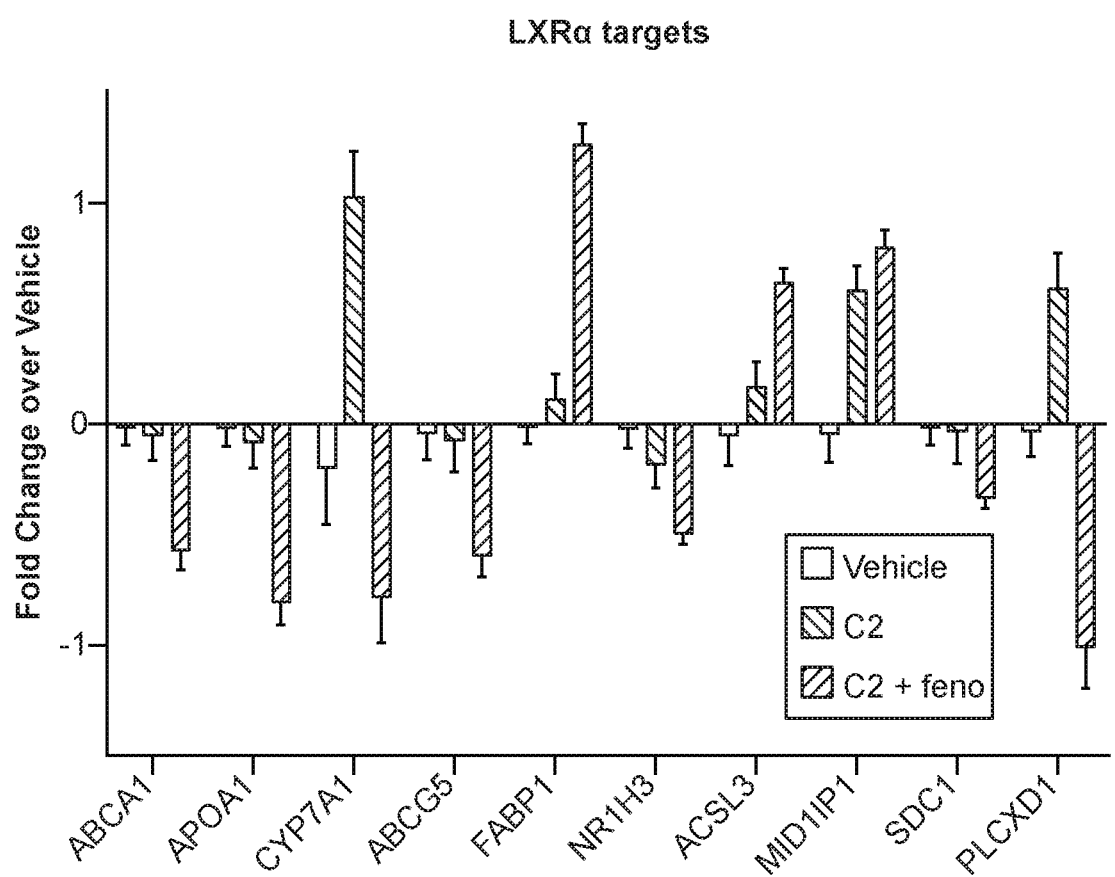
FIG. 6A and FIG. 6B show LXRα and SREBP1c targets respectively, in animals treated with vehicle, Compound 2 ("C2") or Compound 2 in combination with fenofibrate ("C2+feno").
Figure 6B:
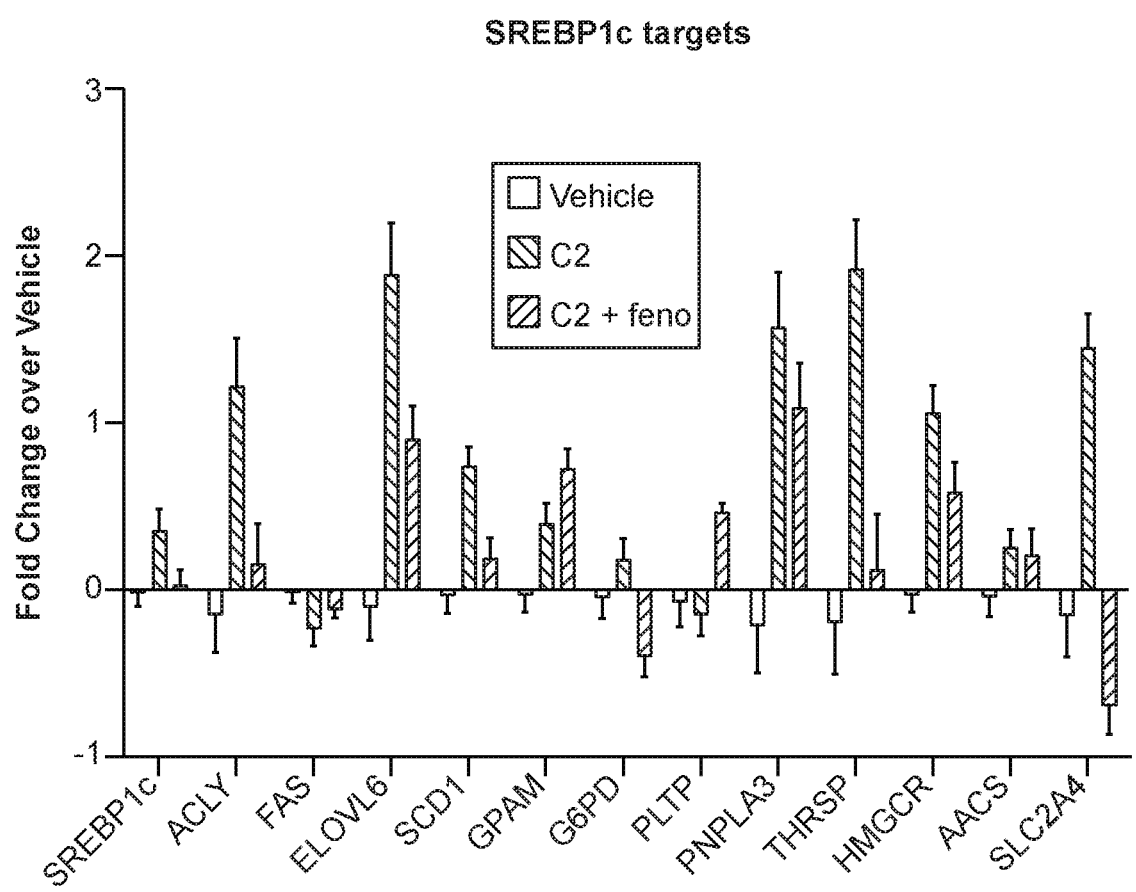

After two weeks of dosing Compound 2 in this model, plasma triglycerides were significantly increased by 15% relative to vehicle-treated animals, whereas coadministration of fenofibrate in chow with Compound 2 significantly reduced plasma triglycerides relative to both the Compound 2-treated group and the vehicle control group (see FIG. 4). Treatment with Compound 2 was associated with increased expression of target genes, and addition of fenofibrate with Compound 2 was associated with reduced expression of LXRα and SREBP1 target gene expression (FIG. 6A-B). It is thus contemplated that LXRα/SREBP1 activation and PPARα reduction may be required for ACC inhibitor, Compound 2 ("C2")-mediated hypertriglyceridemia. The addition of fenofibrate did not impact the C2-induced reduction of liver triglycerides, but significantly further decreased liver cholesterol (see FIGS. 5A and 5B). Plasma βOHB was significantly increased after 14 days of Compound 2 treatment in this mouse model, and was significantly further increased with addition of fenofibrate (see FIG. 5C).

Conclusions:

The data demonstrates that co-administration of Compound 2 with a PPARα agonist can ameliorate plasma hypertriglyceridemia induced by ACC inhibition.

Example 3

Compound 1 in Patients with Compensated Cirrhosis Due to NASH

Methods:

In a proof-of-concept study, 10 subjects with suspected compensated cirrhosis (Child-Turcotte-Pugh [CTP]-A) due to NASH (defined by any one of biopsy, liver stiffness by magnetic resonance elastography [MRE]≥4.67 kPa or transient elastography ≥14.0 kPa, or Fibrotest ≥0.75) received Compound 1 20 mg orally once daily for 12 weeks. Centrally-read magnetic resonance imaging-proton density fat fraction (MRI-PDFF) and MRE, and serum markers of fibrosis were measured at baseline (BL), Week 4 (W4), and Week 12 (W12). For DNL determination, heavy water ($^2H_2O$, 35 mL) was administered three times daily for one-week cycles prior to baseline, W4, and W12. Deuterium incorporation into palmitate was measured in fasting plasma samples by GC/MS, and mass isotopomer distribution analysis was used to calculate hepatic DNL and its inhibition by Compound 1.

Figure 2:
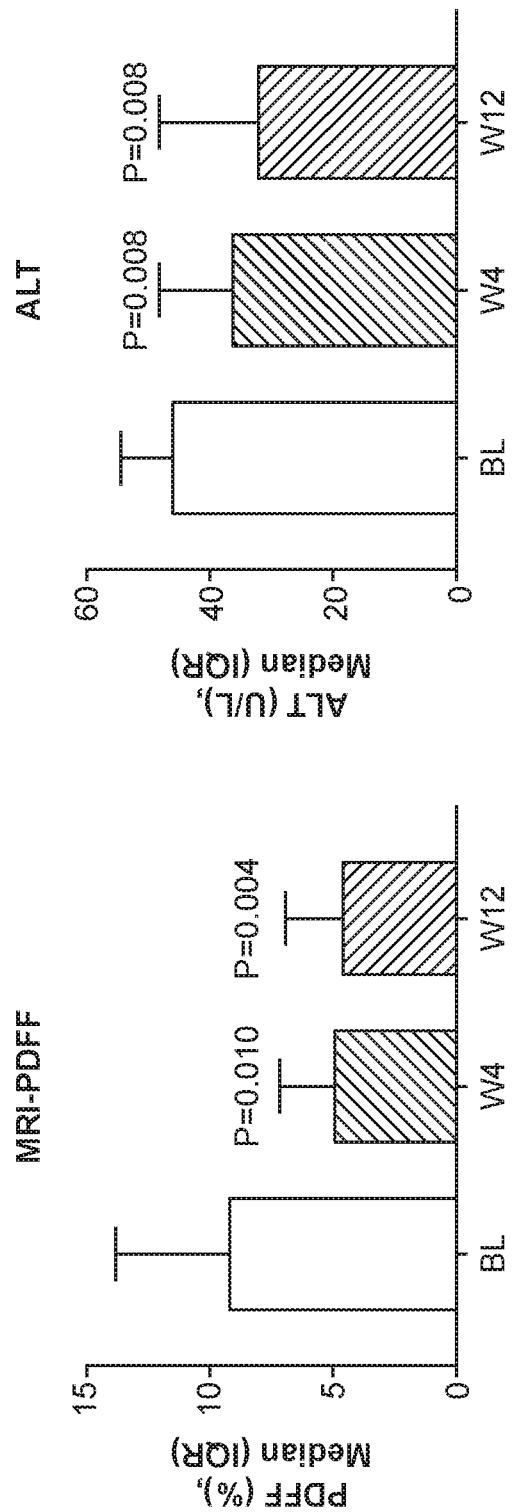
FIG. 2 illustrates changes in MRI-PDFF and ALT during Compound 1 treatment in subjects with compensated cirrhosis due to NASH. BL refers to baseline, W4 refers to week 4, and W12 refers to week 12.

Results:

Compared to BL, statistically significant reductions in hepatic PDFF (median: 9.2 vs. 4.6%; P=0.004) and serum ALT (46 vs. 32 U/L; P=0.008; FIG. 2) were observed after 12 weeks of Compound 1 treatment. Reductions in PDFF were significant by W4. A ≥30% relative decline was seen in 5 subjects at W4 (50%) and 7 subjects (70%) at W12. No significant changes in MRE-stiffness or serum fibrosis markers were observed. Decreases in PDFF correlated with changes in ALT, ELF score, and PIII-NP. Compound 1 was well-tolerated; no subjects prematurely discontinued study medication. Median (IQR) fasting triglycerides increased from 147 mg/dL (105, 231) at BL to 159 mg/dL (142, 248) at W12 (P=0.008), but other lipid parameters were unchanged. One subject had asymptomatic Grade 3 hypertriglyceridemia and responded to fibrate therapy. Data regarding the impact of Compound 1 on fasting hepatic DNL are pending.

Conclusion:

In a proof-of-concept study, 12-week therapy with the liver-targeted, oral Compound 1 in subjects with compensated cirrhosis due to NASH was safe and associated with significant improvements in hepatic steatosis and serum ALT.

Example 4

Compound 1 in Patients

Ten subjects with steatosis (MRI-PDFF ≥10%) and F1-F3 fibrosis (MRE ≥2.88 kPa but non-cirrhotic based on FibroText <0.75, historical imaging and liver biopsy) were treated 20 mg Compound 1 for 12 weeks.

Four of the ten subjects were on fish oil or fenofibrate at baseline and continued the concomitant medication for the duration of the study. Throughout the study subjects were monitored for safety (adverse events, laboratory abnormalities), liver biochemistry, serum markers of fibrosis (ELF and its components TIMP-1, hyaluronic acid, PIII-NP) and cell death (CK18 M30 and M65), liver stiffness (MRE) and fat (MRI-PDFF) and the effect on de novo lipogensis was assessed using heavy water labeling.

Figure 7:
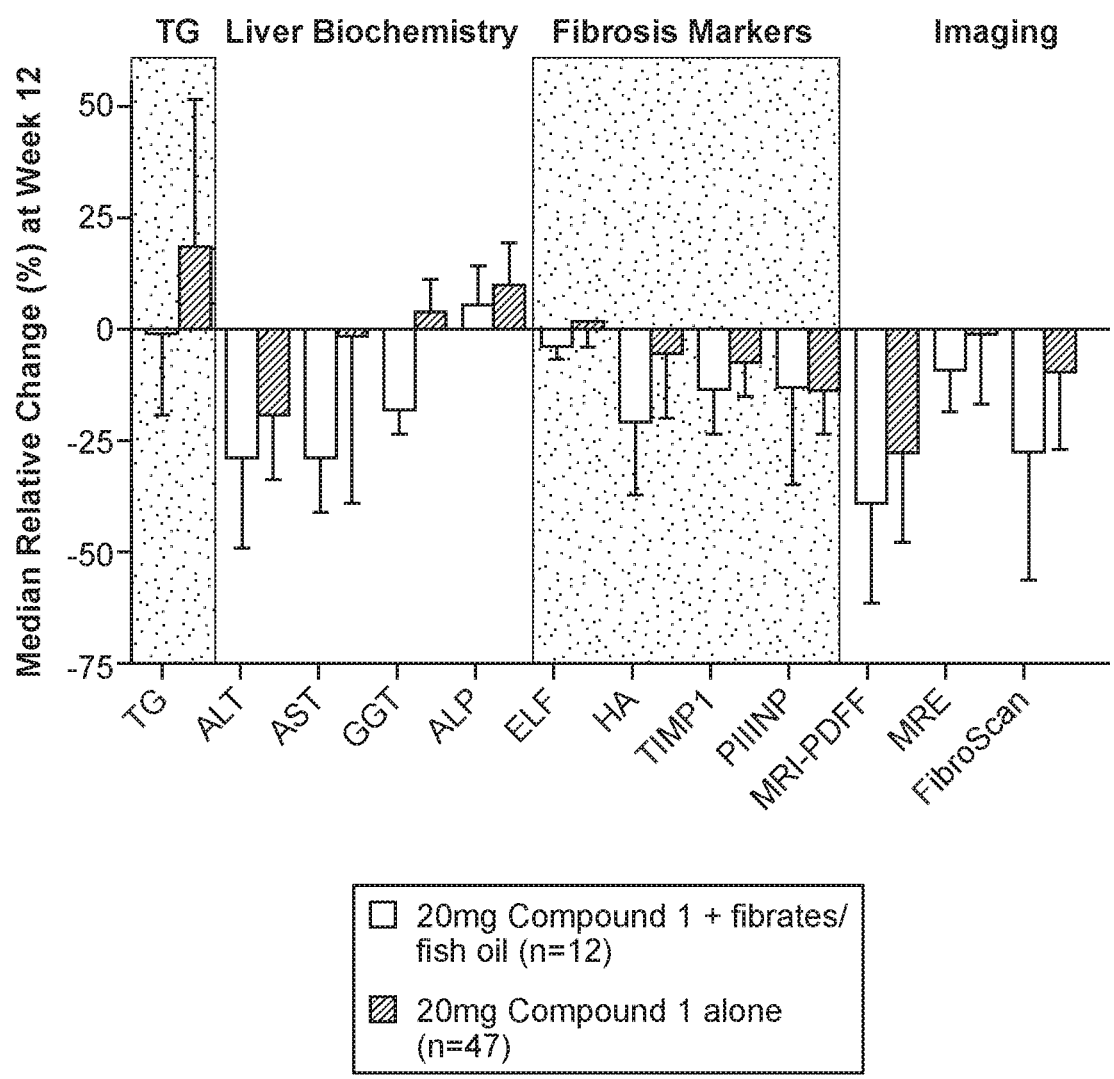
FIG. 7 shows median relative change (%) at week 12 of imaging, liver biochemistry, serum markers of fibrosis, and triglycerides levels of subjects administered 20 mg Compound 1 and fibrates/fish oil (left column) as compared to 20 mg Compound 1 alone (right column) as described in Example 4.

The four subjects were analyzed in conjunction with eight subjects from the study described in Example 1. These twelve subjects were on fish oil or fibrates for at least six weeks of the study and included those who were on fish oil or fibrates at baseline or who had graded hypertriglyceridemia and were given fish oil or fibrates during the study. The results are summarized in Table 6 and FIG. 7.

TABLE 6

Compound 1 and fibrate/fish oil shows improved efficacy

| Median Relative Change Over 12 Weeks | | Compound 1 20 mg (n = 59) | Compound 1 without Fibrate/Fish Oil (n = 47) | Compound 1 + Fibrate/Fish Oil (n = 12) |
|---|---|---|---|---|
| Imaging | MRI-PDFF | −31.0 (−48.6, −12.6) | −27.9 (−47.8, 1.7) | −39.1 (−61.6, −24.3) |
| | ≥30% reduction in MRI-PDFF, % (n) | 49% (29) | 43% (20) | 75% (9) |
| | MRE | −6.6 (−16.58) | −3.2 (−16.4, 9.6) | −9.1 (−18.8, −6.5) |
| | FibroScan† | −11.1 (−34.8, 13.7) | −9.8 (−26.9, 15.0) | −28.2 (−56.7, 4.4) |
| Liver Biochemistry | ALT | −21.9 (−40.1, 7.8) | −19.4 (−35.8, 8.7) | −29.1 (−49.4, −10.1) |
| Serum Markers of Fibrosis | ELF | −0.8 (−4.5, 3.0) | −0.35 (−3.9, 3.0) | −4.0 (−6.9, 4.7) |
| | TIMP-1 | −8.8 (−17.2, 1.4) | −7.85 (−16.3, 5.5) | −13.6 (−23.7, 4.0) |
| | PIII-NP | −13.9 (−24.6, 12.3) | −13.9 (−23.9, 10.8) | −13.2 (−35.2, 16.9) |
| | Hyaluronic acid | −5.9 (−21.7, 43.3) | −4.5 (−17.6, 43.3) | −20.8 (−37.2, 57.0) |
| Metabolic Parameters | Hemoglobin A1c | −1.4 (−6.2, 3.1) | −1.4 (−5.5, 3.7) | −3.7 (−9.6, 1.8) |
| | Fasting Glucose | −2.0 (−11.9, 8.2) | −1.9 (−12.1, 8.1) | −5.0 (−19.4, 28.0) |
| | Triglycerides | 10.8 (−3.8, 45.9) | 14.3 (−2.2, 49.7) | −1.2 (−19.5, 43.0) |
| | >Grade 3 TGs, % (n) | 29% (17) | 33% (16) | 8% (1*) |

Continuous data are median (IQR);
Fibrate/Fish Oil for >6 weeks;
*Patient started fenofibrate after week 1;
†Only in Phase 2 study described in Example 1, n = 6 for Compound 1 + Fibrate/Fish Oil.

As shown in Table 6, nearly all the imaging, liver biochemistry, serum markers of fibrosis, and metabolic parameters data demonstrate the improved efficacy of Compound 1 combined with a PPARα agonist (fenofibrate or fish oil) as compared to Compound 1 alone; PIII-NP is similar among the 3 treatment groups.

Figure 8A:
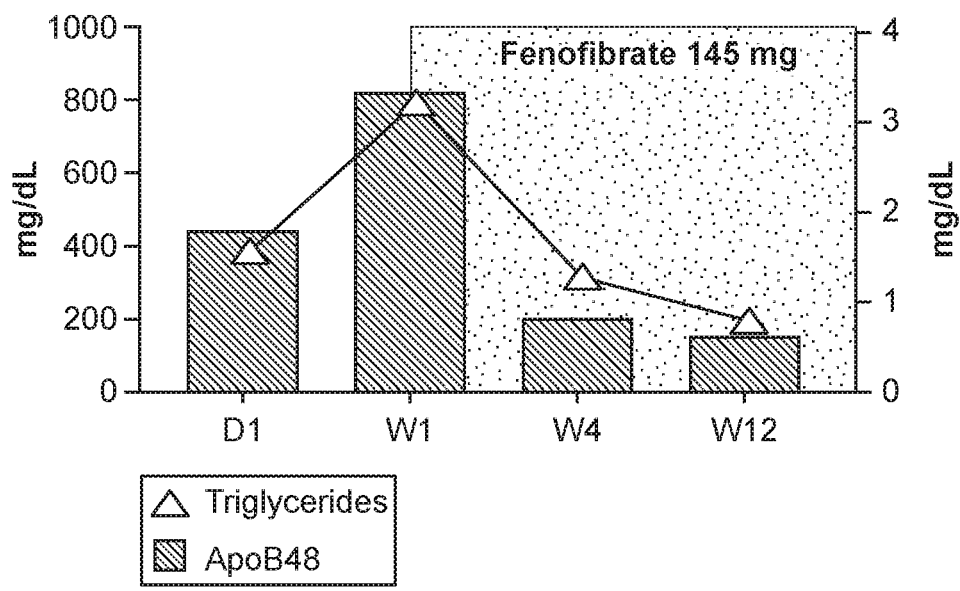
FIG. 8A shows triglyercides and ApoB48 of a patient administered 145 mg fenofibrate after having grade 3 hypertriglyceridemia at week 1.
Figure 8B:
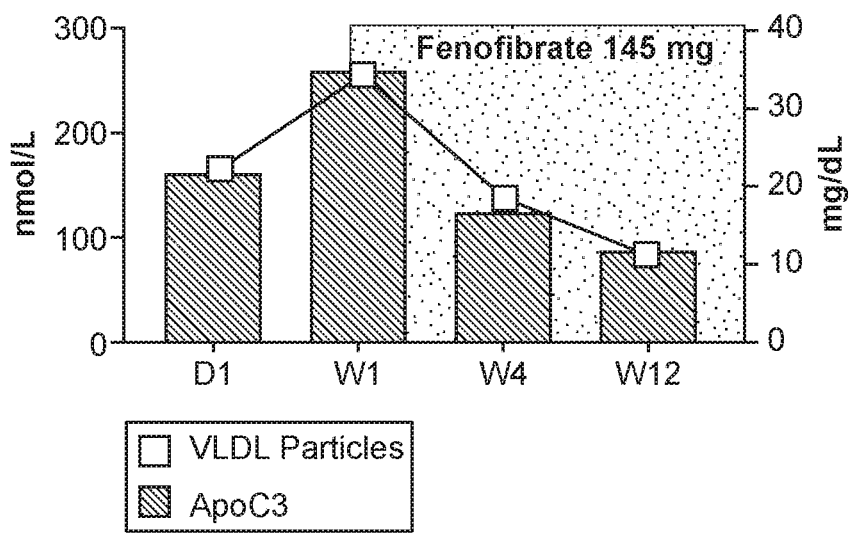
FIG. 8B shows VLDL particle levels and ApoC3 of a patient administered 145 mg fenofibrate after having grade 3 hypertriglyceridemia at week 1.

One of these twelve subjects was administered 145 mg fenofibrate after having grade 3 hypertriglyceridemia at week 1. All monitored TG related measurements (total TG, apolipoprotein B48 ("APOB48"), VLDL-P and apolipoprotein C3 ("APOC3")) improved to less than baseline following intervention with fenofibrate (FIGS. 8A and 8B). The data suggests that PPARα agonists may enhance efficacy and negate the increase in triglycerides.

Example 5

Compound 1 in Patients with NASH

Subjects that are not on pre-existing fibrates or fish oil and, including those exhibit F3-F4 NASH fibrosis with compensated liver function (which may be determined by noninvasive markers and historical biopsy within 6 months of screening), are administered 20 mg of Compound 1 and fenofibrate given at a dosage strength (e.g., 145 mg). Some subjects (approximately 75%) with triglycerides >250 mg/dL may be enrolled but subjects with triglicerides of >750 mg/dL may be excluded. Liver biochemistry (ALT, AST, GGT), serum markers of fibrosis (e.g, ELF and its components) and metabolism (e.g., HBA1C, insulin, glucose, acylcarnitines), and imaging (e.g., MRI-PDFF, MRE, Fibroscan) are measured at various time intervals, such as Week 0, 4, 8, 12, and week 24.

Example 6

Once Daily Oral Administration of Compound 2 and Fenofibrate: 15-Day Pharmacology Study Using the Fast Food Diet Model of Fatty Liver in the Male C57BL/6 Mouse Purpose:

The purpose of this study was to assess the effect of Compound 2 on plasma and liver triglycerides (TG) and molecular biology of liver after 15 days of oral administration ("PO") of Compound 2 (5 mg/kg QD), fenofibrate (25 mg/kg and 50 mg/kg QD), or the combination (Compound 2 (5 mg/kg, QD)+fenofibrate (50 mg/kg, QD)) in mice fed a diet high in fat, cholesterol, and fructose (the fast-food diet, FFD (Research Diet D12079B)). Mice enrolled in this study were fed a FFD for approximately 9 months prior to study start. Primary endpoints were plasma TG, liver TG, liver ketone bodies, plasma liver enzymes, hepatic oxidative stress and hepatic gene expression of liver X receptora (LXRα) and PPARα targets, and profibrotic markers by qPCR.

Figure 9:
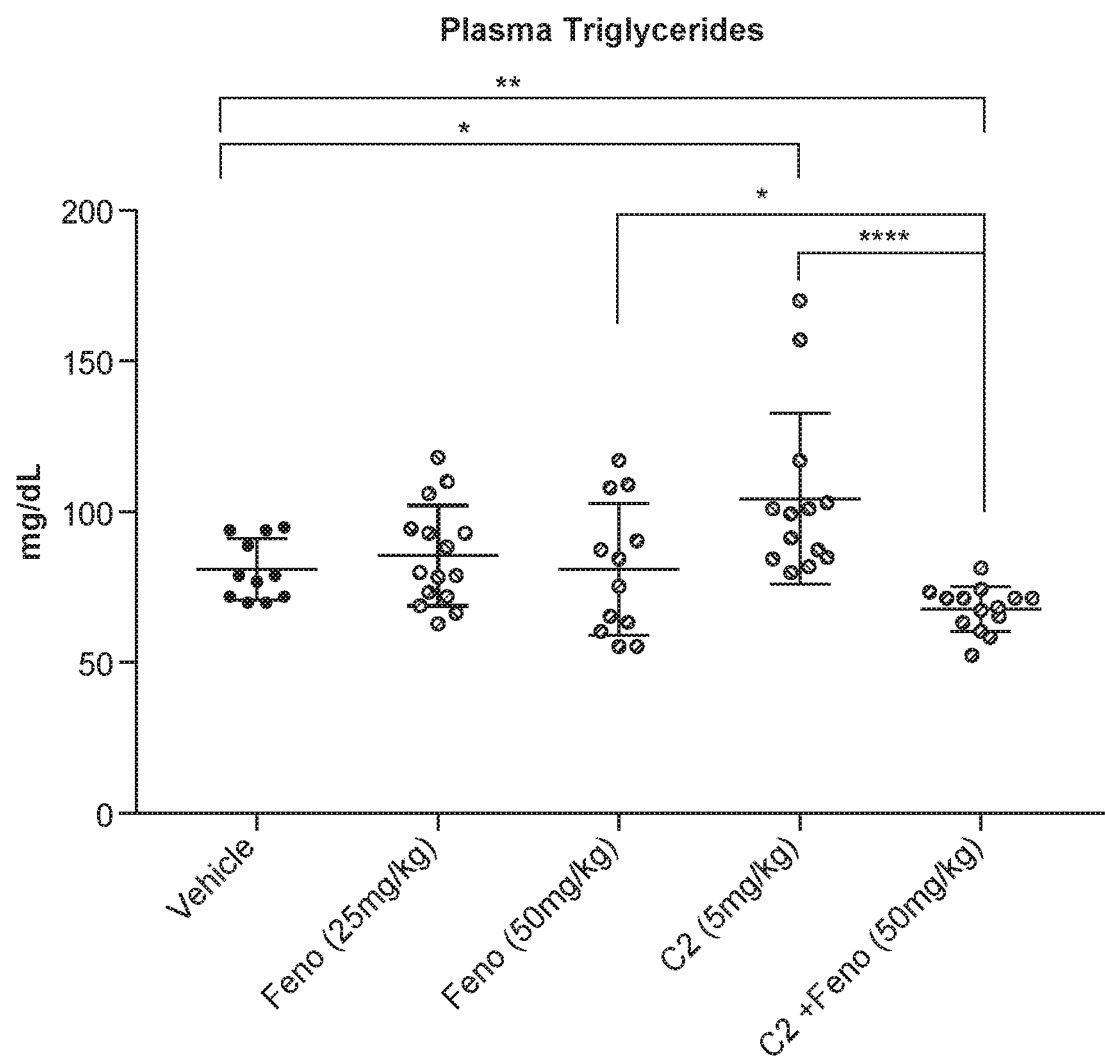
FIG. 9 shows the change in plasma triglycerides at 2 hours post-dose in ad lib fed fast food diet (FFD) mice treated with vehicle, single agent fenofibrate ("Feno (25 mg/kg)" and "Feno (50 mg/kg)") and Compound 2 ("C2 (5 mg/kg)"), and Compound 2 in combination with fenofibrate (50 mg/kg) ("C2+Feno (50 mg/kg)") for 15 days. $*p \leq 0.05, p \leq 0.01, *p \leq 0.001, ****p \leq 0.0001$ and n=11-15 animals per treatment group. Data presented as mean±SD.
Figure 10B:
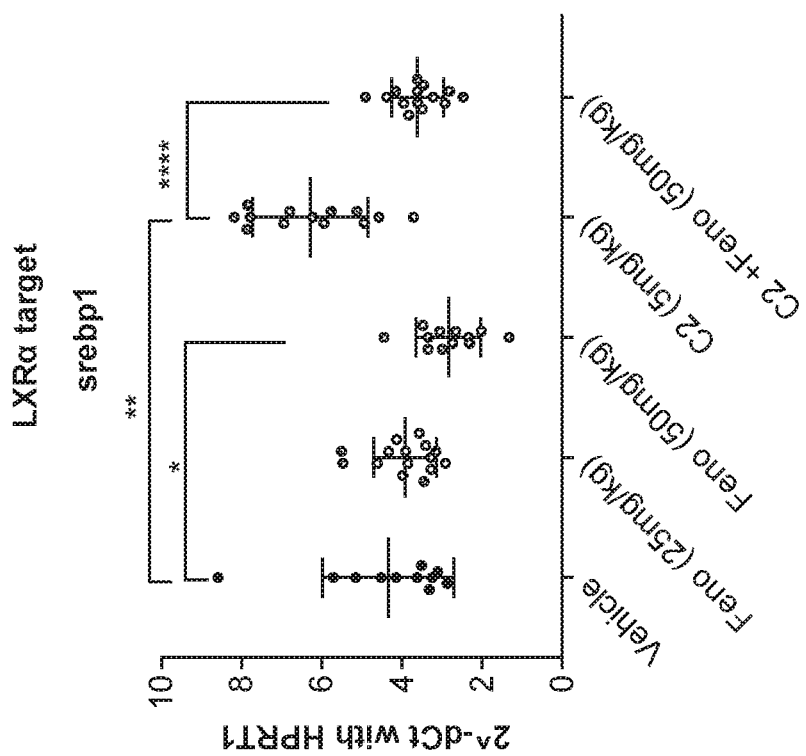
FIGS. 10A and 10B show hepatic mRNA expression of PPARα and LXRα targets, respectively, in animals treated with vehicle, single agent fenofibrate ("Feno (25 mg/kg)" and "Feno (50 mg/kg)") and Compound 2 ("C2 (5 mg/kg)"), and Compound 2 in combination with fenofibrate (50 mg/kg) ("C2+Feno (50 mg/kg)") for 15 days. $*p \leq 0.05, p \leq 0.01, *p \leq 0.001, ****p \leq 0.0001$ and n=11-15 animals per treatment group. Data presented as mean±SD.
Figure 10A:
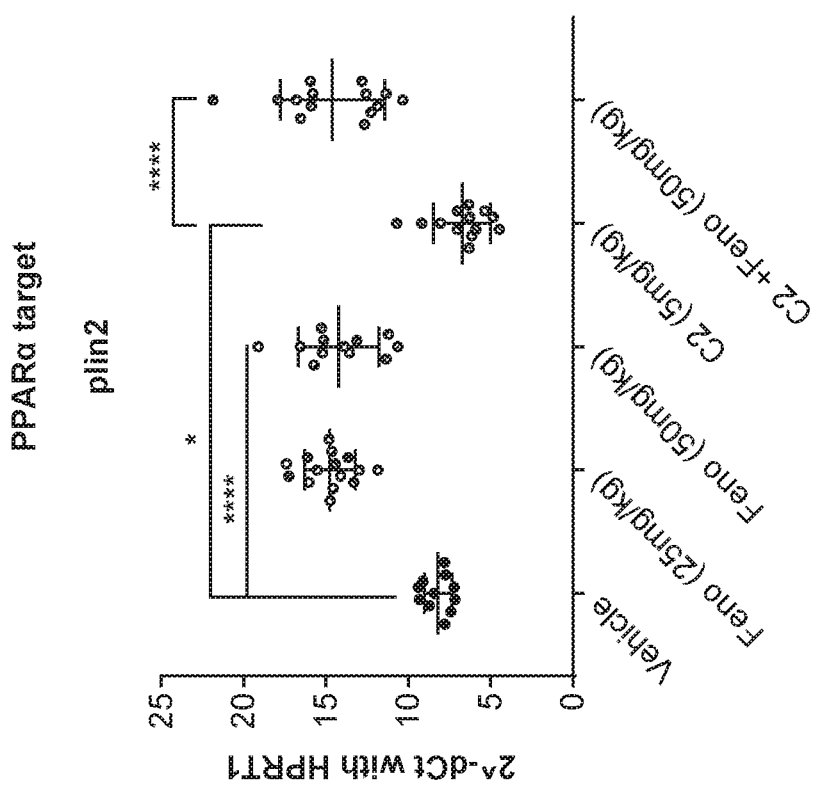
Figures 11A, 11B:
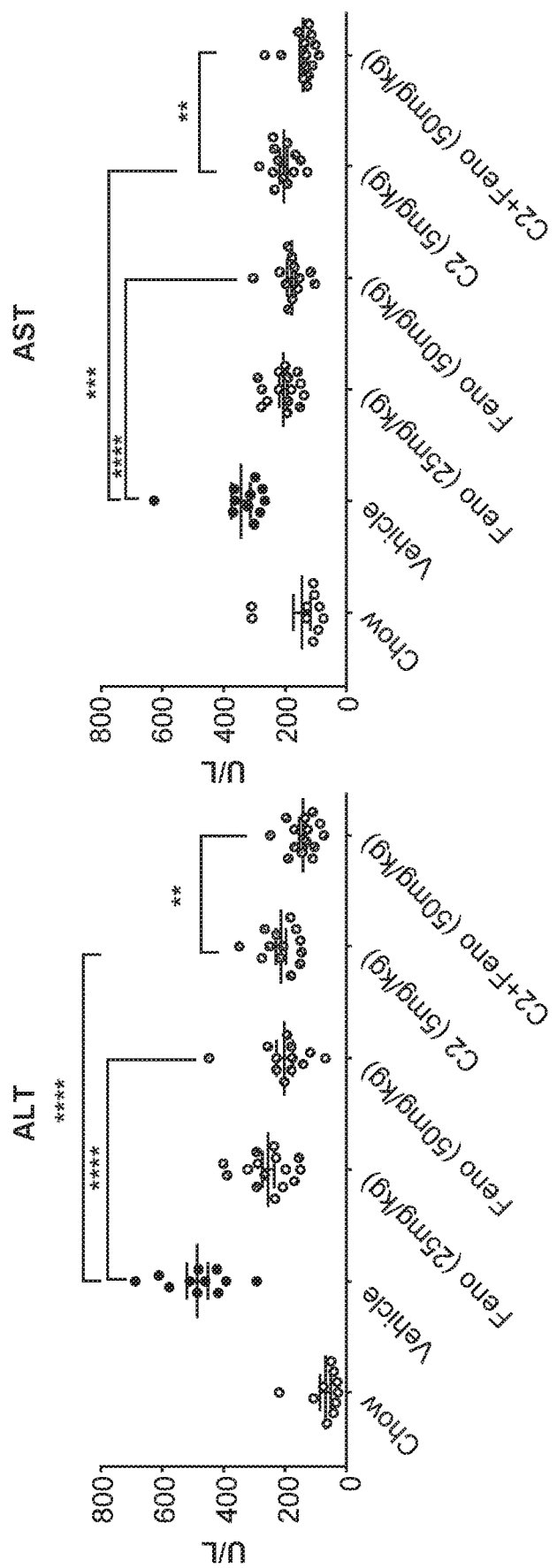
FIGS. 11A and 11B show plasma ALT and AST levels, respectively, in animals fed a standard diet (chow), or FFD treated for 15 days with vehicle, single agent fenofibrate ("Feno (25 mg/kg)" and "Feno (50 mg/kg)") and Compound 2 ("C2 (5 mg/kg)"), and Compound 2 in combination with fenofibrate (50 mg/kg) ("C2+Feno (50 mg/kg)"). $*p \leq 0.05, p \leq 0.01, *p \leq 0.001, ****p \leq 0.0001$ and n=10-15 animals per treatment group. Data presented as mean±SEM.
Figure 12B:
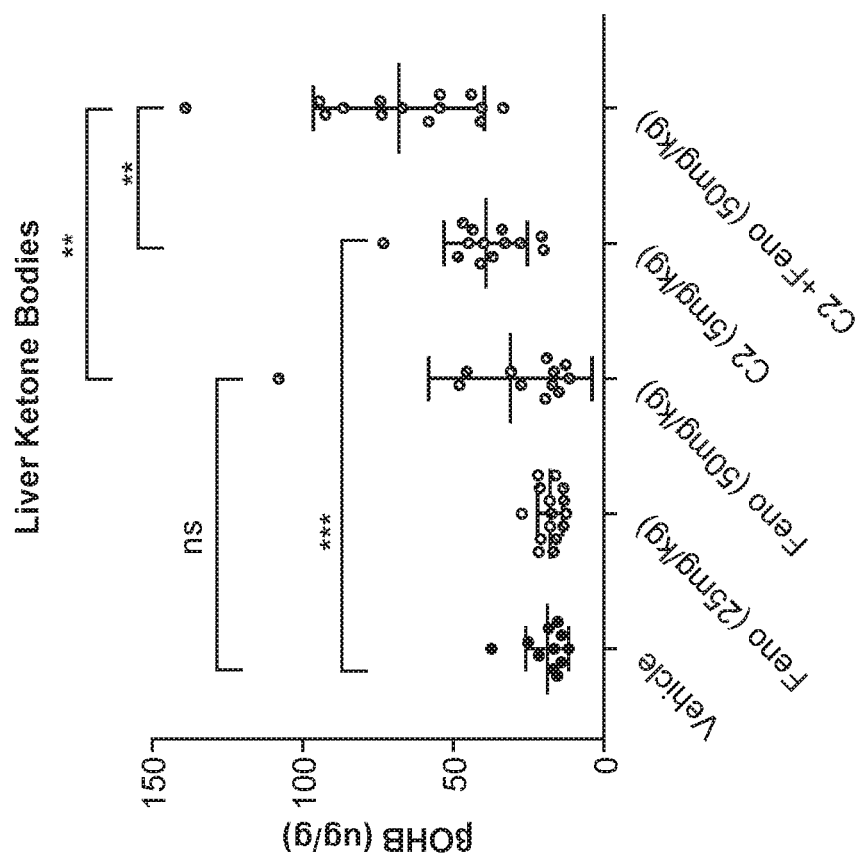
FIGS. 12A and 12B show levels of liver triglycerides and liver ketone bodies (βOHB), respectively, at 2 hours post-dose in animals treated with vehicle, single agent fenofibrate ("Feno (25 mg/kg)" and "Feno (50 mg/kg)") and Compound 2 ("C2 (5 mg/kg)"), and Compound 2 in combination with fenofibrate (50 mg/kg) ("C2+Feno (50 mg/kg)") for 15 days. $*p \leq 0.05, p \leq 0.01, *p \leq 0.001, ****p \leq 0.0001$, ns=not significant and n=11-15 animals per treatment group. Data presented as mean±SD.
Figure 12A:
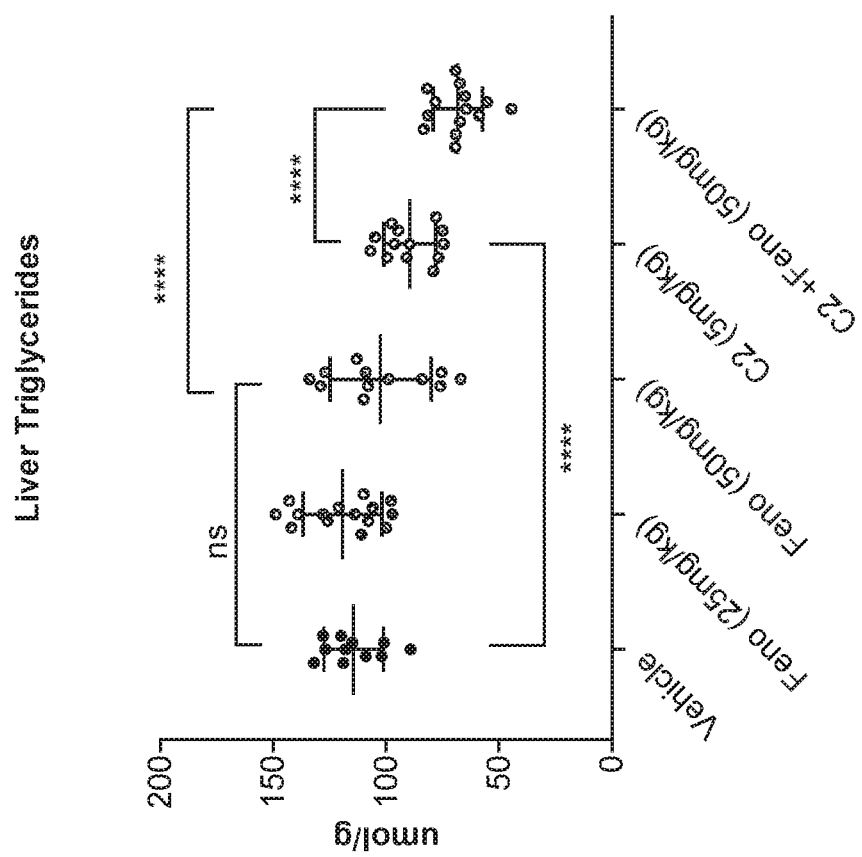
Figure 13:
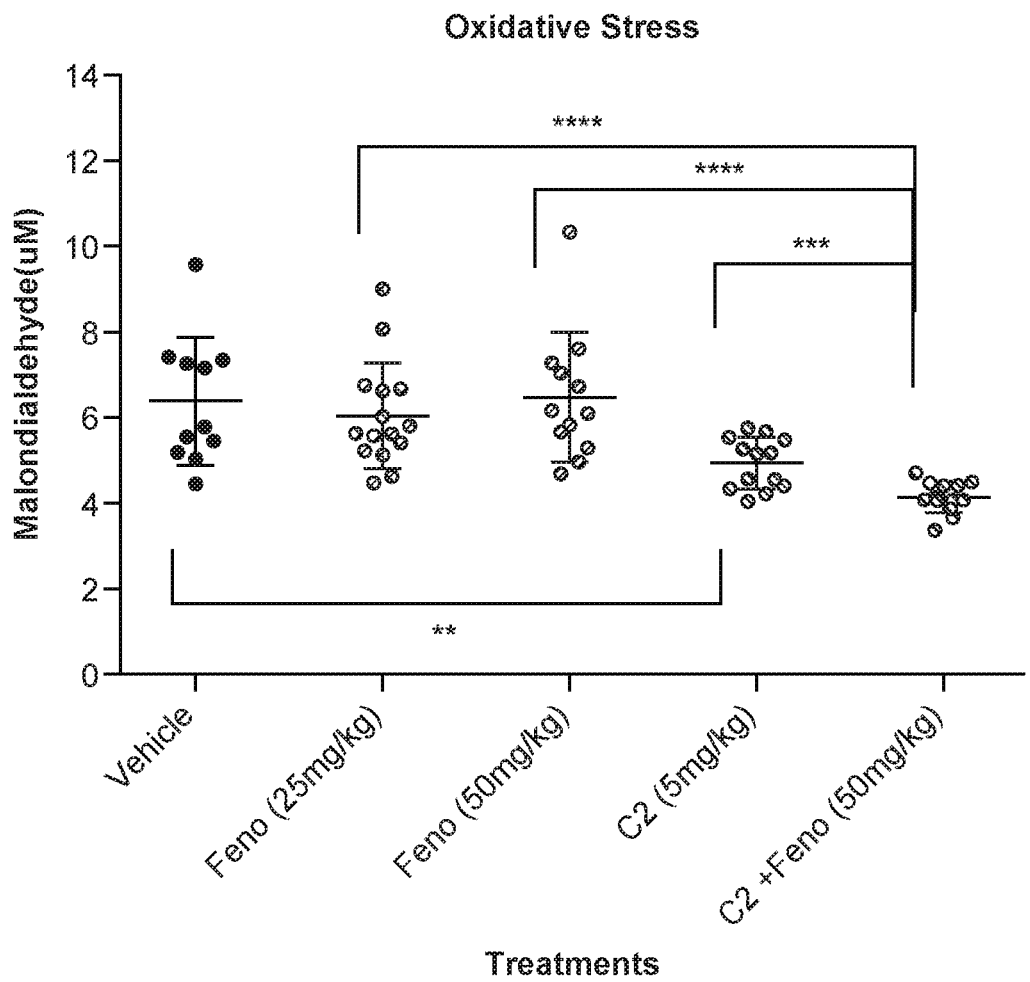
FIG. 13 shows oxidative stress quantified as amount of malondialdehyde in livers of animals treated with vehicle, single agent fenofibrate ("Feno (25 mg/kg)" and "Feno (50 mg/kg)") and Compound 2 ("C2 (5 mg/kg)"), and Compound 2 in combination with fenofibrate (50 mg/kg) ("C2+Feno (50 mg/kg)") for 15 days. $*p \leq 0.05, p \leq 0.01, *p \leq 0.001, ****p \leq 0.0001$ and n=11-15 animals per treatment group. Data presented as mean±SD.
Figure 14B:
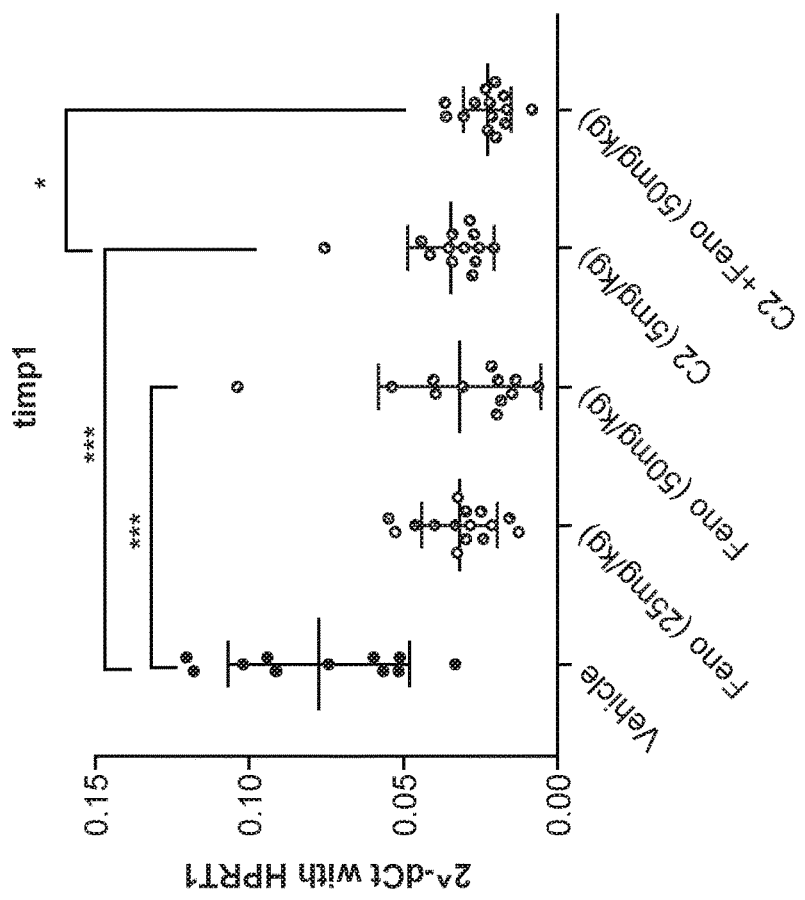
FIGS. 14A and 14B show mRNA expression of pro-fibrotic genes col1a1 and timp1, respectively, in livers of animals treated with vehicle, single agent fenofibrate ("Feno (25 mg/kg)" and "Feno (50 mg/kg)") and Compound 2 ("C2 (5 mg/kg)"), and Compound 2 in combination with fenofibrate (50 mg/kg) ("C2+Feno (50 mg/kg)") for 15 days. $*p \leq 0.05, p \leq 0.01, *p \leq 0.001, ****p \leq 0.0001$ and n=11-15 animals per treatment group. Data presented as mean±SD.
Figure 14A:
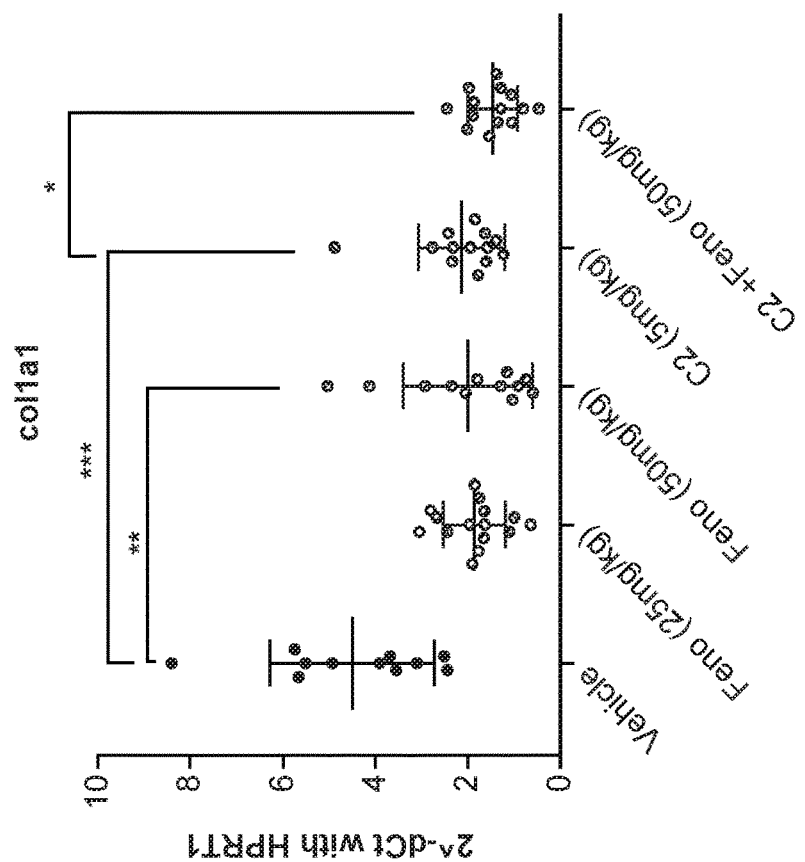

Table 7: Test Details fibrate (50 mg/kg) with Compound 2 significantly reduced plasma TG relative to vehicle, Compound 2, and fenofibrate (50 mg/kg) groups (FIG. 9). Treatment with Compound 2 resulted in decreased expression of PPARα target genes which were increased with combination treatment of Compound 2 with fenofibrate relative with Compound 2 and vehicle-treated groups (FIG. 10A). Conversely, treatment with Compound 2 was associated with increased expression of LXRα target genes, and combination of Compound 2 with fenofibrate (50 mg/kg) normalized expression (FIG. 10B). Compound 2 reduced plasma ALT and AST levels, and this was further reduced with the combination treatment with fenofibrate (50 mg/kg) (FIGS. 11A and 11B). Similarly, liver TG was reduced with single agent Compound 2 treatment and the combination Compound 2/fenofibrate treatment resulted in further reduction (FIG. 12A). Additionally, Compound 2 increased levels of hepatic ketone bodies (beta hydroxy butyrate (βOHB)), a marker for β-oxidation, which was further increased with combination treatment with fenofibrate (50 mg/kg) (FIG. 12B). Compound 2 administration for 15 days reduced hepatic oxidative stress (quantified as the amount of malondialdehyde), and co-administration of fenofibrate further reduced this parameter (FIG. 13). Fenofibrate alone (at both 25 and 50 mg/kg dose) had modest-to-no effect on the above-mentioned parameters. However, both Compound 2 and fenofibrate (50 mg/kg) single agent treatment reduced the hepatic expression of pro-fibrotic genes. The combination Compound 2/fenofibrate treatment had a greater effect than either single agent on the expression of pro-fibrotic genes (FIGS. 14A and 14B).

Conclusions:

The data demonstrate that co-administration of Compound 2 with a PPARα agonist can ameliorate plasma hypertriglyceridemia induced by ACC inhibition and have greater efficacy on steatosis and fibrosis endpoints.

| Treatment Group | Number of Animals | Dosing duration (days) | Necropsy time | Test Article | Dose (mg/kg) | Dose Vol. (mL/kg) | Dosing Frequency (x/day) | Route |
|---|---|---|---|---|---|---|---|---|
| 1 | 11 | 15 | 2 h post dose | Vehicle | 0 | 10 | QD | PO |
| 2 | 15 | 15 | 2 h post dose | Fenofibrate | 25 | 10 | QD | PO |
| 3 | 14 | 15 | 2 h post dose | Fenofibrate | 50 | 10 | QD | PO |
| 4 | 14 | 15 | 2 h post dose | Compound 2 | 5 | 10 | QD | PO |
| 5 | 14 | 15 | 2 h post dose | Compound 2 + Fenofibrate | 5 + 50 | 10 | QD | PO |

Vehicle: Vehicle: 25% (v/v) PEG 200, 75% (v/v) [0.5% (w/v) Methyl Cellulose A4M in purified water].
Compound 2 in vehicle solution (pH: between 7.5 and 8.5).
Fenofibrate in vehicle solution (pH: between 7.5 and 8.5).
Mice randomized to treatment groups based on body weights collected on Day 1.
Fructose/glucose water
Predose Phase
Animals 1 through 72: Fructose/glucose water
Dosing phase
All Groups: Fructose/glucose water
Whole blood sample and livers were collected at termination. Animals were sacrificed in the ad lib fed state, 2 h post dose.

After 15 days of dosing Compound 2 in the FFD model, plasma TG were significantly increased by 29% relative to vehicle-treated animals, whereas co-administration of feno-

We claim:

1. A method of treating, stabilizing or lessening the severity or progression of non-alcoholic steatohepatitis (NASH), wherein the method comprises administering to a human patient in need thereof Compound 1 having the formula:

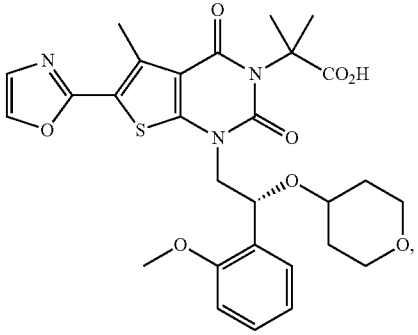

or a pharmaceutically acceptable salt thereof,
in combination with fenofibrate, or a salt thereof, and wherein the human patient has F3-F4 NASH fibrosis and the human patient has a plasma triglyceride level of at least about 150 mg/dL; and
wherein Compound 1 is administered in an amount of about 20 mg.

2. A method of treating, stabilizing or lessening the severity or progression of non-alcoholic steatohepatitis (NASH) while lessening the severity of hypertriglyceridemia, wherein the method comprises administering to a human patient in need thereof Compound 1 having the formula:

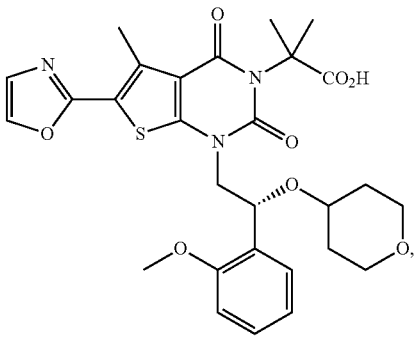

or a pharmaceutically acceptable salt thereof,
in combination with fenofibrate, or a salt thereof, and wherein the human patient has F3-F4 NASH fibrosis and the human patient has a plasma triglyceride level of at least about 150 mg/dL; and
wherein Compound 1 is administered in an amount of about 20 mg.

3. The method according to claim 1, wherein the human patient has compensated cirrhosis due to NASH.

4. The method according to claim 2, wherein the human patient has compensated cirrhosis due to NASH.

5. The method according to claim 2, wherein about 48 mg of fenofibrate is administered per day.

6. The method according to claim 2, about 145 mg of fenofibrate is administered per day.

7. The method according to claim 1, about 48 mg of fenofibrate is administered per day.

8. The method according to claim 1, wherein about 145 mg of fenofibrate is administered per day.

9. The method according to claim 6, further comprising administering an FXR agonist.

10. The method according to claim 8, further comprising administering an FXR agonist.

11. The method of claim 1, wherein administration of fenofibrate starts before administration of Compound 1 and optionally continues during at least part of the administration of Compound 1.

12. The method of claim 2, wherein administration of fenofibrate starts before administration of Compound 1 and optionally continues during at least part of the administration of Compound 1.

13. The method of claim 9, wherein the FXR agonist is administered at a dosage of about 30 mg per day.

14. The method of claim 10, wherein the FXR agonist is administered at a dosage of about 30 mg per day.

15. The method according to claim 1, wherein fenofibrate is administered at a dosage of about 30 mg to about 200 mg per day.

16. The method according to claim 2, wherein fenofibrate is administered at a dosage of about 30 mg to about 200 mg per day.

17. The method according to claim 9, wherein the FXR agonist is obeticholic acid or PX-102.

18. The method according to claim 10, wherein the FXR agonist is obeticholic acid or PX-102.

19. The method of claim 1, wherein administration of fenofibrate and administration of Compound 1 are simultaneous.

20. The method of claim 2, wherein administration of fenofibrate and administration of Compound 1 are simultaneous.

* * * * *